US008273958B2

(12) United States Patent
Napier et al.

(10) Patent No.: US 8,273,958 B2
(45) Date of Patent: Sep. 25, 2012

(54) PROCESS FOR THE PRODUCTION OF ARACHIDONIC ACID AND/OR EICOSAPENTAENOIC ACID

(75) Inventors: Johnathan A. Napier, Preston (GB); Olga Sayanova, Harpenden (GB)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 13/186,030

(22) Filed: Jul. 19, 2011

(65) Prior Publication Data

US 2012/0011618 A1 Jan. 12, 2012

Related U.S. Application Data

(62) Division of application No. 12/083,300, filed as application No. PCT/EP2006/067223 on Oct. 10, 2006, now Pat. No. 8,017,839.

(30) Foreign Application Priority Data

Oct. 13, 2005 (GB) .................................. 0520843.4

(51) Int. Cl.
*A01H 5/00* (2006.01)
*C12N 15/82* (2006.01)
*C07H 21/04* (2006.01)

(52) U.S. Cl. ......................... 800/298; 800/281; 536/23.2

(58) Field of Classification Search ........................ None
See application file for complete search history.

(56) References Cited

U.S. PATENT DOCUMENTS

| 5,614,393 A | 3/1997 | Thomas et al. |
| 2005/0132442 A1 | 6/2005 | Yadav et al. |

FOREIGN PATENT DOCUMENTS

| CA | 2180154 C | 7/1995 |
| CA | 2533613 A1 | 2/2005 |
| EP | 0550162 A1 | 7/1993 |
| EP | 0794250 A1 | 9/1997 |
| EP | 0472722 B1 | 5/2003 |
| WO | WO-91/13972 A1 | 9/1991 |
| WO | WO-93/06712 A1 | 4/1993 |
| WO | WO-93/11245 A1 | 6/1993 |
| WO | WO-94/11516 A1 | 5/1994 |
| WO | WO-94/18337 A1 | 8/1994 |
| WO | WO-95/18222 A1 | 7/1995 |
| WO | WO-96/21022 A2 | 7/1996 |
| WO | WO-97/21340 A1 | 6/1997 |
| WO | WO-97/30582 A1 | 8/1997 |
| WO | WO-98/46763 A1 | 10/1998 |
| WO | WO-98/46764 A1 | 10/1998 |
| WO | WO-98/46765 A1 | 10/1998 |
| WO | WO-98/46776 A2 | 10/1998 |
| WO | WO-99/27111 A1 | 6/1999 |
| WO | WO-99/33958 A2 | 7/1999 |
| WO | WO-99/64616 A2 | 12/1999 |
| WO | WO-00/21557 A1 | 4/2000 |
| WO | WO-00/34439 A1 | 6/2000 |
| WO | WO-2004/057001 A2 | 7/2004 |
| WO | WO-2005/012316 A2 | 2/2005 |
| WO | WO-2005/047479 A2 | 5/2005 |

OTHER PUBLICATIONS

Wang, X.M., et al., "Biosynthesis and regulation of linolenic acid in higher plants", Plant Physiol. Biochem., 1988, vol. 26, No. 6, pp. 777-792.

McKeon, T., et al., "Stearoyl-acyl carrier protein desaturase from safflower seeds", Methods in Enzymol., 1981, vol. 71, 275-281.

Huang, Y.-S., et al., "Cloning of Δ12- and Δ6-desaturases from *Mortierella alpina* and recombinant production of γ-linolenic acid in *Saccharomyces cerevisiae*", Lipids, 1999, vol. 34, No. 7, pp. 649-659.

Wada, H., et al., "Enhancement of chilling tolerance of a cyanobacterium by genetic manipulation of fatty acid desaturation", Nature, 1990, vol. 347, pp. 200-203.

Stukey, J.E., et al., "The OLE1 gene of *Saccharomyces cerevisiae* encodes the Δ9 fatty acid desaturase and can be functionally replaced by the rat stearoyl-CoA desaturase gene", J. Biol. Chem., 1990, vol. 265, No. 33, pp. 20144-20149.

Sayanova, O., et al., "A bifunctional Δ12, Δ15-desaturase from *Acanthamoeba castellanii* directs the synthesis of highly unusual *n*-1 series unsaturated fatty acids", J. Biol. Chem., 2006, vol. 281, No. 48, pp. 36533-36541.

(Continued)

*Primary Examiner* — Elizabeth McElwain
(74) *Attorney, Agent, or Firm* — Connolly Bove Lodge & Hutz LLP

(57) ABSTRACT

The present invention relates to a new process for the production of arachidonic acid and/or eicosapentaenoic acid in plants through the co-expression of a Δ-12-/Δ-15-desaturase, Δ-9-elongase, Δ-8-desaturase and a Δ-5-desaturase and a process for the production of lipids or oils having an increased content of unsaturated fatty acids, in particular ω-3 and ω-6 fatty acids having at least two double bonds and a 18 or 20 carbon atom chain length. Preferably the arachidonic acid and eicosapentaenoic acid are produced in at least a 1:2 ratio. The invention furthermore relates to the production of a transgenic plants, preferably a transgenic crop plant, having an increased content of arachidonic acid and/or eicosapentaenoic acid, oils or lipids containing $C_{18}$- or $C_{20}$-fatty acids with a double bond in position Δ5, 8, 9, 11, 12, 14, 15 or 17 of the fatty acid produced, respectively due to the expression of the Δ-12-/Δ-15-desaturase, of the Δ-9-elongase, of the Δ-8-desaturase and of the Δ-5-desaturase in the plant. The expression of the inventive Δ-12-/Δ-15-desaturase leads preferably to linoleic acid and linolenic acid as products having a double bond in the position Δ9, 12 and 15 of the fatty acid. The invention additionally relates to specific nucleic acid sequences encoding for proteins with Δ-12-/Δ-15-desaturase-, Δ-9-elongase-, Δ-8-desaturase- or Δ-5-desaturase-activity, nucleic acid constructs, vectors and transgenic plants containing said nucleic acid sequences.

22 Claims, 13 Drawing Sheets

OTHER PUBLICATIONS

"Mucor circinelloides D12d mRNA for delta-12 fatty acid desaturase complete cds", Database NCBI, Accession No. AB052087, Oct. 2, 2001.

Qi, B., et al. "Identification of a cDNA encoding a novel C18-$\Delta^9$ polyunsaturated fatty acid-specific elongating activity from the docosahexaenoic acid (DHA)-producing microalga, *Isochrysis galbana*", FEBS Letters, 2002, vol. 510, pp. 159-165.

Wallis, J.G., et al., "The $\Delta^8$-desaturase of *Euglena gracilis*: an alternate pathway for synthesis of 20-carbon polyunsaturated fatty acids", Archives of Biochemistry and Biophysics, 1999, vol. 365, No. 2, pp. 307-316.

Napier, J.A., et al., "Progress toward the production of long-chain polyunsaturated fatty acids in transgenic plants", Lipids, 2004, vol. 39, No. 11, pp. 1067-1075.

Qi, B., et al., "Production of very long chain polyunsaturated omega-3 and omega-6 fatty acids in plants", Nature Biotechnology, 2004, vol. 22, No. 6, pp. 739-745.

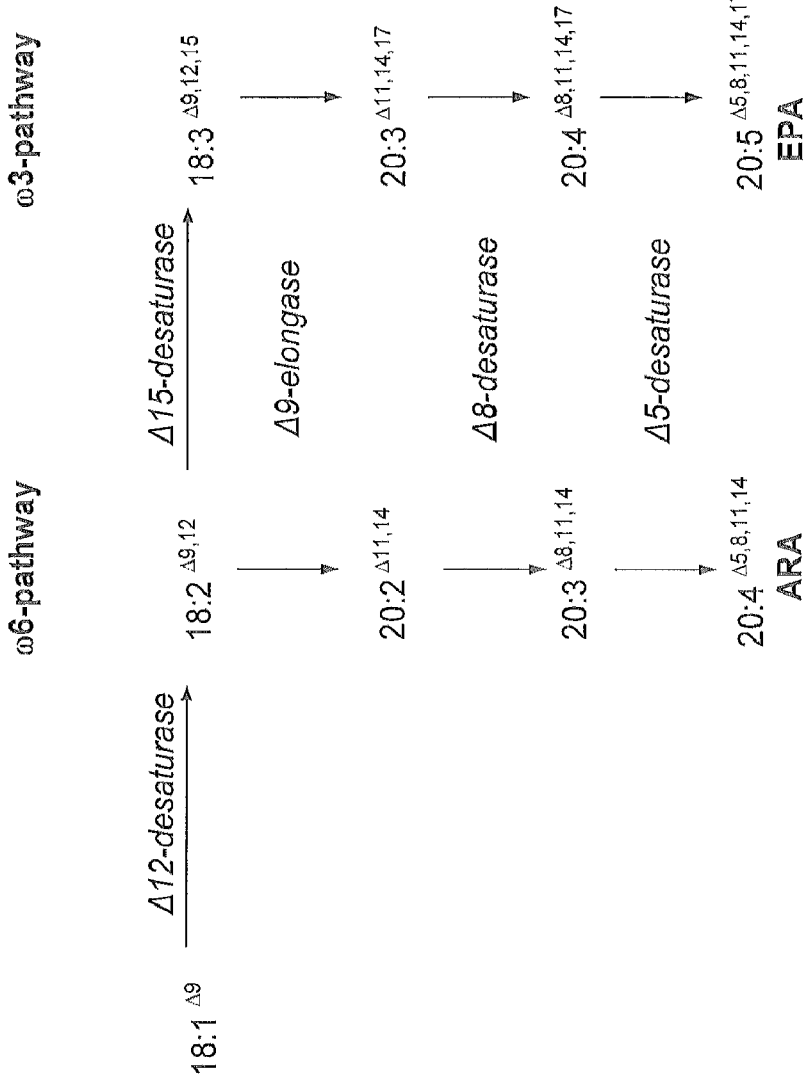
Figure 1: Biosynthesis pathway to ARA and/or EPA

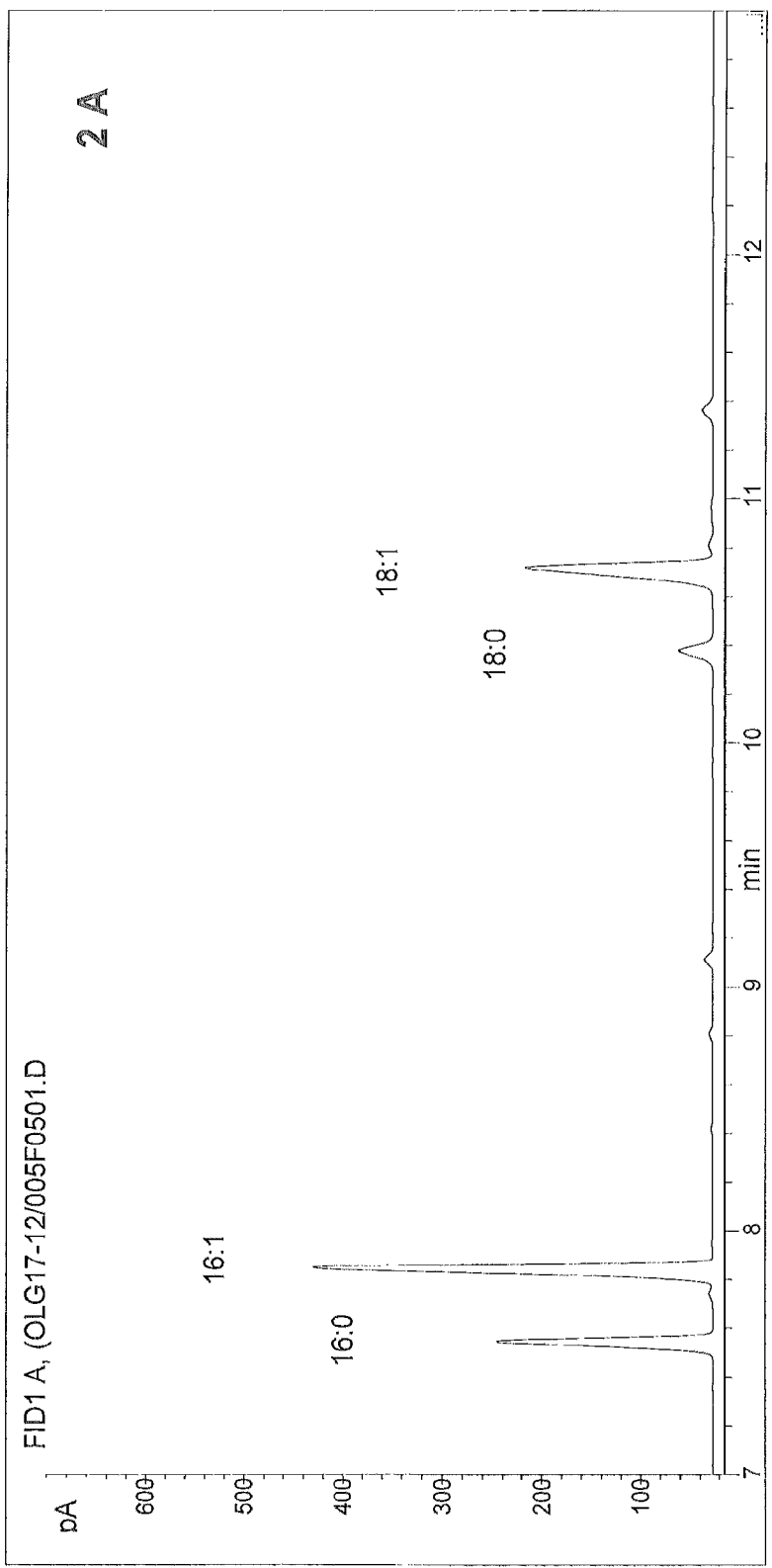
Figure 2 A: Comparison of the fatty acid profile of yeast transformed with the constructs pYES2 (2A) as control and construct pYES2-12Ac (2B). The fatty acids are marked. The new fatty acids synthesized are in case of construct pYES2-12Ac (2B) the fatty acids C16:2, C16:3, C18:2 and C18:3.

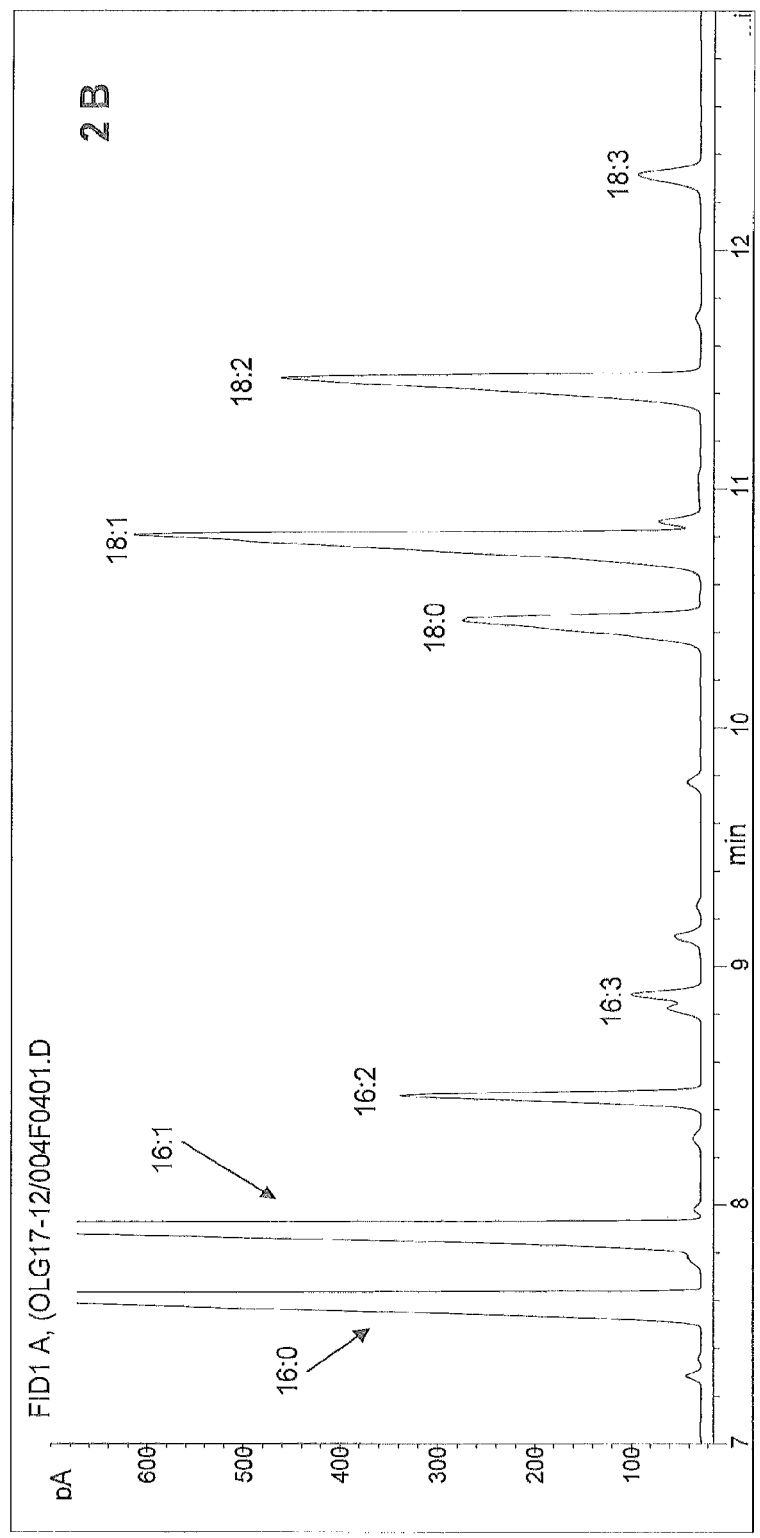
Figure 2B: Comparison of the fatty acid profile of yeast transformed with the constructs pYES2 (2A) as control and construct pYES2-12Ac (2B). The fatty acids are marked. The new fatty acids synthesized are in case of construct pYES2-12Ac (2B) the fatty acids C16:2, C16:3, C18:2 and C18:3.

Figure 3 A: Fatty acid profile of yeasts transformed with the construct pYES2 as control (Figure 3 A) and pYES2-8Ac (Figure 3 B) and fed with the fatty acid C20:2$^{\Delta 11,14}$. The respective fatty acids are marked.
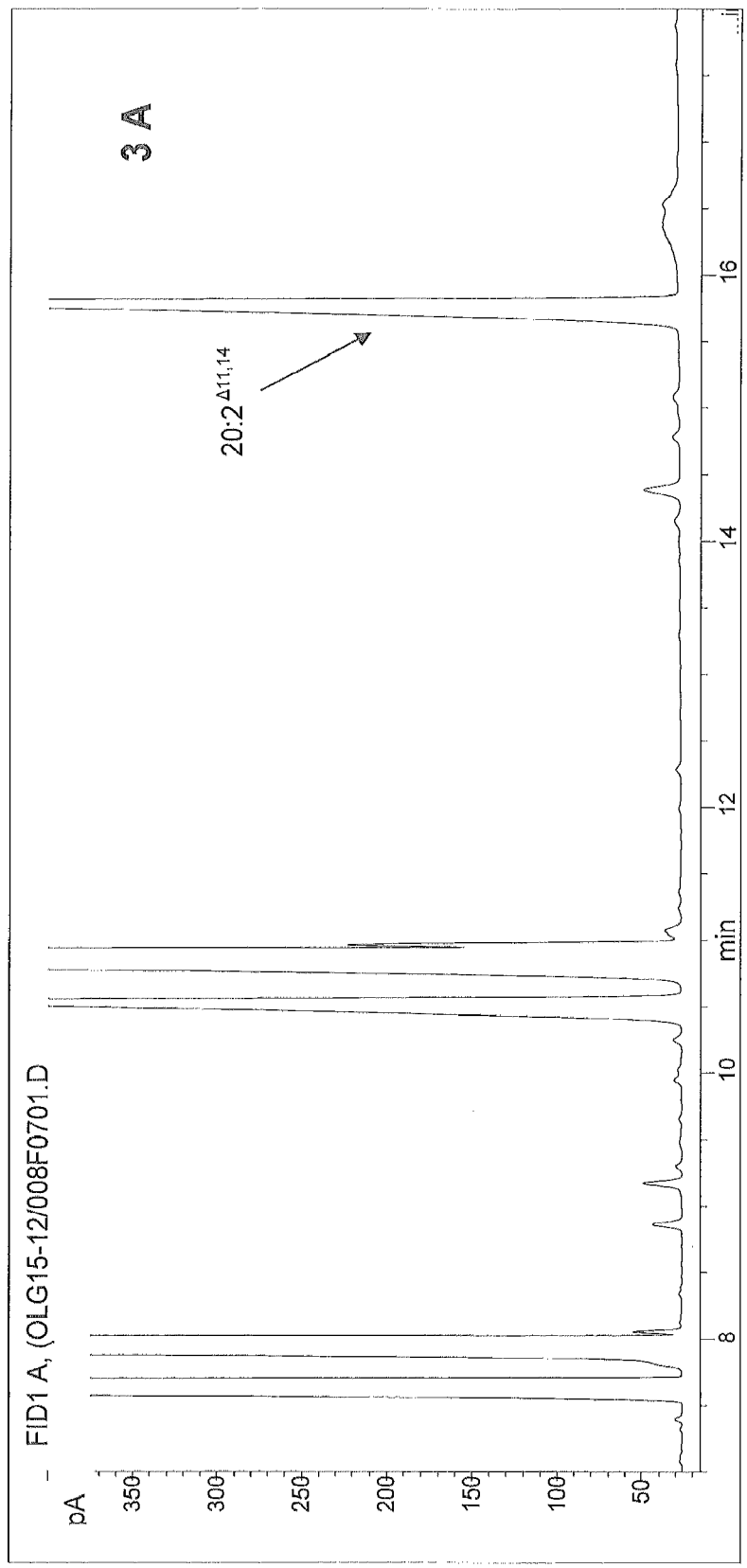

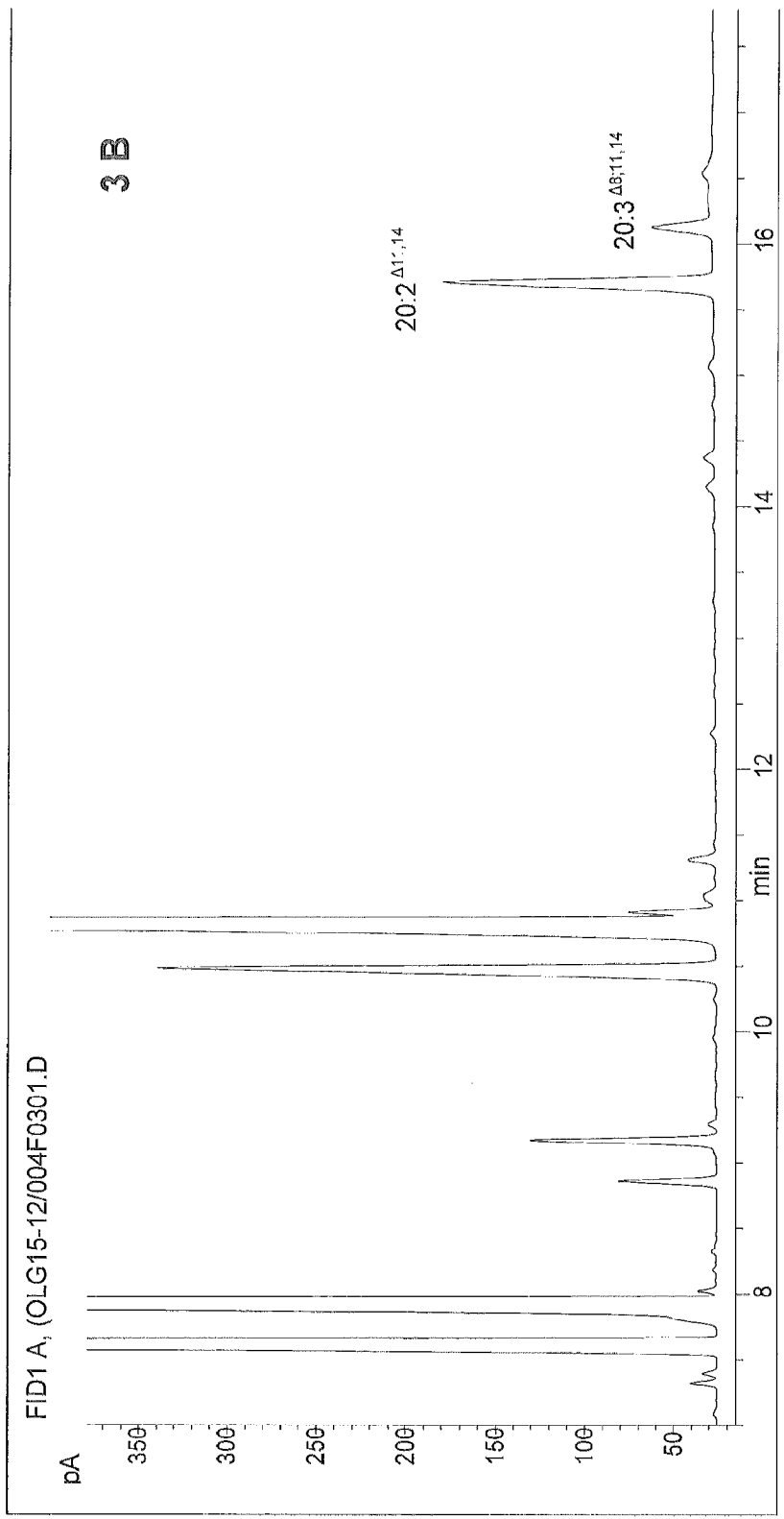
Figure 3 B: Fatty acid profile of yeasts transformed with the construct pYES2 as control (Figure 3 A) and pYES2-8Ac (Figure 3 B) and fed with the fatty acid C20:2$^{\Delta 11,14}$. The respective fatty acids are marked.

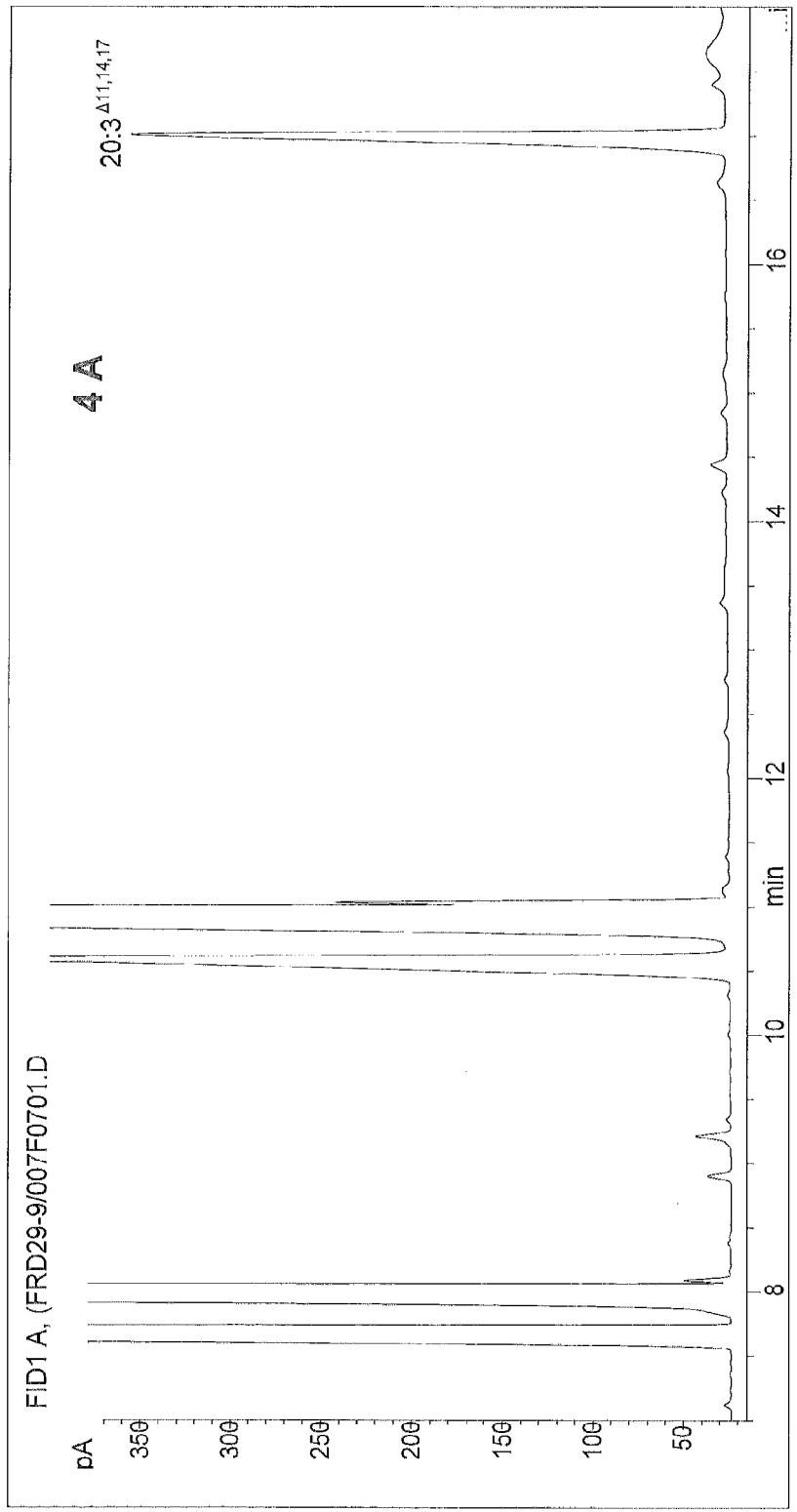
Figure 4 A: Fatty acid profile of yeast transformed with the construct pYES2 (Figure 4 A) as control and pYES2-8Ac (Figure 4 B) and fed with the fatty acid C20:3$^{\Delta 11,14,17}$. The respective fatty acids are market.

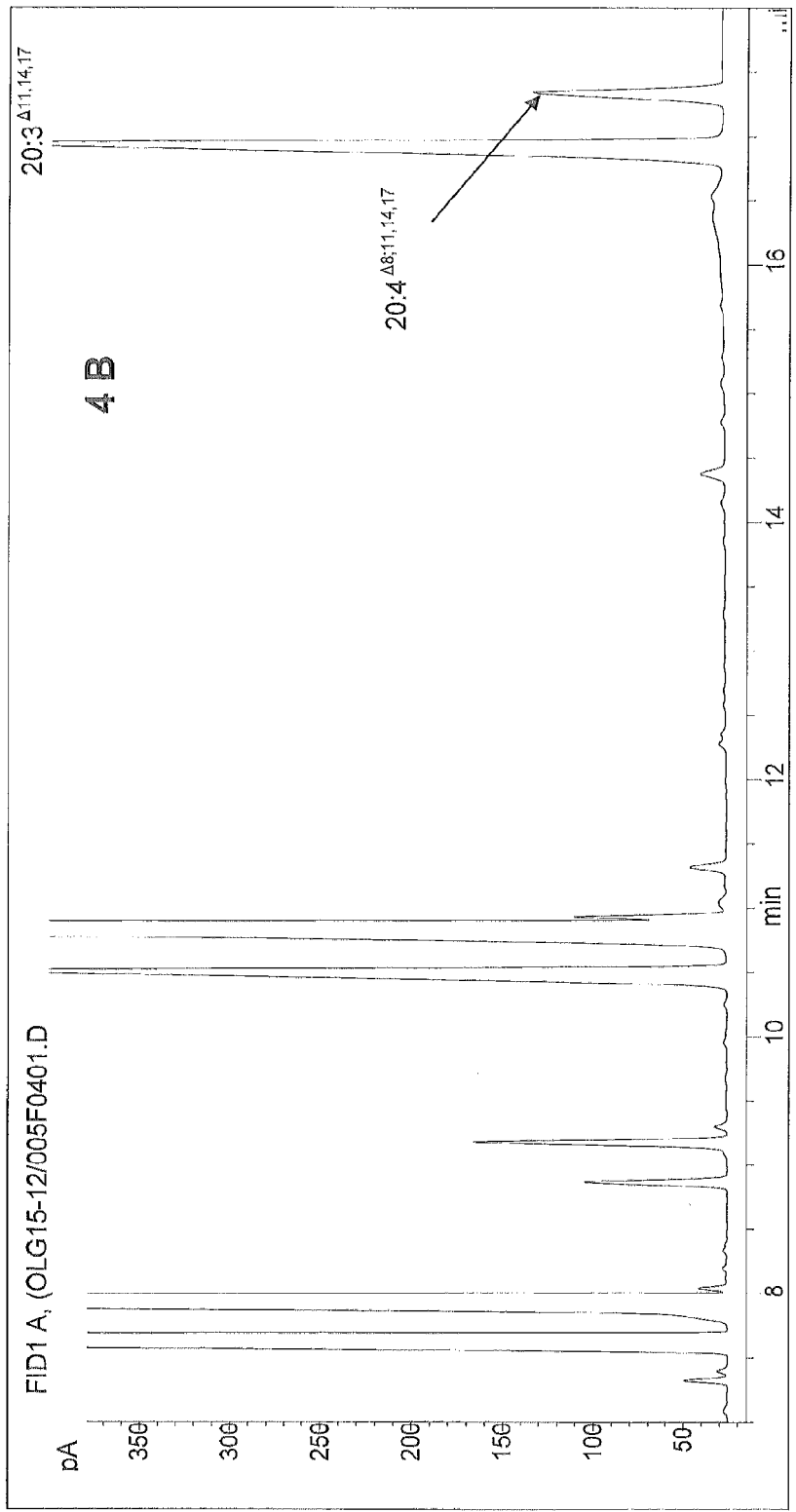
Figure 4 B: Fatty acid profile of yeast transformed with the construct pYES2 (Figure 4 A) as control and pYES2-8Ac (Figure 4 B) and fed with the fatty acid C20:3$^{\Delta11,14,17}$. The respective fatty acids are marked.

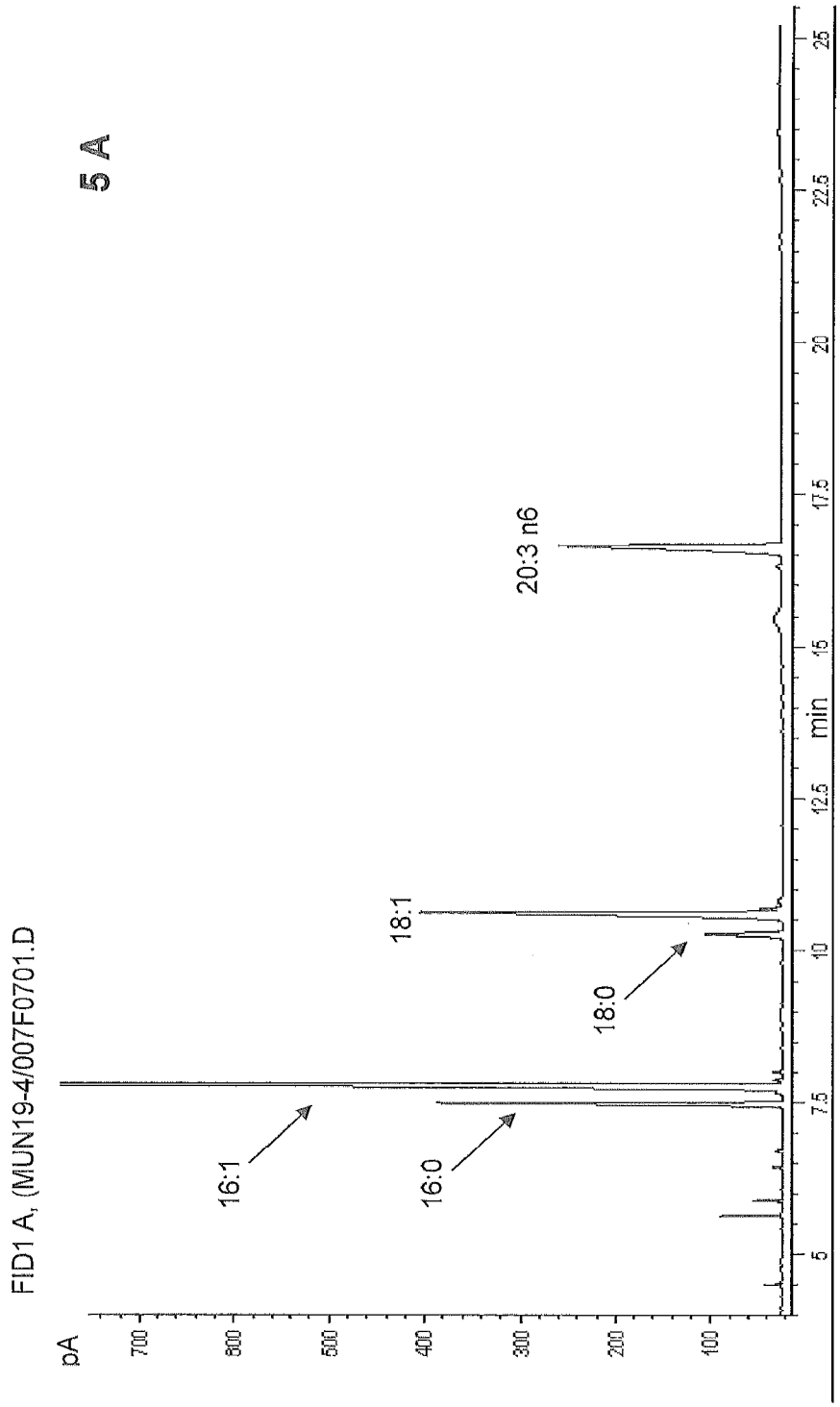
Figure 5 A: Comparison of the fatty acid profile of yeasts transformed with the construct pYES2 as control and fed with the fatty acid C20:3n-6 (Figure 5 A) and with the construct pYES2-5Pm fed with the fatty acid C20:3n-6 (Figure 5 B). The fatty acids are marked. The new synthesized fatty acid is C20:4n-6 (arachidonic acid).

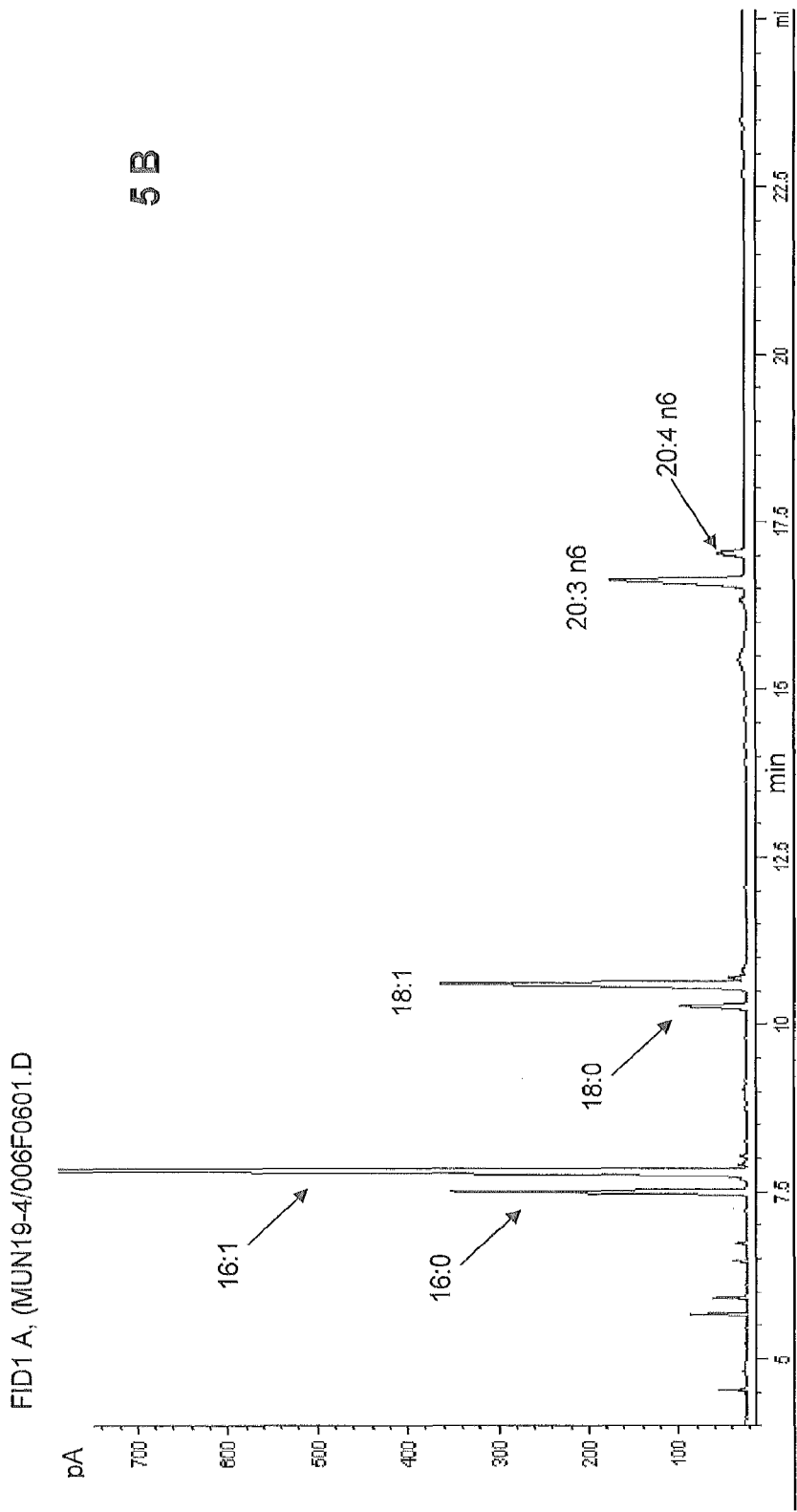
Figure 5 B: Comparison of the fatty acid profile of yeasts transformed with the construct pYES2 as control and fed with the fatty acid C20:3n-6 (Figure 5 A) and with the construct pYES2-5Pm fed with the fatty acid C20:3n-6 (Figure 5 B). The fatty acids are marked. The new synthesized fatty acid is C20:4n-6 (arachidonic acid).

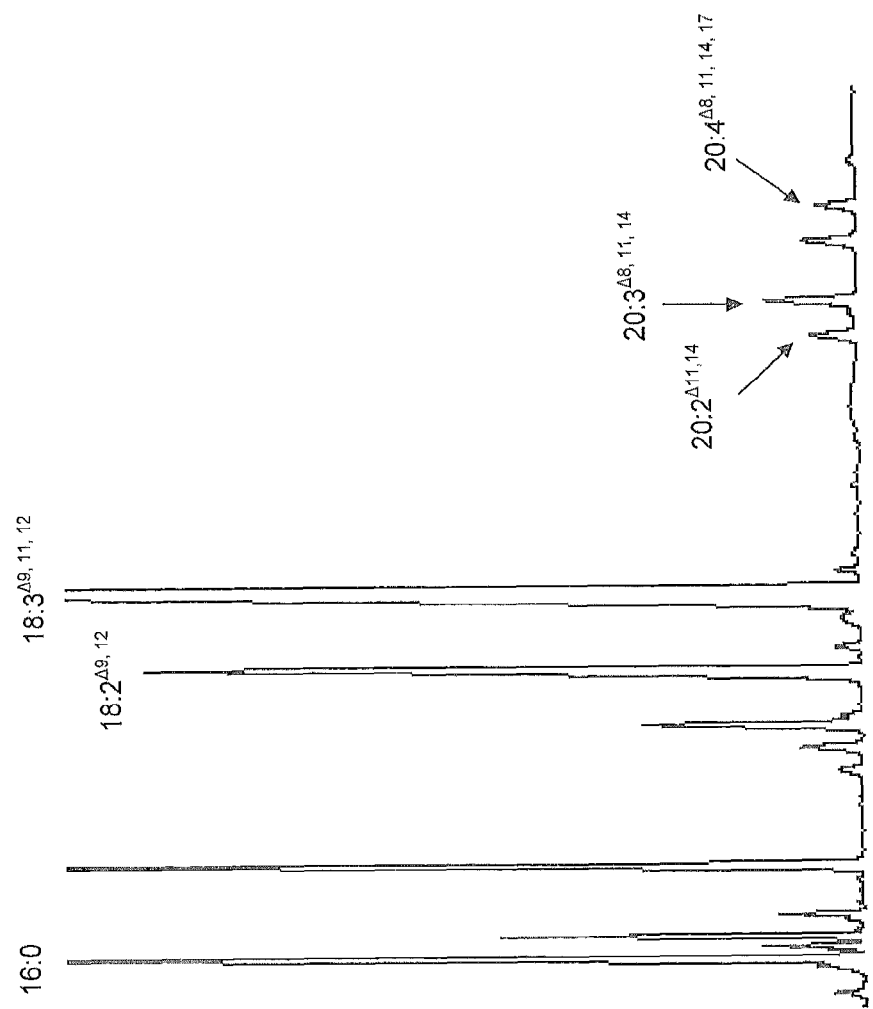
Figure 6: Expression of AcD8 in double transgenic Arabidopsis

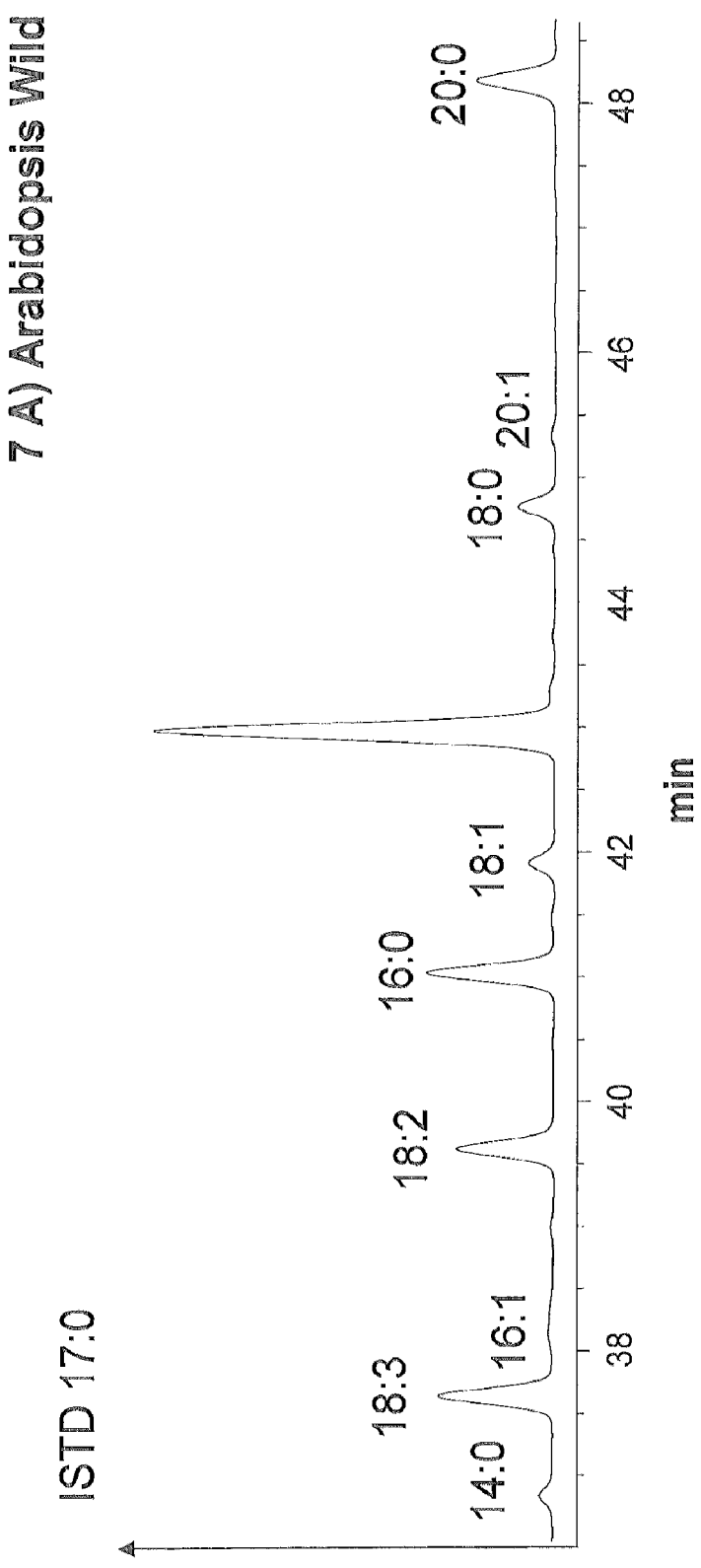
Figure 7 A: Expression of the Δ-9-elongase or Δ-9-elongase and Δ-8-desaturase in transgenic Arabidopsis

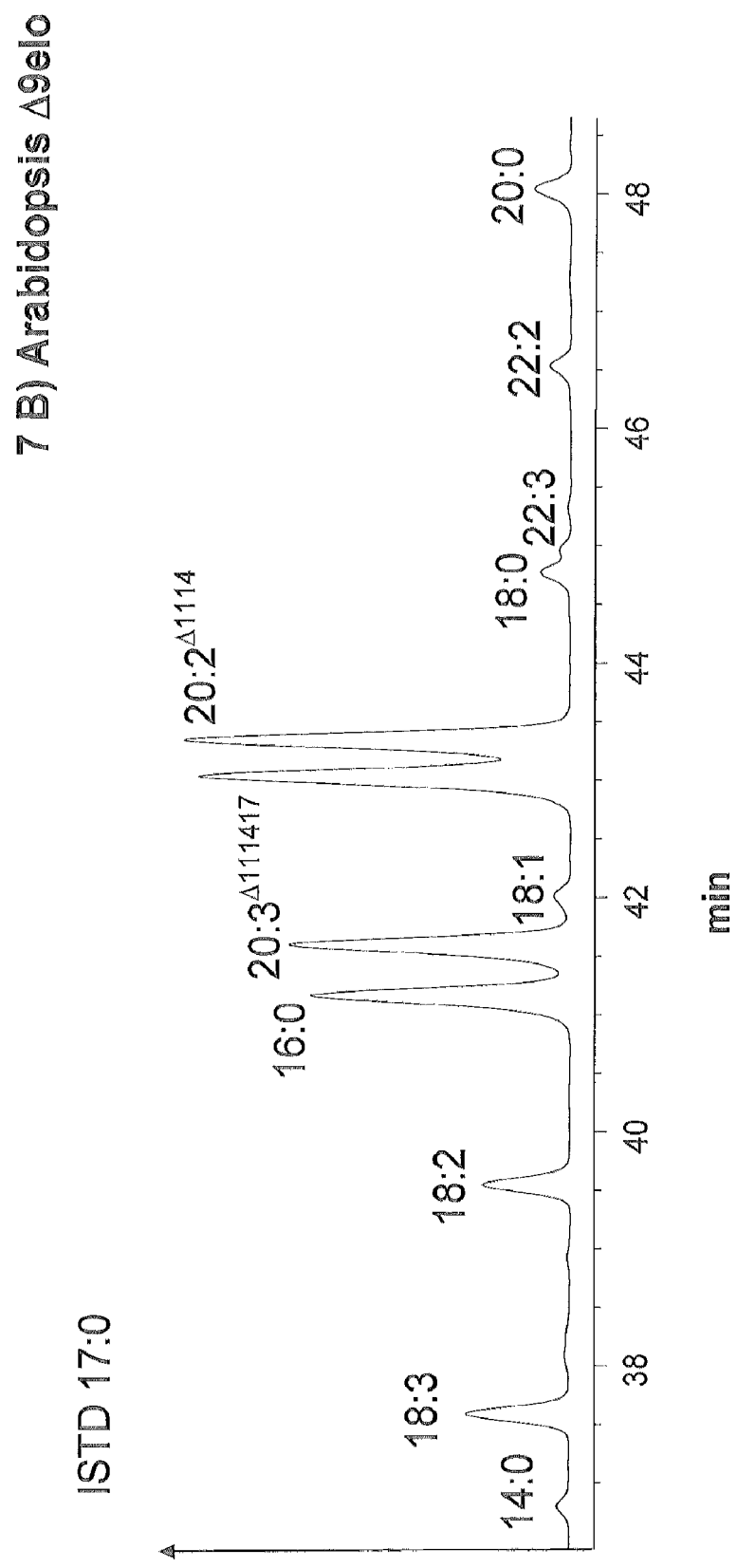
Figure 7 B: Expression of the Δ-9-elongase or Δ-9-elongase and Δ-8-desaturase in transgenic Arabidopsis

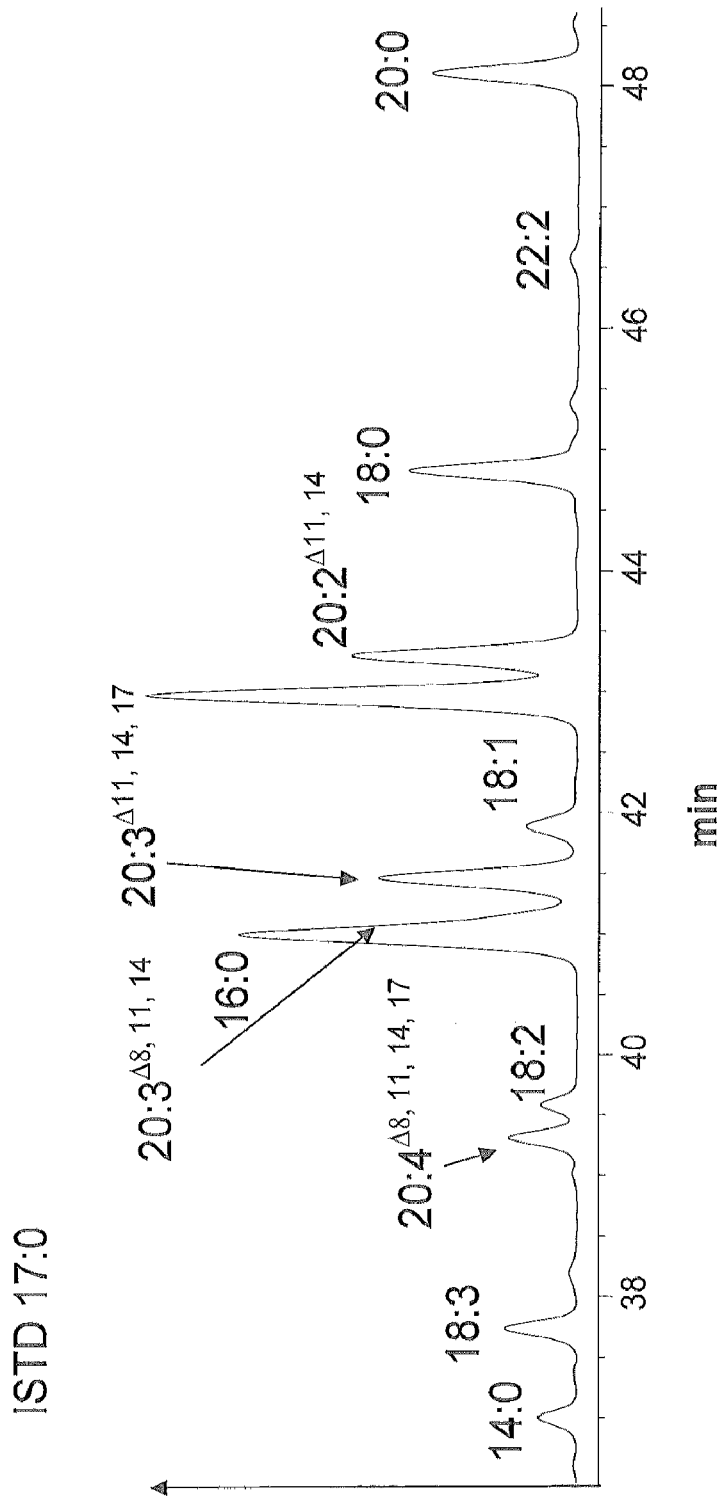
Figure 7 C: Expression of the Δ-9-elongase or Δ-9-elongase and Δ-8-desaturase in transgenic Arabidopsis

US 8,273,958 B2

PROCESS FOR THE PRODUCTION OF ARACHIDONIC ACID AND/OR EICOSAPENTAENOIC ACID

CROSS REFERENCE TO RELATED APPLICATIONS

This application is a divisional application of U.S. application Ser. No. 12/083,300 filed Apr. 9, 2008, now U.S. Pat. No. 8,017,839 which is a national stage application (under 35 U.S.C. §371) of PCT/EP2006/067223 filed Oct. 10, 2006, which claims benefit to United Kingdom application 0 520 843.4 filed Oct. 13, 2005. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_List_17418_00071_US. The size of the text file is 120 KB, and the text file was created on Sep. 2, 2011.

DESCRIPTION

The present invention relates to a new process for the production of arachidonic acid and/or eicosapentaenoic acid in plants through the co-expression of a Δ-12-/Δ-15-desaturase, Δ-9-elongase, Δ-8-desaturase and a Δ-5-desaturase and a process for the production of lipids or oils having an increased content of unsaturated fatty acids, in particular ω-3 and ω-6 fatty acids having at least two double bonds and a 18 or 20 carbon atom chain length. Preferably the arachidonic acid and eicosapentaenoic acid are produced in at least a 1:2 ratio.

The invention furthermore relates to the production of a transgenic plants, preferably a transgenic crop plant, having an increased content of arachidonic acid and/or eicosapentaenoic acid, oils or lipids containing $C_{18}$- or $C_{20}$-fatty acids with a double bond in position Δ5, 8, 9, 11, 12, 14, 15 or 17 of the fatty acid produced, respectively due to the expression of the Δ-12-/Δ-15-desaturase, of the Δ-9-elongase, of the Δ-8-desaturase and of the Δ-5-desaturase in the plant. The expression of the inventive Δ-12-/Δ-15-desaturase leads preferably to linoleic acid and α-linolenic acid as products having a double bond in the position Δ9, 12 and 15 of the fatty acid.

The invention additionally relates to specific nucleic acid sequences encoding for proteins with Δ-12-/Δ-15-desaturase-, Δ-9-elongase-, Δ-8-desaturase- or Δ-5-desaturase-activity, nucleic acid constructs, vectors and transgenic plants containing said nucleic acid sequences.

Plants and especially oil crops have been used for centuries as sources for edible and non-edible products. There are written records and archaeological excavations that oil crops such as linseed, olive and sesame were widespread use at least six thousand years ago.

Non-edible products of oilseed crops such as rapeseed were used and included in lubricants, oil lamps, and cosmetics such as soaps. Oil crops differ in their cultural, economic and utilization characteristics, for example rapeseed and linseed are adapted to relatively cool climates, whereas oil palm and coconut are adapted to warm and damp climates. Some plants are a real oilseed plant that means the main product of such plants is the oil, whereas in case of others such as cotton or soybean the oil is more or less a side product. The oils of different plants are basically characterized by their individual fatty acid pattern.

Fatty acids and triglycerides have numerous applications in the food industry, animal nutrition, cosmetics and in the drug sector. Depending on whether they are free saturated or unsaturated fatty acids or triglycerides with an increased content of saturated or unsaturated fatty acids, they are suitable for the most varied applications; thus, for example, long chain polyunsaturated fatty acids (=LCPUFAs) are added to infant formula to increase its nutritional value. The various fatty acids and triglycerides are mainly obtained from microorganisms such as *Mortierella* or from oil-producing plants such as soybean, oilseed rape, sunflower and others, where they are usually obtained in the form of their triacylglycerides. Alternatively, they are obtained advantageously from animals, such as fish. The free fatty acids are prepared advantageously by hydrolysis.

Whether oils with unsaturated or with saturated fatty acids are preferred depends on the intended purpose; thus, for example, lipids with unsaturated fatty acids, specifically polyunsaturated fatty acids, are preferred in human nutrition since they have a positive effect on the cholesterol level in the blood and thus on the possibility of heart disease. They are used in a variety of dietetic foodstuffs or medicaments. In addition PUFAs are commonly used in food, feed and in the cosmetic industry. Poly unsaturated ω-3- and/or ω-6-fatty acids are an important part of animal feed and human food. Because of the common composition of human food poly unsaturated ω-3-fatty acids, which are an essential component of fish oil, should be added to the food to increase the nutritional value of the food; thus, for example, poly unsaturated fatty acids such as Docosahexaenoic acid (=DHA, $C_{22:6}^{\Delta 4,7,10,13,16,19}$) or Eicosapentaenoic acid (=EPA, $C_{20:5}^{\Delta 5,8,11,14,17}$) are added as mentioned above to infant formula to increase its nutritional value. Whereas DHA has a positive effect on the brain development of babies. The addition of poly unsaturated ω-3-fatty acids is preferred as the addition of poly unsaturated ω-6-fatty acids like Arachidonic acid (=ARA, $C_{20:4}^{\Delta 5,8,11,14}$) to common food have an undesired effect for example on rheumatic diseases such as rheumatoid arthritis. Poly unsaturated ω-3- and ω-6-fatty acids are precursor of a family of paracrine hormones called eicosanoids such as prostaglandins which are products of the metabolism of Dihomo-γ-linoleic acid, ARA or EPA. Eicosanoids are involved in the regulation of lipolysis, the initiation of inflammatory responses, the regulation of blood circulation and pressure and other central functions of the body. Eicosanoids comprise prostaglandins, leukotrienes, thromboxanes, and prostacyclins. ω-3-fatty acids seem to prevent artherosclerosis and cardiovascular diseases primarily by regulating the levels of different eicosanoids. Other Eicosanoids are the thromboxanes and leukotrienes, which are products of the metabolism of ARA or EPA.

Principally microorganisms such as *Mortierella* or oil producing plants such as soybean, rapeseed or sunflower or algae such as *Crypthecodinium* or *Phaeodactylum* are a common source for oils containing PUFAs, where they are usually obtained in the form of their triacyl glycerides. Alternatively, they are obtained advantageously from animals, such as fish. The free fatty acids are prepared advantageously by hydrolysis with a strong base such as potassium or sodium hydroxide.

Plant oils are in general rich in fatty acids such as monounsaturated fatty acids like oleic acid or poly unsaturated fatty acids (=PUFA) like linoleic or linolenic acid. LCPUFAs like arachidonic acid or eicosapentaenoic acid are rarely found in plants exceptions are some *Nephelium* and *Salvia* species in which arachidonic acid is found and some *Santalum* species in which eicosapentaenoic acid is found. The LCPUFA Docosahexaenoic acid is not found in plants. LCPUFAs such as DHA, EPA, ARA, Dihomo-γ-linoleic acid ($C_{20:3}^{\Delta 8,11,14}$) or Docosapentaenoic acid (=DPA, $C_{22:5}^{\Delta 7,10,13,16,19}$) are not produced by oil producing plants such as soybean, rapeseed, safflower or sunflower. A natural sources for said fatty acids are fish for example herring, salmon, sardine, redfish, eel, carp, trout, halibut, mackerel, pikeperch, tuna or algae.

Approximately 80% of the oils and fats are used in the food industry. Nearly about 84% of all world wide used vegetable oils are stemming from only six crops/oil crops, which are soybean, oil palm, rapeseed, sunflower, cottonseed, and groundnut.

On account of their positive properties there has been no shortage of attempts in the past to make available genes which participate in the synthesis of fatty acids or triglycerides for the production of oils in various organisms having a modified content of unsaturated fatty acids. Thus, in WO 91/13972 and its US equivalent a Δ-9-desaturase is described. In WO 93/11245 a Δ-15-desaturase and in WO 94/11516 a Δ-12-desaturase is claimed. WO 00/34439 discloses a Δ-5- and a Δ-8-desaturase. Other desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. To date, however, the various desaturases have been only inadequately characterized biochemically since the enzymes in the form of membrane-bound proteins are isolable and characterizable only with very great difficulty (McKeon et al., Methods in Enzymol. 71, 1981: 275-277, Wang et al., Plant Physiol. Biochem., 26, 1988: 777-792). Generally, membrane-bound desaturases are characterized by introduction into a suitable organism, which is then investigated for enzyme activity by means of analysis of starting materials and products. Δ-6-Desaturases are described in WO 93/06712, U.S. Pat. No. 5,614,393, U.S. Pat. No. 5,614,393, WO 96/21022, WO0021557 and WO 99/27111 and their application to production in transgenic organisms is also described, e.g. in WO 9846763, WO 9846764 and WO 9846765. At the same time the expression of various fatty acid biosynthesis genes, as in WO 9964616 or WO 9846776, and the formation of poly-unsaturated fatty acids is also described and claimed. With regard to the effectiveness of the expression of desaturases and their effect on the formation of polyunsaturated fatty acids it may be noted that through expression of a desaturases and elongases as described to date only low contents of poly-unsaturated fatty acids/lipids, such as by way of example eicosapentaenoic or arachidonic acid, have been achieved. Therefore, an alternative and more effective pathway with higher product yield is desirable.

Accordingly, there is still a great demand for new and more suitable genes, which encode enzymes, which participate in the biosynthesis of unsaturated fatty acids and make it possible to produce certain fatty acids specifically on an industrial scale without unwanted byproducts forming. In the selection of genes for biosynthesis two characteristics above all are particularly important. On the one hand, there is as ever a need for improved processes for obtaining the highest possible contents of polyunsaturated fatty acids. Advantageously genes should be as selective as possible and should if possible have more than one activity in the fatty acid biosynthesis chain.

Accordingly, it is an object of the present invention to provide further genes of desaturase and elongase enzymes for the synthesis of polyunsaturated fatty acids in plants preferably in oilseed plants and to use them in a commercial process for the production of PUFAs especially LCPUFAs. Said process should increase LCPUFA content in plants as much as possible preferably in seeds of an oil producing plant.

BRIEF SUMMARY OF THE INVENTION

We have found that a process for the production of arachidonic acid or eicosapentaenoic acid achieves this object or arachidonic acid and eicosapentaenoic acid in transgenic plants that produces mature seeds with a content of at least 1% by weight of said compounds referred to the total lipid content of said organism, which comprises the following steps:

a) introduction of at least one nucleic acid sequence in said transgenic plant, which encodes a polypeptide having a Δ-12-desaturase and Δ-15-desaturase activity, and b) introduction of at least one second nucleic acid sequence in said transgenic plant, which encodes a polypeptide having a Δ-9-elongase activity, and c) introduction of at least one third nucleic acid sequence in said transgenic plant, which encodes a polypeptide having a Δ-8-desaturase activity, and d) introduction of at least a one fourth nucleic acid sequence, which encodes a polypeptide having a Δ-5-desaturase activity, and e) cultivating and harvesting of said transgenic plant.

According to the invention the used nucleic acid sequences are isolated nucleic sequences coding for polypeptides having a Δ-12-desaturase- and Δ-15-desaturase-, Δ9-elongase-, Δ-8 desaturase- or Δ5-desaturase-activity.

Advantageously nucleic acid sequences are used in the abovementioned process of the invention, which encode polypeptides having Δ-12-desaturase and Δ-15-desaturase activity, Δ-8-desaturase, Δ-9-elongase or Δ-5-desaturase activity and which are selected from the group consisting of a) a nucleic acid sequence depicted in SEQ ID NO: 1, SEQ ID NO: 3, SEQ ID NO: 5, SEQ ID NO: 7, SEQ ID NO: 9, SEQ ID NO: 11, SEQ ID NO:13, SEQ ID NO: 15, SEQ ID NO: 17, SEQ ID NO: 19, SEQ ID NO: 21 and SEQ ID NO: 23, and b) a nucleic acid sequence, which, as a result of the degeneracy of the genetic code, can be derived from a polypeptide sequence as depicted in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24 according to the degeneracy of the genetic code, c) derivatives of the nucleic acid sequences depicted in SEQ ID NO: 1, SEQ ID NO: 3, SEQ ID NO: 5, SEQ ID NO: 7, SEQ ID NO: 9, SEQ ID NO: 11, SEQ ID NO: 13, ID NO: 15, SEQ ID NO: 17, SEQ ID NO: 19, SEQ ID NO: 21 or SEQ ID NO: 23 which encode polypeptides having at least 50% homology to the sequence as depicted in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24 and which polypeptides having Δ-12-desaturase and Δ-15-desaturase activity, Δ-8-desaturase, Δ-9-elongase or Δ-5-desaturase activity.

BRIEF DESCRIPTION OF THE DRAWINGS

FIG. 1: Biosynthesis pathway to ARA and/or EPA.

FIGS. 2A and 2B: Comparison of the fatty acid profile of yeast transformed with the constructs pYES2 (FIG. 2A) as control and construct pYES2-12Ac (FIG. 2B). The fatty acids are marked. The new fatty acids synthesized are, in the case of construct pYES2-12Ac (FIG. 2B), the fatty acids C16:2, C16:3, C18:2 and C18:3.

FIGS. 3A and 3B: Fatty acid profile of yeasts transformed with the constructs pYES2 as control (FIG. 3A) and construct pYES2-8Ac (FIG. 3B) and fed with the fatty acid C20:2$^{\Delta11,14}$. The respective fatty acids are marked.

FIGS. 4A and 4B: Fatty acid profile of yeast transformed with the constructs pYES2 as control (FIG. 4A) and pYES2-8Ac (FIG. 4B) and fed with the fatty acid C20:3$^{\Delta11,14,17}$. The respective fatty acids are market.

FIGS. 5A and 5B: Comparison of the fatty acid profile of yeasts transformed with the constructs pYES2 as control (FIG. 5A) and pYES2-5Pm (FIG. 5 B) and fed with the fatty acid C20:3n-6. The fatty acids are marked. The new synthesized fatty acid is C20:4n-6 (arachidonic acid).

FIG. 6: Expression of AcD8 in double transgenic *Arabidopsis*.

FIGS. 7A-7C: Expression of the Δ-9-elongase or Δ-9-elongase and Δ-8-desaturase in transgenic *Arabidopsis*.

DETAILED DESCRIPTION OF THE INVENTION

In the inventive process the nucleic acid sequence encoding the bifunctional Δ-12-desaturase- and Δ-15-desaturase-enzyme leads to an increased flux from oleic acid (C18:1Δ9) to linolenic acid (C18:3$^{\Delta9,12,15}$) and thereby to an increase of ω-3-fatty acids in comparison to the ω-6-fatty acids. Furthermore this bifunctional enzyme acts on C16-fatty acids having one double bond in the fatty acid molecule as well as on C18-fatty acids having one double bond in the fatty acid molecule. This leads to a further increase in flux from precursor fatty acids such as C18 fatty acids such as oleic acid towards C18 fatty acids such as linoleic and linolenic acid. This is especially of advantage in plants such as oilseed plants having a high content of oleic acid like such as those from the family of the Brassicaceae, such as the genus *Brassica*, for example oilseed rape or canola; the family of the Elaeagnaceae, such as the genus *Elaeagnus*, for example the genus and species *Olea europaea*, or the family Fabaceae, such as the genus *Glycine*, for example the genus and species *Glycine max*, which are high in oleic acid. But also in other plants such oilseed plants like *Brassica juncea, Camelina sativa*, sunflower or safflower and all other plants mentioned herein this leads to a higher amount of ω-3-fatty acids. By using said inventive nucleic acid sequence and the activity of its gene product ω-3-fatty acids to the ω-6-fatty acids are produced in at least a 1:2 ratio, preferably in at least a 1:3 or 1:4 ratio, more preferably in at least a 1:5 or 1:6 ratio. That means especially arachidonic acid and eicosapentaenoic acid are produced in at least a 1:2 ratio, preferably in at least a 1:3 or 1:4 ratio, more preferably in at least a 1:5 or 1:6 ratio.

In particular ω-3-fatty acids or ω-6-fatty acids molecules are produced in the inventive process, arachidonic acid and eicosapentaenoic acid are most preferred produced. We have found that this object is advantageously achieved by the combined expression of four isolated nucleic acid sequences according to the invention which encode for polypeptides having the following activities: a polypeptide with Δ-12-desaturase- and Δ-15-desaturase-activity, a polypeptide with a C18-Δ-9-elongase-activity, a polypeptide with C20-Δ-8-desaturase-activity and a C20-Δ-5-desaturase-activity. This objective was achieved in particular by the co-expression of the isolated nucleic acid sequences according to the invention. C18 fatty acids with a single double bond in Δ-9-position are desaturated a first time to linoleic acid by the Δ-12-desaturase and Δ-15-desaturase and thereafter a second time to linolenic acid by the same enzyme advantageously used in the inventive process. The produced C18 fatty acids linoleic and linolenic acid both having a double bond in Δ-9-position are than elongated by the Δ-9-elongase, which is advantageously used in the inventive process. By the Δ-8-desaturase used in the process a double bond in Δ-8-position is introduced into C20 fatty acids. In addition a double bond is introduced into the produced fatty acid molecules in Δ-5-position by the Δ-5-desaturase. The end products of the whole enzymatic reaction are arachidonic acid and eicosapentaenoic acid.

The ω-3-fatty acids or ω-6-fatty acids, preferably ω-3-fatty acids produced in the process are advantageously bound in membrane lipids and/or triacylglycerides or mixtures of different glycerides, but may also occur in the plants as free fatty acids or else bound in the form of other fatty acid esters.

The fatty acid esters with ω-3-fatty acids or ω-6-fatty acids especially arachidonic acid and eicosapentaenoic acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetyl-coenzyme A esters from the plants which have been used for the preparation of the fatty acid esters; preferably, they are isolated in the form of their diacylglycerides, triacylglycerides and/or in the form of phosphatidylcholine, especially preferably in the form of the triacylglycerides. In addition to these esters, the LCPUFAs are also present in the plants, advantageously in the oilseed plants as free fatty acids or bound in other compounds. As a rule, the various abovementioned compounds (fatty acid esters and free fatty acids) are present in the plants with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

In the inventive process(es) [the singular shall include the plural and vice versa] the LCPUFAs are produced in a content of at least 1% by weight, preferably at least 2, 3, 4 or 5% by weight, more preferably at least 6, 7, 8, or 9% by weight, most preferably 10, 20 or 30% by weight referred to the total lipid content of the plant used in the process. That means Arachidonic acid and eicosapentaenoic acid are produced in a content of at least 1% by weight, preferably at least 2, 3, 4 or 5% by weight, more preferably at least 6, 7, 8, or 9% by weight, most preferably 10, 20 or 30% by weight referred to the total lipid content. Preferred starting material for the inventive process is oleic acid (C18:1), which is transformed to the preferred end products ARA or EPA. As for the inventive process plants are used the product of the process is not a product of one pure substance per se. It is a mixture of different substances where one or more compounds are the major product and others are only contained as side products. Advantageously the side products shall not exceed 20% by weight referred to the total lipid content of the plant, preferably the side products shall not exceed 15% by weight, more preferably they shall not exceed 10% by weight, most preferably they shall not exceed 5% by weight. In the event that a mixture of different fatty acids such as ARA and EPA are the product of the inventive process said fatty acids can be further purified by method known by a person skilled in the art such as distillation, extraction, crystallization at low temperatures, chromatography or a combination of said methods. These chemically pure fatty acids or fatty acid compositions are advantageous for applications in the food industry sector, the cosmetic sector and especially the pharmacological industry sector.

Fatty acid esters or fatty acid mixtures produced by the process according to the invention advantageously comprise 6 to 15% of palmitic acid, 1 to 6% of stearic acid, 7 to 85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids including LCPUFAs, in each case based on 100% and on the total fatty acid content of the organisms. Advantageous LCPUFAs, which are present in the fatty acid esters or fatty acid mixtures are preferably at least 1%, 2%, 3%, 4% or 5% by weight of arachidonic acid and/or preferably at least 5%, 6%, 7%, 8%, 9% or 10% by weight of eicosapentaenoic acid, based on the total fatty acid content.

Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t3c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. In a further preferred form of the invention, these abovementioned fatty acids occur to less than 0.9%, 0.8%, 0.7%, 0.6% or 0.5%, especially preferably to less than 0.4%, 0.3%, 0.2%, 0.1%, based on the total fatty acids. The fatty acid esters or fatty acid mixtures produced by the process according to the invention advantageously comprise less than 0.1%, based on the total fatty acids, and/or no butyric acid, no cholesterol, no clupanodonic acid (=docosapentaenoic acid, $C22:5^{\Delta 4,8,12,15,21}$) and no nisinic acid (tetracosahexaenoic acid, $C23:6^{\Delta 3,8,12,15,21}$).

The isolated nucleic acid sequences used in the process according to the invention encode proteins or parts of these, where the proteins or the individual protein or parts thereof comprise(s) an amino acid sequence with sufficient homology to an amino acid sequence which is shown in the sequences SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22 and SEQ ID NO: 24 so that the proteins or parts thereof retain a Δ-12-desaturase and Δ-15-desaturase-, Δ-9-elongase-, Δ-8-desaturase- and/or Δ-5-desaturase activity. The proteins or parts thereof which is/are encoded by the nucleic acid molecule(s) preferably retains their essential enzymatic activity and the ability of participating in the metabolism of compounds required for the synthesis of cell membranes or lipid bodies in organisms, advantageously in plants, or in the transport of molecules across these membranes. Advantageously, the proteins encoded by the nucleic acid molecules have at least approximately 50%, preferably at least approximately 60% and more preferably at least approximately 70%, 80% or 90% and most preferably at least approximately 85%, 86%, 87%, 88%, 89%, 90%, 91%, 92%, 93%, 94%, 95%, 96%, 97%, 98%, 99% or more identity with the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22 and SEQ ID NO: 24. For the purposes of the invention, homology or homologous is understood as meaning identity or identical, respectively.

The homology was calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignment. The sequence homology values which are indicated above as a percentage were determined over the entire sequence region using the program GAP and the following settings: Gap Weight: 50, Length Weight: 3, Average Match: 10.000 and Average Mismatch: 0.000. Unless otherwise specified, these settings were always used as standard settings for the sequence alignments.

Moreover, in the process of the invention advantageously nucleic acid sequences are used which differ from one of the nucleotide sequences shown in SEQ ID NO: 1, SEQ ID NO: 3, SEQ ID NO: 5, SEQ ID NO: 7, SEQ ID NO: 9, SEQ ID NO: 11, SEQ ID NO:13, SEQ ID NO: 15, SEQ ID NO: 17, SEQ ID NO: 19, SEQ ID NO: 21 and SEQ ID NO: 23 (and parts thereof) owing to the degeneracy of the genetic code and which thus encode the same Δ-12-desaturase and Δ-15-desaturase, Δ-9-elongase, Δ-8-desaturase or Δ-5-desaturase as those encoded by the nucleotide sequences shown in SEQ ID NO: 1, SEQ ID NO: 3, SEQ ID NO: 5, SEQ ID NO: 7, SEQ ID NO: 9, SEQ ID NO: 11, SEQ ID NO:13, SEQ ID NO: 15, SEQ ID NO: 17, SEQ ID NO: 19, SEQ ID NO: 21 and SEQ ID NO: 23.

Suitable plants for the production in the process according to the invention are, in principle all plants that produces mature seeds especially crop plants such as oilseed plants.

Plants which are suitable are, in principle, all those plants which are capable of synthesizing fatty acids and that produce mature seeds, such as all dicotyledonous or monocotyledonous plants. Advantageous plants are selected from the group consisting of the plant families Anacardiaceae, Asteraceae, Apiaceae, Boraginaceae, Brassicaceae, Cannabaceae, Elaeagnaceae, Euphorbiaceae, Fabaceae, Geraniaceae, Gramineae, Juglandaceae, Leguminosae, Linaceae, Lythrarieae, Malvaceae, Onagraceae, Palmae, Poaceae, Rubiaceae, Scrophulariaceae, Solanaceae, Sterculiaceae and Theaceae or vegetable plants or ornamentals. More preferred plants are selected from the group consisting of the plant genera of

*Pistacia, Mangifera, Anacardium, Calendula, Carthamus, Centaurea, Cichorium, Cynara, Helianthus, Lactuca, Locusta, Tagetes, Valeriana, Borago, Daucus, Brassica, Camelina, Melanosinapis, Sinapis, Arabadopsis, Orychophragmus, Cannabis, Elaeagnus, Manihot, Janipha, Jatropha, Ricinus, Pisum, Albizia, Cathormion, Feuillea, Inga, Pithecolobium, Acacia, Mimosa, Medicajo, Glycine, Dolichos, Phaseolus, Pelargonium, Cocos, Oleum, Juglans, Wallia, Arachis, Linum, Punica, Gossypium, Camissonia, Oenothera, Elaeis, Hordeum, Secale, Avena, Sorghum, Andropogon, Holcus, Panicum, Oryza, Zea, Triticum, Coffea, Verbascum, Capsicum, Nicotiana, Solanum, Lycopersicon, Theobroma* and *Camellia*.

Examples which may be mentioned are the following plants selected from the group consisting of Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Boraginaceae, such as the genus *Borago*, for example the genus and species *Borago officinalis* [borage], Brassicaceae, such as the genera *Brassica, Camelina, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Camelina sativa, Melanosinapis communis* [mustard], *Brassica oleracea* [fodder beet] or *Arabidopsis thaliana*, Cannabaceae, such as the genus *Cannabis*, such as the genus and species *Cannabis sativa* [hemp], Elaeagnaceae, such as the genus *Elaeagnus*, for example the genus and species *Olea europaea* [olive], Euphorbiaceae, such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [cassava] or *Ricinus communis* [castor-oil plant], Fabaceae, such as the genera *Pisum, Albizia, Cathormion, Feuillea, Inga, Pithecolobium, Acacia, Mimosa, Medicajo, Glycine, Dolichos, Phaseolus*, soybean, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbeck, Feuilleea lebbeck, Mimosa lebbeck, Mimosa speciosa, Medicago sativa, Medicago falcata, Medicago varia* [alfalfa] *Glycine max Dolichos soja, Glycine gracilis, Glycine hispida, Phaseolus max, Soja hispida* or *Soja max* [soybean], Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Leguminosae, such as the genus *Arachis*, for example the genus and species *Arachis hypogaea* [peanut], Linaceae, such as the genera *Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Onagraceae, such as the genera *Camissonia, Oenothera*, for example the genera and species *Oenothera biennis* or *Camissonia brevipes* [evening primrose], Palmae, such as the genus *Elaeis*, for example the genus and species *Elaeis guineensis* [oil palm], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize] *Triticum aestivum, Triticum durum, Triticum turgidum, Triticum hybernum, Triticum macha, Triticum sativum* or *Triticum vulgare* [wheat], Rubiaceae, such as the genus *Coffea*, for example the genera and species *Coffea* spp., *Coffea arabica, Coffea canephora* or *Coffea liberica* [coffee], Scrophulariaceae, such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [verbascum], Solanaceae, such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant] *Lycopersicon esculentum, Lycopersicon lycopersicum, Lycopersicon pyriforms,*

*Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea].

Plants which are especially advantageously used in the process according to the invention are plants which belong to the oil-producing plants, that is to say which are used for the production of oil, such as oilseed or oil crop plants which comprise large amounts of lipid compounds, such as peanut, oilseed rape, canola, sunflower, safflower (*Carthamus tinctoria*), poppy, mustard, hemp, castor-oil plant, olive, sesame, *Calendula, Punica*, evening primrose, verbascum, thistle, wild roses, hazelnut, almond, *macadamia*, avocado, bay, pumpkin/squash, linseed, soybean, pistachios, borage, trees (oil palm, coconut or walnut) or arable crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are plants which are high in C18:1-, C18:2- and/or C18:3-fatty acids, such as oilseed rape, canola, *Brassica juncea, Camelina sativa, Orychophragmus*, sunflower, safflower, tobacco, verbascum, sesame, cotton, pumpkin/squash, poppy, evening primrose, walnut, linseed, hemp or thistle. Very especially preferred plants are plants such as rapeseed, canola, safflower, sunflower, poppy, mustard, hemp, evening primrose, walnut, linseed or hemp. Other preferred plants are castor bean, sesame, olive, *calendula, punica*, hazel nut, maize, almond, *macadamia*, cotton, avocado, pumpkin, laurel, pistachio, oil palm, peanut, soybean, marigold, coffee, tobacco, cacao and borage For the production of further ω-6- and/or ω-3-fatty acids it is advantageously to introduce further nucleic fatty acid sequences, which encode other enzymes of the fatty acids synthesis chain such as preferably Δ-5-elongase(s) and/or Δ-4-desaturase(s) [for the purposes of the present invention, the plural is understood as comprising the singular and vice versa]. Other Genes of the fatty acid or lipid metabolism, which can be introduced are selected from the group consisting of acyl-CoA dehydrogenase(s), acyl-ACP [=acyl carrier protein] desaturase(s), acyl-ACP thioesterase(s), fatty acid acyl transferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allenoxide synthases, hydroperoxide lyases or fatty acid elongase(s). Preferred nucleic acid sequences, which can be used in addition in the inventive process, are disclosed in the sequence protocol of WO2005/012316 and in Table 1 of the specification of said application, these sequences are hereby incorporated by reference.

Transgenic plants are to be understood as meaning single plant cells, certain tissues, organs or parts of plants and their cultures on solid media or in liquid culture, parts of plants and entire plants such as plant cell cultures, protoplasts from plants, callus cultures or plant tissues such as leafs, stem, shoots, seeds, flowers, roots, tubers etc. Said transgenic plants can be cultivated for example on solid or liquid culture medium, in soil or in hydroponics. Plants in the sense of the invention also include plant cells and certain tissues, organs and parts of plants in all their phenotypic forms such as anthers, fibers, root hairs, stalks, embryos, calli, cotelydons, petioles, harvested material, plant tissue, reproductive tissue such as seeds and cell cultures which are derived from the actual transgenic plant and/or can be used for bringing about the transgenic plant. In this context, the seed comprises all parts of the seed such as the seed coats, epidermal cells, seed cells, endosperm or embryonic tissue.

For the purposes of the invention, "transgenic" or "recombinant" means with regard to, for example, a nucleic acid sequence, an expression cassette (=gene construct) or a vector comprising the nucleic acid sequence or an organism transformed with the nucleic acid sequences, gene constructs or vectors as described herein according to the invention, all those constructions brought about by recombinant methods in which either a) the nucleic acid sequence according to the invention, or
b) a genetic control sequence which is operably linked with the nucleic acid sequence according to the invention, for example a promoter, or
c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding Δ12-desaturase and Δ15-desaturase-, Δ-9-elongase-, Δ-8-desaturase- and/or Δ5-desaturase-genes—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is therefore understood as meaning, as above, that the nucleic acids used in the process are not at their natural locus in the genome of a plant, it being possible for the nucleic acids to be expressed homologously or heterologously. However, as mentioned, transgenic also means that, while the nucleic acids according to the invention are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic organisms are oilseed crops.

After cultivation transgenic plants which are used in the inventive process can be brought to the market without isolating the ω-6- and/or ω-3-fatty acids preferably the arachidonic and/or eicosapentaenoic acid. Preferably the ω-6- and/or ω-3-fatty acids are isolated from the plant in the form of their free fatty acids, their lipids or oils. The purification can be done by conventional methods such as squeezing and extraction of the plants or other methods instead of the extraction such as distillation, crystallization at low temperatures, chromatography or a combination of said methods. Advantageously the plants are grinded, heated and/or vaporized before the squeezing and extraction procedure. As solvent for the extraction solvents such as hexane or other solvents having a similar extraction behavior are used. The isolated oils are further purified by acidification with for example phosphoric acid. The free fatty acids are produced from said oils or lipids by hydrolysis. Charcoal or diatom earth is used to remove dyes from the fluid. In another preferred embodiment of the inventive process the alkyl ester of the fatty acids are produced from the oils and lipids by transesterification with an enzyme of with conventional chemistry. A preferred method is the production of the alkyl ester in the presence of alcoholates of the corresponding lower alcohols (C1 to C10 alcohols such as methanol, ethanol, propanol, butanol, hexanol etc.) such as methanolate or ethanolate. Therefore as the skilled worker knows the alcohol in the presence of a catalytic amount of a base such as NaOH or KOH is added to the oils or lipids.

In a preferred form of the inventive process the lipids can be obtained in the usual manner after the plants have been grown. To this end, the organisms can first be harvested and then disrupted, or they can be used directly. In the case of plant cells, plant tissue or plant organs, "growing" is understood as meaning, for example, the cultivation on or in a nutrient medium, or of the intact plant on or in a substrate, for example in a hydroponic culture, potting compost or on arable land. It is advantageous to extract the lipids with suitable solvents such as apolar solvents, for example hexane, or polar solvents, for example ethanol, isopropanol, or mixtures such as hexane/isopropanol, phenol/chloroform/isoamyl alcohol, at temperatures between 0° C. and 80° C., preferably between 20° C. and 50° C. As a rule, the biomass is extracted with an excess of solvent, for example with an excess of solvent to biomass of 1:4. The solvent is subsequently removed, for example by distillation. The extraction may also be carried out with supercritical $CO_2$. After the extraction, the remainder of the biomass can be removed, for example, by filtration. Standard methods for the extraction of fatty acids from plants and microorganisms are described in Bligh et al. (Can. J. Biochem. Physiol. 37, 1959: 911-917) or Vick et al. (Plant Physiol. 69, 1982: 1103-1108).

The crude oil thus obtained can then be purified further, for example by removing cloudiness by adding polar solvents such as acetone or apolar solvents such as chloroform, followed by filtration or centrifugation. Further purification via columns or other techniques is also possible.

To obtain the free fatty acids from the triglycerides, the latter are hydrolyzed in the customary manner, for example using NaOH or KOH.

In the inventive process oils, lipids and/or free fatty acids or fractions thereof are produced. Said products can be used for the production of feed and food products, cosmetics or pharmaceuticals.

The oils, lipids, LCPUFAs or fatty acid compositions produced according to the inventive process can be used in the manner with which the skilled worker is familiar for mixing with other oils, lipids, fatty acids or fatty acid mixtures of animal origin, such as, for example, fish oils and/or microbial oils such as from *Mortierella* or *Crypthecodinium*. These oils, lipids, fatty acids or fatty acid mixtures, which are composed of vegetable, microbial and/or animal constituents, may also be used for the preparation of feedstuffs, foodstuffs, cosmetics or pharmaceuticals.

The term "oil", "lipid" or "fat" is understood as meaning a fatty acid mixture comprising unsaturated, saturated, preferably esterified, fatty acid(s). The oil, lipid, fat, fatty acid and/or fatty acid composition is preferably high in polyunsaturated (PUFA and/or LCPUFA) free and/or, advantageously, esterified fatty acid(s), in particular oleic acid, linoleic acid, α-linolenic acid, arachidonic acid and/or eicosatetraenoic acid.

Transgenic plants which comprise the LCPUFAs synthesized in the process according to the invention can also advantageously be marketed directly without there being any need for the oils, lipids or fatty acids synthesized to be isolated.

However, the LCPUFAs produced in the process according to the invention can also be isolated from the plants as described above, in the form of their oils, fats, lipids and/or free fatty acids. Polyunsaturated fatty acids produced by this process can be obtained by harvesting the crop in which they grow, or from the field. This can be done via pressing or extraction of the plant parts, preferably the plant seeds. In this context, the oils, fats, lipids and/or free fatty acids can be obtained by what is known as cold-beating or cold-pressing without applying heat. To allow for greater ease of disruption of the plant parts, specifically the seeds, they are previously comminuted, steamed or roasted. The seeds, which have been pretreated in this manner can subsequently be pressed or extracted with solvents such as warm hexane. The solvent is subsequently removed. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, substances such as the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigment remaining in the product, the products are subjected to bleaching, for example using filler's earth or active charcoal. At the end, the product is deodorized, for example using steam.

The preferred biosynthesis site of the fatty acids, oils, lipids or fats in the plants which are advantageously used is, for example, in general the seed or cell strata of the seed, so that seed-specific expression of the nucleic acids used in the process makes sense. However, it is obvious that the biosynthesis of fatty acids, oils or lipids need not be limited to the seed tissue, but can also take place in a tissue-specific manner in all the other parts of the plant, for example in epidermal cells or in the tubers.

In principle, the LCPUFAs produced by the process according to the invention in the organisms used in the process can be increased in two different ways. Advantageously, the pool of free polyunsaturated fatty acids and/or the content of the esterified polyunsaturated fatty acids produced via the process can be enlarged. Advantageously, the pool of esterified polyunsaturated fatty acids in the transgenic plants is enlarged by the process according to the invention.

In principle all nucleic acids encoding polypeptides with Δ-8-desaturase, Δ-9-elongase and/or Δ-5-desaturase activity can be used in the inventive process. Preferably the nucleic acid sequences can be isolated for example from microorganism or plants such as fungi like *Mortierella*, algae like *Euglena*, *Crypthecodinium* or *Isochrysis*, diatoms like

*Phaeodactylum*, protozoa like amoeba such as *Acanthamoeba* or *Perkinsus* or mosses like *Physcomitrella* or *Ceratodon*, but also non-human animals such as *Caenorhabditis* are possible as source for the nucleic acid sequences. Advantageous nucleic acid sequences according to the invention which encode polypeptides having a Δ-8-desaturase, Δ-9-elongase and/or Δ-5-desaturase activity are originate from microorganisms or plants, advantageously *Phaeodactylum tricornutum, Ceratodon purpureus, Physcomitrella patens, Euglena gracilis, Acanthamoeba castellanii, Perkinsus marinus* or *Isochrysis galbana*. Thus, the co expression of a C18-specific Δ-12-desaturase and Δ-15-desaturase, a C18-specific Δ-9 elongase, a C20-specific Δ-8-desaturase and a C20-specific Δ-5-desaturase leads to the formation of Arachidonic acid (C20:6n-4, Δ5, 8, 11, 14) and/or Eicosapentaenoic acid (C20:3n-5, Δ5, 8, 11, 14, 17). Most preferred are the sequences mentioned in the sequence protocol.

In another embodiment the invention furthermore relates to isolated nucleic acid sequences encoding polypeptides with Δ-12-desaturase and Δ-15-desaturase-, Δ-9-elongase-, Δ-8-desaturase- and/or Δ-5-desaturase-activity.

In one embodiment the invention relates to an isolated nucleic acid sequence which encodes a polypeptide having a Δ-12-desaturase and Δ-15-desaturase activity selected from the group consisting of
a) a nucleic acid sequence depicted in SEQ ID NO: 19, SEQ ID NO: 21 or SEQ ID NO: 23;
b) a nucleic acid sequence, which, as a result of the degeneracy of the genetic code, can be derived from a polypeptide sequence as depicted in SEQ ID NO: 20, SEQ ID NO: 22 or SEQ ID NO: 24;
c) derivatives of the nucleic acid sequence depicted in SEQ ID NO: 19, SEQ ID NO: 21 or SEQ ID NO: 22 which encode polypeptides having at least 40% homology to the sequence as depicted in SEQ ID NO: 20, SEQ ID NO: 22 or SEQ ID NO: 24 and which polypeptides having Δ-12-desaturase and Δ-15-desaturase activity.

This inventive Δ-12-desaturase and Δ-15-desaturase is able to desaturate C16-fatty acids having at least one double bond in the fatty acid chain and/or C18-fatty acids having at least one double bond in the fatty acid chain. Preferably C16- and/or C18-fatty acids having only one double bond in the fatty acid chain are desaturated. This activity leads to an increase in flux from precursor fatty acids such as C18-fatty acids towards C18-fatty acids having more than one double bond in the fatty acid chain such as linoleic and/or linolenic acid. C18-fatty acids are more preferred in the reaction than C16-fatty acids. C18-fatty acids are more than doubled preferred.

In another embodiment the invention relates to an isolated nucleic acid sequence comprising a nucleotide sequence which encodes a Δ-9-elongase selected from the group consisting of
a) a nucleic acid sequence depicted in SEQ ID NO: 11;
b) a nucleic acid sequence, which, as a result of the degeneracy of the genetic code, can be derived from a polypeptide sequence as depicted in SEQ ID NO: 12;
c) derivatives of the nucleic acid sequence depicted in SEQ ID NO: 11 which encode polypeptides having at least 70% homology to the sequence as depicted in SEQ ID NO: 12 and which polypeptides having Δ-9-elongase activity.

In yet another embodiment the invention relates to an isolated nucleic acid sequence comprising a nucleotide sequence which encodes a Δ-8-desaturase selected from the group consisting of
a) a nucleic acid sequence depicted in SEQ ID NO: 3, SEQ ID NO: 5 or SEQ ID NO: 7;
b) a nucleic acid sequence, which, as a result of the degeneracy of the genetic code, can be derived from a polypeptide sequence as depicted in SEQ ID NO: 4, SEQ ID NO: 6 or SEQ ID NO: 8;
c) derivatives of the nucleic acid sequence depicted in SEQ ID NO: 3, SEQ ID NO: 5 or SEQ ID NO: 7 which encode polypeptides having at least 70% homology to the sequence as depicted in SEQ ID NO: 4, SEQ ID NO: 6 or SEQ ID NO: 8 and which polypeptides having Δ-8-desaturase activity.

Further in another embodiment the invention relates to an isolated nucleic acid sequence comprising a nucleotide sequence which encodes a Δ-5-desaturase selected from the group consisting of
a) a nucleic acid sequence depicted in SEQ ID NO: 15 or SEQ ID NO: 17;
b) a nucleic acid sequence, which, as a result of the degeneracy of the genetic code, can be derived from a polypeptide sequence as depicted in SEQ ID NO: 16 or SEQ ID NO: 18;
c) derivatives of the nucleic acid sequence depicted in SEQ ID NO: 15 or SEQ ID NO: 17 which encode polypeptides having at least 70% homology to the sequence as depicted in SEQ ID NO: 16 or SEQ ID NO: 18 and which polypeptides having Δ-5-desaturase activity.

By derivative(s) of the sequences according to the invention is meant, for example, functional homologues of the polypeptides or enzymes encoded by SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 which exhibit the same said specific enzymatic activity. This specific enzymatic activity allows advantageously the synthesis of LCPUFAs of the ω-6- and/or ω-3-pathway of the fatty acid synthesis chain such as ARA and/or EPA. The said sequences encode enzymes which exhibit Δ-12-desaturase and Δ-15-desaturase-, Δ-9-elongase-, Δ-8-desaturase- and/or Δ-5-desaturase-activity.

The enzyme according to the invention, Δ-12-desaturase and Δ-15-desaturase, Δ-9-elongase, Δ-8-desaturase and/or Δ-5-desaturase, advantageously either elongates fatty acid chains with 18 carbon atoms (see SEQ ID NO: 11) or introduces a double bond into fatty acid residues of glycerolipids, free fatty acids or acyl-CoA fatty acids at position $C_8$-$C_9$ (see SEQ ID NO: 3, 5 or 7) or at position $C_5$-$C_6$ (see SEQ ID NO: 15 or 17) or at position $C_{12}$-$C_{13}$ and $C_{15}$-$C_{16}$ of the fatty acid chain (see SEQ ID NO: 19, 21 or 23).

The inventive nucleic acid molecules, for example a nucleic acid molecule with a nucleotide sequence of SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 or of a part thereof can be isolated using molecular-biological standard techniques and the sequence information provided herein. Also, for example a homologous sequence or homologous, conserved sequence regions can be identified at the DNA or amino acid level with the aid of comparative algorithms. They can be used as hybridization probe and standard hybridization techniques (such as, for example, those described in Sambrook et al., Molecular Cloning: A Laboratory Manual. 2nd ed., Cold Spring Harbor Laboratory, Cold Spring Harbor Laboratory Press, Cold Spring Harbor, N.Y., 1989) for isolating further nucleic acid sequences which can be used in the process. Moreover, a nucleic acid molecule comprising a complete sequence of SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 or a part thereof can be isolated by polymerase chain reaction, where oligonucleotide primers which are used on the basis of this sequence or parts thereof (for example a nucleic acid molecule comprising the complete sequence or part thereof can be isolated by polymerase chain reaction using oligonucleotide primers which have been generated based on this same sequence). For example, mRNA can be isolated from cells (for example by means of the guanidinium thiocyanate extraction method of Chirgwin et al. (1979) Biochemistry 18:5294-5299) and cDNA by means of reverse transcriptase (for example Moloney MLV reverse transcriptase, available from Gibco/BRL, Bethesda, Md., or AMV reverse transcriptase, available from Seikagaku America, Inc., St. Petersburg, Fla.). Synthetic oligonucleotide primers for the amplification by means of polymerase chain reaction can be generated based on one of the sequences shown in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 or with the aid of the amino acid sequences detailed in SEQ ID NO: 4, SEQ ID NO: 6, SEQ ID NO: 8, SEQ ID NO: 12, SEQ ID NO: 16, SEQ ID NO: 18, SEQ ID NO: 20, SEQ ID NO: 22 or SEQ ID NO: 24. A nucleic acid according to the invention can be amplified by standard PCR amplification techniques using cDNA or, alternatively, genomic DNA as template and suitable oligonucleotide primers. The nucleic acid amplified thus can be cloned into a suitable vector and characterized by means of DNA sequence analysis. Oligonucleotides, which correspond to a desaturase nucleotide sequence can be generated by standard synthetic methods, for example using an automatic DNA synthesizer.

Homologs of the Δ-12-desaturase and Δ-15-desaturase, Δ-9-elongase, Δ-8-desaturase or Δ-5-desaturase nucleic acid sequences with the sequence SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 means, for example, allelic variants with at least approximately 50 or 60%, preferably at least approximately 60 or 70%, more preferably at least approximately 70 or 80%, 90% or 95% and even more preferably at least approximately 85%, 86%, 87%, 88%, 89%, 90%, 91%, 92%, 93%, 94%, 95%, 96%, 97%, 98%, 99% or more identity or homology with a nucleotide sequence shown in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 or its homologs, derivatives or analogs or parts thereof. Furthermore, isolated nucleic acid molecules of a nucleotide sequence which hybridize with one of the nucleotide sequences shown in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 or with a part thereof, for example hybridized under stringent conditions. A part thereof is understood as meaning, in accordance with the invention, that at least 25 base pairs (=bp), 50 bp, 75 bp, 100 bp, 125 bp or 150 bp, preferably at least 175 bp, 200 bp, 225 bp, 250 bp, 275 bp or 300 bp, especially preferably 350 bp, 400 bp, 450 bp, 500 bp or more base pairs are used for the hybridization. It is also possible and advantageous to use the full sequence. Allelic variants comprise in particular functional variants which can be obtained by deletion, insertion or substitution of nucleotides from/into the sequence detailed in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23, it being intended, however, that the enzyme activity of the resulting proteins which are synthesized is advantageously retained for the insertion of one or more genes. Proteins which retain the enzymatic activity of the Δ-12-desaturase and Δ-15-desaturase, Δ-9-elongase, Δ-8-desaturase or Δ-5-desaturase, i.e. whose activity is essentially not reduced, means proteins with at least 10%, preferably 20%, especially preferably 30%, very especially preferably 40% of the original enzyme activity in comparison with the protein encoded by SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23. The homology was calculated over the entire amino acid or nucleic acid sequence region. The skilled worker has available a series of programs which are based on various algorithms for the comparison of various sequences. Here, the algorithms of Needleman and Wunsch or Smith and Waterman give particularly reliable results. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignment. The sequence homology values which are indicated above as a percentage were determined over the entire sequence region using the program GAP and the following settings: Gap Weight: 50, Length Weight: 3, Average Match: 10.000 and Average Mismatch: 0.000. Unless otherwise specified, these settings were always used as standard settings for the sequence alignments.

Homologs of SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 means for example also bacterial, fungal and plant homologs, truncated sequences, single-stranded DNA or RNA of the coding and noncoding DNA sequence.

Homologs of SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 also means derivatives such as, for example, promoter variants. The promoters upstream of the nucleotide sequences detailed can be modified by one or more nucleotide exchanges, by insertion(s) and/or deletion(s) without the functionality or activity of the promoters being adversely affected, however. It is furthermore possible that the modification of the promoter sequence enhances their activity or that they are replaced entirely by more active promoters, including those from heterologous organisms.

In a further embodiment, derivatives of the nucleic acid molecule according to the invention represented in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 encode proteins with at least 40%, advantageously approximately 50 or 60%, advantageously at least approximately 60 or 70% and more preferably at least approximately 70 or 80%, 80 to 90%, 90 to 95% and most preferably at least approximately 96%, 97%, 98%, 99% or more homology (=identity) with a complete amino acid sequence of SEQ ID NO: 4, SEQ ID NO: 6, SEQ ID NO: 8, SEQ ID NO: 12, SEQ ID NO: 16, SEQ ID NO: 18, SEQ ID NO: 20, SEQ ID NO: 22 or SEQ ID NO: 24. The homology was calculated over the entire amino acid or nucleic acid sequence region. The program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970) and Smith and Waterman (Adv. Appl. Math. 2; 482-489 (1981)], which are part of the GCG software packet [Genetics Computer Group, 575 Science Drive, Madison, Wis., USA 53711 (1991)], were used for the sequence alignment. The sequence homology values which are indicated above as a percentage were determined over the entire sequence region using the program BestFit and the following settings: Gap Weight: 50, Length Weight: 3, Average Match: 10.000 and Average Mismatch: 0.000. Unless otherwise specified, these settings were always used as standard settings for the sequence alignments.

Moreover, the invention comprises nucleic acid molecules which differ from one of the nucleotide sequences shown in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 (and parts thereof) owing to the degeneracy of the genetic code and which thus encode the same Δ-12-desaturase and Δ-15-desaturase, Δ-9-elongase, Δ-8-desaturase or Δ-5-desaturase as those encoded by the nucleotide sequences shown in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23.

In addition to the Δ-12-desaturase and Δ-15-desaturase, Δ-9-elongase, Δ-8-desaturase or Δ-5-desaturase shown in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23, the skilled worker will recognize that DNA sequence polymorphisms which lead to changes in the amino acid sequences of the Δ-12-desaturase and Δ-15-desaturase, Δ-9-elongase, Δ-8-desaturase or Δ-5-desaturase may exist within a population. These genetic polymorphisms in the Δ-12-desaturase and Δ-15-desaturase, Δ-9-elongase, Δ-8-desaturase or Δ-5-desaturase gene may exist between individuals within a population owing to natural variation. These natural variants usually bring about a variance of 1 to 5% in the nucleotide sequence of the Δ-12-desaturase and Δ-15-desaturase, Δ-9-elongase, Δ-8-desaturase or Δ-5-desaturase gene. Each and every one of these nucleotide variations and resulting amino acid polymorphisms in the Δ-12-desaturase and Δ-15-desaturase, Δ-9-elongase, Δ-8-desaturase or Δ-5-desaturase which are the result of natural variation and do not modify the functional activity are to be encompassed by the invention.

The nucleic acid sequence(s) according to the invention (for purposes of the application the singular encompasses the plural and vice versa) or fragments thereof may advantageously be used for isolating other genomic sequences via homology screening.

The said derivatives may be isolated, for example, from other organisms, eukaryotic organisms such as plants, especially mosses, algae, dinoflagellates, protozoa or fungi.

Allele variants include in particular functional variants obtainable by deletion, insertion or substitution of nucleotides in the sequences depicted in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 the enzymatic activity of the derived synthesized proteins being retained.

Starting from the DNA sequence described in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 or parts of said sequences such DNA sequences can be isolated using, for example, normal hybridization methods or the PCR technique from other eukaryotes such as those identified above for example. These DNA sequences hybridize under standard conditions with the said sequences. For hybridization use is advantageously made of short oligonucleotides of the conserved regions of an average length of about 15 to 70 bp, preferably of about 17 to 60 bp, more preferably of about 19 to 50 bp, most preferably of about 20 to 40 bp, for example, which can be determined by comparisons with other desaturase or elongase genes in the manner known to those skilled in the art. The histidine box sequences are advantageously employed. However, longer fragments of the nucleic acids according to the invention or the complete sequences may also be used for hybridization. Depending on the nucleic acid employed: oligonucleotide, longer fragment or complete sequence, or depending on which type of nucleic acid, DNA or RNA, is used for hybridization these standard conditions vary. Thus, for example, the melting temperatures of DNA:DNA hybrids are approximately 10° C. lower than those of DNA:RNA hybrids of the same length.

By standard conditions is meant, for example, depending on the nucleic acid in question temperatures between 42° C. and 58° C. in an aqueous buffer solution having a concentration of between 0.1 and 5×SSC (1×SSC=0.15 M NaCl, 15 mM sodium citrate, pH 7.2) or additionally in the presence of 50% formamide, such as by way of example 42° C. in 5×SSC, 50% formamide. Hybridization conditions for DNA:DNA hybrids are advantageously 0.1×SSC and temperatures between approximately 20° C. and 45° C., preferably between approximately 30° C. and 45° C. For DNA:RNA hybrids the hybridization conditions are advantageously 0.1× SSC and temperatures between approximately 30° C. and 55° C., preferably between approximately 45° C. and 55° C. These specified temperatures for hybridization are melting temperature values calculated by way of example for a nucleic acid having a length of approximately 100 nucleotides and a G+C content of 50% in the absence of formamide. The experimental conditions for DNA hybridization are described in relevant genetics textbooks such as by way of example Sambrook et al., "Molecular Cloning", Cold Spring Harbor Laboratory, 1989, and may be calculated by formulae known to those skilled in the art, for example as a function of the length of the nucleic acids, the nature of the hybrids or the G+C content. Those skilled in the art may draw on the following textbooks for further information on hybridization: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

Furthermore, by derivatives is meant homologues of the sequences SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23, for example eukaryotic homologues, truncated sequences, single-stranded DNA of the encoding and nonencoding DNA sequence or RNA of the encoding and nonencoding DNA sequence.

In addition, by homologues of the sequences SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 is meant derivatives such as by way of example promoter variants. These variants may be modified by one or more nucleotide exchanges, by insertion(s) and/or deletion(s) without, however, adversely affecting the functionality or efficiency of the promoters. Furthermore, the promoters can have their efficiency increased by altering there sequence or be completely replaced by more effective promoters even of foreign organisms.

By derivatives is also advantageously meant variants whose nucleotide sequence has been altered in the region from −1 to −2000 ahead of the start codon in such a way that the gene expression and/or the protein expression is modified, preferably increased. Furthermore, by derivatives is also meant variants, which have been modified at the 3' end.

The nucleic acid sequences according to the invention which encode a Δ-12-desaturase and Δ-15-desaturase, a Δ-9-elongase, Δ-8-desaturase and/or a Δ-5-desaturase may be produced by synthesis or obtained naturally or contain a mixture of synthetic and natural DNA components as well as consist of various heterologous Δ-12-desaturase and Δ-15-desaturase, Δ-9-elongase, Δ-8-desaturase and/or Δ-5-desaturase gene segments from different organisms. In general, synthetic nucleotide sequences are produced with codons, which are preferred by the corresponding host organisms, plants for example. This usually results in optimum expression of the heterologous gene. These codons preferred by plants may be determined from codons having the highest protein frequency, which are expressed in most of the plant species of interest. An example concerning the bacterium *Corynebacterium glutamicum* is provided in Wada et al. (1992) *Nucleic Acids Res.* 20:2111-2118). Such experiments can be carried out using standard methods and are known to the person skilled in the art.

Functionally equivalent sequences which encode the Δ-12-desaturase and Δ-15-desaturase, Δ-9-elongase, Δ-8-desaturase and/or Δ-5-desaturase gene are those derivatives of the sequence according to the invention which despite differing nucleotide sequence still possess the desired functions, that is to say the enzymatic activity and specific selectivity of the proteins. That means such functionally equivalent sequences have an biological or enzymatic activity, which is at least 10%, preferably at least 20%, 30%, 40% or 50% especially preferably at least 60%, 70%, 80% or 90% and very especially at least 91%, 92%, 93%, 94%, 95%, 96%, 97%, 98% or 99% or more of the activity of the proteins/enzymes encoded by the inventive sequences. Thus, functional equivalents include naturally occurring variants of the sequences described herein as well as artificial ones, e.g. artificial nucleotide sequences adapted to the codon use of a plant which have been obtained by chemical synthesis.

In addition, artificial DNA sequences are suitable, provided, as described above, they mediate the desired property, for example an increase in the content of Δ-12-, Δ-15-, Δ-8- and/or Δ-5-double bonds in fatty acids and an elongation of C18-fatty acids having a Δ-9-double bond in fatty acids, oils or lipids in plants that produce mature seeds preferably in crop plants by over expression of the Δ-12-desaturase and Δ-15-desaturase, Δ-9-elongase, Δ-8-desaturase and/or Δ-5-desaturase gene. Such artificial DNA sequences can exhibit Δ-12-desaturase and Δ-15-desaturase, Δ-9-elongase, Δ-8-desaturase and/or Δ-5-desaturase activity, for example by back-translation of proteins constructed by means of molecular modeling, or be determined by in vitro selection. Possible techniques for in vitro evolution of DNA to modify or improve the DNA sequences are described in Patten, P. A. et al., Current Opinion in Biotechnology 8, 724-733 (1997) or in Moore, J. C. et al., Journal of Molecular Biology 272, 336-347 (1997). Particularly suitable are encoding DNA sequences which are obtained by back-translation of a polypeptide sequence in accordance with the codon use specific to the host plant. Those skilled in the art familiar with the methods of plant genetics can easily determine the specific codon use by computer analyses of other known genes of the plant to be transformed.

Other suitable equivalent nucleic acid sequences, which may be mentioned are sequences that encode fusion proteins, a component of the fusion protein being a Δ-12-desaturase and Δ-15-desaturase, Δ-8-desaturase and/or Δ-5-desaturase polypeptide and/or a Δ-9 elongase polypeptide or a functionally equivalent part thereof. The second part of the fusion protein can be, for example, another polypeptide having enzymatic activity or an antigenic polypeptide sequence by means of which it is possible to demonstrate Δ-12-desaturase and Δ-15-desaturase, Δ-9-elongase, Δ-8-desaturase and/or Δ-5-desaturase expression (e.g. myc tag or his tag). Preferably, however, this is a regulatory protein sequence, such as by way of example a signal sequence for the endoplasmic reticulum (=ER) which directs the Δ-12-desaturase and Δ-15-desaturase, Δ-8-desaturase and/or Δ-5-desaturase protein and/or the Δ-9-elongase protein to the desired point of action, or regulatory sequences which influence the expression of the nucleic acid sequence according to the invention, such as promoters or terminators. In another preferred embodiment the second part of the fusion protein is a plastidial targeting sequence as described by Napier J. A. [Targeting of foreign proteins to the chloroplast, Methods Mol. Biol., 49, 1995: 369-376]. A preferred used vector comprising said plastidial targeting sequence is disclosed by Colin Lazarus [Guerineau F., Woolston S., Brooks L., Mullineaux P. "An expression cassette for targeting foreign proteins into chloroplast; Nucleic. Acids Res., December 9, 16 (23), 1988: 11380].

Advantageously, the Δ-12-desaturase and Δ-15-desaturase, Δ-9-elongase, Δ-8-desaturase and/or Δ-5-desaturase genes in the method according to the invention may be combined with other genes for fatty acid biosynthesis as described above. Examples of such genes are the acyl transferases, other desaturases or elongases such as Δ-4-desaturases or ω-3- and/or ω-6-specific desaturases) and/or such as Δ-5-elongases to mention only some of them. For in vivo and especially in vitro synthesis combination with e.g. NADH cytochrome B5 reductases, which can take up or release reduction equivalents is advantageous.

By the amino acid sequences according to the invention is meant proteins which contain an amino acid sequence depicted in the sequences SEQ ID NO: 4, SEQ ID NO: 6, SEQ ID NO: 8, SEQ ID NO: 12, SEQ ID NO: 16, SEQ ID NO: 18, SEQ ID NO: 20, SEQ ID NO: 22 or SEQ ID NO: 24 or a sequence obtainable there from by substitution, inversion, insertion or deletion of one or more amino acid groups (such sequences are derivatives of SEQ ID NO: 4, SEQ ID NO: 6, SEQ ID NO: 8, SEQ ID NO: 12, SEQ ID NO: 16, SEQ ID NO: 18, SEQ ID NO: 20, SEQ ID NO: 22 or SEQ ID NO: 24), whereas the enzymatic activities of the proteins depicted in SEQ ID NO: 4, SEQ ID NO: 6, SEQ ID NO: 8, SEQ ID NO: 12, SEQ ID NO: 16, SEQ ID NO: 18, SEQ ID NO: 20, SEQ ID NO: 22 or SEQ ID NO: 24 being retained or not substantially reduced, that is they still possess the same enzymatic specificity. By "not substantially reduced" or "the same enzymatic activity" is meant all enzymes which still exhibit at least 10%, 20%, 30%, 40% or 50%, preferably at least 60%, 70%, 80% or 90% particularly preferably at least 91%, 92%, 93%, 94%, 95%, 96%, 97%, 98%, 99% or more, of the enzymatic activity of the initial enzyme obtained from the wild type source organism such as organisms of the genus *Physcomitrella, Ceratodon, Borago, Thraustochytrium, Schizochytrium, Phytophtora, Mortierella, Caenorhabditis, Aleuritia, Muscariodides, Isochrysis, Phaeodactylum, Crypthecodinium, Acanthamoeba* or *Euglena* preferred source organisms are organisms such as the species *Euglena gracilis, Isochrysis galbana, Phaeodactylum tricornutum, Caenorhabditis elegans, Thraustochytrium, Phytophtora infestans, Ceratodon purpureus, Isochrysis galbana, Aleuritia farinosa, Muscariodides vialii, Mortierella alpina, Borago officinalis* or *Physcomitrella patens*. For the estimation of an enzymatic activity, which is "not substantially reduced" or which has the "same enzymatic activity" the enzymatic activity of the derived sequences are determined and compared with the wild type enzyme activities. In doing this, for example, certain amino acids may be replaced by others having similar physicochemical properties (space filling, basicity, hydrophobicity, etc.). For example, arginine residues are exchanged for lysine residues, valine residues for isoleucine residues or aspartic acid residues for glutamic acid residues. However, one or more amino acids may also be swapped in sequence, added or removed, or a plurality of these measures may be combined with one another.

By derivatives is also meant functional equivalents, which in particular also contain natural or artificial mutations of an originally isolated sequence encoding a Δ-12-desaturase and Δ-15-desaturase, a Δ-9-elongase, a Δ-8-desaturase and/or a Δ-5-desaturase, which continue to exhibit the desired function, that is the enzymatic activity and substrate selectivity thereof is not substantially reduced. Mutations comprise substitutions, additions, deletions, exchanges or insertions of one or more nucleotide residues. Thus, for example, the present invention also encompasses those nucleotide sequences, which are obtained by modification of the Δ-12-desaturase and Δ-15-desaturase nucleotide sequence, the Δ-8-desaturase nucleotide sequence, the Δ-5-desaturase nucleotide sequence and/or the Δ-9-elongase nucleotide sequence used in the inventive processes. The aim of such a modification may be, e.g., to further bind the encoding sequence contained therein or also, e.g., to insert further restriction enzyme interfaces.

Functional equivalents also include those variants whose function by comparison as described above with the initial gene or gene fragment is weakened (=not substantially reduced) or reinforced (=enzyme activity higher than the activity of the initial enzyme, that is activity is higher than 100%, preferably higher than 110%, 120%, 130%, 140% or 150%, particularly preferably higher than 200% or more).

At the same time the nucleic acid sequence may, for example, advantageously be a DNA or cDNA sequence. Suitable encoding sequences for insertion into an expression cassette according to the invention include by way of example those which encode a Δ-12-desaturase and Δ-15-desaturase, a Δ-8-desaturase and/or a Δ-5-desaturase with the sequences described above and lend the host the ability to overproduce fatty acids, oils or lipids having double bonds in the Δ-12-, Δ-15-, Δ-8-position and Δ-5-position, it being advantageous when at the same time fatty acids having at least four double bonds are produced. These sequences may be of homologous or heterologous origin.

By the gene construct (=nucleic acid construct or fragment or expression cassette) according to the invention is meant the sequences specified in SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 or SEQ ID NO: 23 which result from the genetic code and/or derivatives thereof which are functionally linked with one or more regulation signals advantageously to increase the gene expression and which control the expression of the encoding sequence in the host cell. These regulatory sequences should allow the selective expression of the genes and the protein expression. Depending on the host plant this may mean, for example, that the gene is expressed and/or overexpressed only after induction or that it is expressed and/or overexpressed immediately. Examples of these regulatory sequences are sequences to which inductors or repressors bind and in this way regulate the expression of the nucleic acid. In addition to these new regulation sequences or instead of these sequences the natural regulation of these sequences ahead of the actual structural genes may still be present and optionally have been genetically modified so that natural regulation was switched off and the expression of the genes increased. However, the gene construct can also be built up more simply, that is no additional regulation signals have been inserted ahead of the nucleic acid sequence or derivatives thereof and the natural promoter with its regulation has not been removed. Instead of this the natural regulation sequence was mutated in such a way that no further regulation ensues and/or the gene expression is heightened. These modified promoters in the form of part sequences (=promoter containing parts of the nucleic acid sequences according to the invention) can also be brought on their own ahead of the natural gene to increase the activity. In addition, the gene construct may advantageously also contain one or more so-called enhancer sequences functionally linked to the promoter which allow enhanced expression of the nucleic acid sequence. At the 3' end of the DNA sequences additional advantageous sequences may also be inserted, such as further regulatory elements or terminators. The SEQ ID NO: 3, SEQ ID NO: 5, SEQ ID NO: 7, SEQ ID NO: 11, SEQ ID NO: 15, SEQ ID NO: 17, SEQ ID NO: 19, SEQ ID NO: 21 and/or SEQ ID NO: 23 gene may be present in one or more copies in the gene construct (=expression cassette).

As described above, the regulatory sequences or factors can preferably positively influence and so increase the gene expression of the introduced genes. Thus, reinforcement of the regulatory elements advantageously on the transcription level may be effected by using powerful transcription signals such as promoters and/or enhancers. However, in addition reinforcement of translation is also possible, for example by improving the stability of the mRNA.

Suitable promoters in the expression cassette are in principle all promoters which can control the expression of foreign genes in microorganisms like protozoa such as amoeba, ciliates, algae such as green, brown, red or blue algae such as Euglena, bacteria such as gram-positive or gram-negative bacteria, yeasts such as *Saccharomyces*, *Pichia* or *Schizosaccharomyces* or fungi such as *Mortierella*, *Thraustochytrium* or *Schizochytrium* or plants such as *Aleuritia*, advantageously in plants or fungi. Such microorganisms are generally used to clone the inventive genes and possible other genes of the fatty acid biosynthesis chain for the production of fatty acids according to the inventive process. Use is preferably made in particular of plant promoters or promoters derived from a plant virus. Advantageous regulation sequences for the method according to the invention are found for example in promoters such as cos, tac, trp, tet, trp-tet, lpp, lac, lpp-lac, lacI$^{q-}$, T7, T5, T3, gal, trc, ara, SP6, λ-$P_R$ or in λ-$P_L$ promoters which are employed advantageously in gram-negative bacteria. Other advantageous regulation sequences are found, for example, in the gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], SSU, OCS, lib4, STLS1, B33, nos (=Nopalin Synthase Promoter) or in the ubiquintin or phaseolin promoter. The expression cassette may also contain a chemically inducible promoter by means of which the expression of the exogenous Δ-12- and Δ-15-, Δ-8- and/or Δ-5-desaturase gene and/or the Δ-9-elongase gene in the microorganism and/or plant can be controlled advantageously in the plants at a particular time. Advantageous plant promoters of this type are by way of example the PRP1 promoter [Ward et al., Plant. Mol. Biol. 22 (1993), 361-366], a promoter inducible by benzenesulfonamide (EP 388 186), a promoter inducible by tetracycline [Gatz et al., (1992) Plant J. 2, 397-404], a promoter inducible by salicylic acid (WO 95/19443), a promoter inducible by abscisic acid (EP 335 528) and a promoter inducible by ethanol or cyclohexanone (WO 93/21334). Other examples of plant promoters, which can advantageously be used are the promoter of cytosolic FBPase from potato, the ST-LSI promoter from potato (Stockhaus et al., EMBO J. 8 (1989) 2445-245), the promoter of phosphoribosyl pyrophosphate amidotransferase from *Glycine max* (see also gene bank accession number U87999) or a nodiene-specific promoter as described in EP 249 676. Particularly advantageous are those plant promoters, which ensure expression in tissues or plant parts/organs in which fatty acid biosynthesis or the precursor stages thereof occurs, as in endosperm or in the developing embryo for example. Particularly noteworthy are advantageous promoters, which ensure seed-specific expression such as by way of example the USP promoter or derivatives thereof, the LEB4 promoter, the phaseolin promoter or the napin promoter. The particularly advantageous USP promoter cited according to the invention or its derivatives mediate very early gene expression in seed development [Baeumlein et al., Mol Gen Genet, 1991, 225 (3): 459-67]. Other advantageous seed-specific promoters which may be used for monocotylodonous or dicotylodonous plants are the promoters suitable for dicotylodons such as napin gene promoters, likewise cited by way of example, from oilseed rape (U.S. Pat. No. 5,608,152), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the leguminous B4 promoter (LeB4, Baeumlein et al., Plant J., 2, 2, 1992: 233-239) or promoters suitable for monocotylodons such as the promoters of the lpt2 or lpt1 gene in barley (WO 95/15389 and WO 95/23230) or the promoters of the barley hordeine gene, the rice glutelin gene, the rice oryzin gene, the rice prolamin gene, the wheat gliadin gene, the white glutelin gene, the corn zein gene, the oats glutelin gene, the sorghum kasirin gene or the rye secalin gene which are described in WO99/16890.

Furthermore, particularly preferred are those promoters, which ensure the expression in tissues or plant parts in which, for example, the biosynthesis of fatty acids, oils and lipids or the precursor stages thereof takes place. Particularly noteworthy are promoters, which ensure a seed-specific expression. Noteworthy are the promoter of the napin gene from oilseed rape (U.S. Pat. No. 5,608,152), the USP promoter from *Vicia faba* (USP=unknown seed protein, Baeumlein et al., Mol Gen Genet, 1991, 225 (3): 459-67), the promoter of the oleosin gene from *Arabidopsis* (WO 98/45461), the phaseolin promoter (U.S. Pat. No. 5,504,200) or the promoter of the legumin B4 gene (LeB4; Baeumlein et al., 1992, Plant Journal, 2 (2): 233-9). Other promoters to be mentioned are that of the lpt2 or lpt1 gene from barley (WO 95/15389 and WO 95/23230), which mediate seed-specific expression in monocotyledonous plants. Other advantageous seed specific promoters are promoters such as the promoters from rice, corn or wheat disclosed in WO 99/16890 or Amy32b, Amy6-6 or aleurain (U.S. Pat. No. 5,677,474), Bce4 (rape, U.S. Pat. No. 5,530,149), glycinin (soy bean, EP 571 741), phosphoenol pyruvat carboxylase (soy bean, JP 06/62870), ADR12-2 (soy bean, WO 98/08962), isocitratlyase (rape, U.S. Pat. No. 5,689,040) or β-amylase (barley, EP 781 849).

As described above, the expression construct (=gene construct, nucleic acid construct) may contain yet other genes, which are to be introduced into the microorganism or plant. These genes can be subject to separate regulation or be subject to the same regulation region as the Δ-12- and Δ-15- desaturase gene and/or the Δ-8- and/or Δ-5-desaturase gene and/or the Δ-9-elongase gene. These genes are by way of example other biosynthesis genes, advantageously for fatty acid biosynthesis, which allow increased synthesis. Examples which may be mentioned are the genes for example of the Δ-9-, Δ-4-desaturase, Δ-5-elongase, α-ketoacyl reductases, α-ketoacyl synthases, elongases or the various hydroxylases and acyl-ACP thioesterases. The desaturase and elongase genes are advantageously used in the nucleic acid construct.

In principle all natural promoters with their regulation sequences can be used like those named above for the expression cassette according to the invention and the method according to the invention. Over and above this, synthetic promoters may also advantageously be used.

In the preparation of an a gene construct various DNA fragments can be manipulated in order to obtain a nucleotide sequence, which usefully reads in the correct direction and is equipped with a correct reading raster. To connect the DNA fragments (=nucleic acids according to the invention) to one another adaptors or linkers may be attached to the fragments.

The promoter and the terminator regions can usefully be provided in the transcription direction with a linker or polylinker containing one or more restriction points for the insertion of this sequence. Generally, the linker has 1 to 10, mostly 1 to 8, preferably 2 to 6, restriction points. In general the size of the linker inside the regulatory region is less than 100 bp, frequently less than 60 bp, but at least 5 bp. The promoter may be native or homologous as well as foreign or heterologous to the host organism, for example to the host plant. In the 5'-3' transcription direction the expression cassette contains the promoter, a DNA sequence which encodes a Δ-12- and Δ-15-desaturase gene, a Δ-8-desaturase gene, a Δ-5-desaturase gene and/or a Δ-9-elongase gene and a region for transcription termination. Different termination regions can be exchanged for one another in any desired fashion.

Furthermore, manipulations, which provide suitable restriction interfaces or which remove excess DNA or restriction interfaces can be employed. Where insertions, deletions or substitutions, such as transitions and transversions, come into consideration, in vitro mutagenesis, primer repair, restriction or ligation may be used. In suitable manipulations such as restriction, chewing back or filling of overhangs for blunt ends complementary ends of the fragments can be provided for the ligation.

For an advantageous high expression the attachment of the specific ER retention signal SEKDEL inter alia can be of importance (Schouten, A. et al., Plant Mol. Biol. 30 (1996), 781-792). In this way the average expression level is tripled or even quadrupled. Other retention signals, which occur naturally in plant and animal proteins located in the ER may also be employed for the construction of the cassette. In another preferred embodiment a plastidial targeting sequence is used as described by Napier J. A. [Targeting of foreign proteins to the chloroplast, Methods Mol. Biol., 49, 1995: 369-376]. A preferred used vector comprising said plastidial targeting sequence is disclosed by Colin Lazarus [Guerineau F., Woolston S., Brooks L., Mullineaux P. "An expression cassette for targeting foreign proteins into chloroplast; Nucleic. Acids Res., December 9, 16 (23), 1988: 11380].

Preferred polyadenylation signals are plant polyadenylation signals, preferably those which substantially correspond to T-DNA polyadenylation signals from *Agrobacterium tumefaciens*, in particular gene 3 of the T-DNA (octopin synthase) of the Ti plasmid pTiACH5 (Gielen et al., EMBO J. 3 (1984), 835 et seq.) or corresponding functional equivalents.

An expression cassette/gene construct is produced by fusion of a suitable promoter with a suitable Δ-12- and Δ-15-desaturase DNA sequence, a suitable Δ-8- and/or Δ-5-desaturase DNA sequence and/or a suitable Δ-9-elongase DNA sequence together with a polyadenylation signal by common recombination and cloning techniques as described, for example, in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

The DNA sequences encoding the nucleic acid sequences used in the inventive processes such as the Δ-12- and Δ-15-desaturase from *Acanthamoeba castellanii* or *Perkinsus marinus*, Δ-8-desaturase from *Euglena gracilis, Acanthamoeba castellanii* or *Perkinsus marinus*, the Δ-9-elongase from *Isochrysis galbana* or *Acanthamoeba castellanii* and/or the Δ-5-desaturase for example from *Thraustrochytrium, Acanthamoeba castellanii* or *Perkinsus marinus* or other organisms such as *Caenorhabditis elegans, Mortierella alpina, Borage officinalis* or *Physcomitrella patens* contain all the sequence characteristics needed to achieve correct localization of the site of fatty acid, lipid or oil biosynthesis. Accordingly, no further targeting sequences are needed per se. However, such localization may be desirable and advantageous and hence artificially modified or reinforced so that such fusion constructs are also a preferred advantageous embodiment of the invention.

Particularly preferred are sequences, which ensure targeting in plastids. Under certain circumstances targeting into other compartments (reported in: Kermode, Crit. Rev. Plant Sci. 15, 4 (1996), 285-423) may also be desirable, e.g. into vacuoles, the mitochondrium, the endoplasmic reticulum (ER), peroxisomes, lipid structures or due to lack of corresponding operative sequences retention in the compartment of origin, the cytosol.

Advantageously, the nucleic acid sequences according to the invention or the gene construct together with at least one reporter gene are cloned into a gene construct, which is introduced into the organism via a vector or directly into the genome. This reporter gene should allow easy detection via a growth, fluorescence, chemical, bioluminescence or resistance assay or via a photometric measurement. Examples of reporter genes which may be mentioned are antibiotic- or herbicide-resistance genes, hydrolase genes, fluorescence protein genes, bioluminescence genes, sugar or nucleotide metabolic genes or biosynthesis genes such as the Ura3 gene, the Ilv2 gene, the luciferase gene, the β-galactosidase gene, the gfp gene, the 2-desoxyglucose-6-phosphate phosphatase gene, the β-glucuronidase gene, β-lactamase gene, the neomycin phosphotransferase gene, the hygromycin phosphotransferase gene or the BASTA (=gluphosinate-resistance) gene. These genes permit easy measurement and quantification of the transcription activity and hence of the expression of the genes. In this way genome positions may be identified which exhibit differing productivity.

In a preferred embodiment an gene construct comprises upstream, i.e. at the 5' end of the encoding sequence, a promoter and downstream, i.e. at the 3' end, a polyadenylation signal and optionally other regulatory elements which are operably linked to the intervening encoding sequence for Δ-12- and Δ-15-desaturase, Δ-8-desaturase, Δ-9-elongase and/or Δ-5-desaturase DNA sequence. By an operable linkage is meant the sequential arrangement of promoter, encoding sequence, terminator and optionally other regulatory elements in such a way that each of the regulatory elements can fulfill its function in the expression of the encoding sequence in due manner. The sequences preferred for operable linkage are targeting sequences for ensuring subcellular localization in plastids. However, targeting sequences for ensuring subcellular localization in the mitochondrium, in the endoplasmic reticulum (=ER), in the nucleus, in oil corpuscles or other compartments may also be employed as well as translation promoters such as the 5' lead sequence in tobacco mosaic virus (Gallie et al., Nucl. Acids Res. 15 (1987), 8693-8711).

An expression cassette/gene construct may, for example, contain a constitutive promoter or a tissue-specific promoter (preferably the USP or napin promoter) the gene to be expressed and the ER retention signal. For the ER retention signal the KDEL amino acid sequence (lysine, aspartic acid, glutamic acid, leucine) or the KKX amino acid sequence (lysine-lysine-X-stop, wherein X means every other known amino acid) is preferably employed.

For expression in a prokaryotic or eukaryotic host organism, for example a microorganism such as a fungus or a plant such as an oil crop the expression cassette is advantageously inserted into a vector such as by way of example a plasmid, a phage or other DNA which allows optimum expression of the genes in the host organism. Examples of suitable plasmids are: in *E. coli* pLG338, pACYC184, pBR series such as e.g. pBR322, pUC series such as pUC18 or pUC19, M113 mp series, pKC30, pRep4, pHS1, pHS2, pPLc236, pMBL24, pLG200, pUR290, pIN-III$^{113}$-B1, λgt11 or pBdCI; in *Streptomyces* pIJ101, pIJ364, pIJ702 or pIJ361; in *Bacillus* pUB110, pC194 or pBD214; in *Corynebacterium* pSA77 or pAJ667; in fungi pALS1, pIL2 or pBB116; other advantageous fungal vectors are described by Romanos, M. A. et al., [(1992) "Foreign gene expression in yeast: a review", *Yeast* 8: 423-488] and by van den Hondel, C. A. M. J. J. et al. [(1991) "Heterologous gene expression in filamentous fungi" as well as in More Gene Manipulations in Fungi [J. W. Bennet & L. L. Lasure, eds., pp. 396-428: Academic Press: San Diego] and in "Gene transfer systems and vector development for filamentous fungi" [van den Hondel, C. A. M. J. J. & Punt, P. J. (1991) in: Applied Molecular Genetics of Fungi, Peberdy, J. F. et al., eds., pp. 1-28, Cambridge University Press: Cambridge]. Examples of advantageous yeast promoters are 2 μM, pAG-1, YEp6, YEp13 or pEMBLYe23. Examples of algal or plant promoters are pLGV23, pGHlac$^+$, pBIN19, pAK2004, pVKH or pDH51 (see Schmidt, R. and Willmitzer, L., 1988). The vectors identified above or derivatives of the vectors identified above are a small selection of the possible plasmids. Further plasmids are well known to those skilled in the art and may be found, for example, in the book Cloning Vectors (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press), Ch. 6/7, pp. 71-119. Advantageous vectors are known as shuttle vectors or binary vectors which replicate in *E. coli* and *Agrobacterium*.

By vectors is meant with the exception of plasmids all other vectors known to those skilled in the art such as by way of example phages, viruses such as SV40, CMV, baculovirus, adenovirus, transposons, IS elements, phasmids, phagemids, cosmids, linear or circular DNA. These vectors can be replicated autonomously in the host organism or be chromosomally replicated, chromosomal replication being preferred.

In a further embodiment of the vector the gene construct according to the invention may also advantageously be introduced into the organisms in the form of a linear DNA and be integrated into the genome of the host organism by way of heterologous or homologous recombination. This linear DNA may be composed of a linearized plasmid or only of the expression cassette as vector or the nucleic acid sequences according to the invention.

In a further advantageous embodiment the nucleic acid sequence according to the invention can also be introduced into an organism on its own.

If in addition to the nucleic acid sequence according to the invention further genes are to be introduced into the organism, all together with a reporter gene in a single vector or each single gene with a reporter gene in a vector in each case can be introduced into the organism, whereby the different vectors can be introduced simultaneously or successively.

The vector advantageously contains at least one copy of the nucleic acid sequences according to the invention and/or the expression cassette (=gene construct) according to the invention.

By way of example the plant expression cassette can be installed in the pRT transformation vector ((a) Toepfer et al., 1993, Methods Enzymol., 217: 66-78; (b) Toepfer et al. 1987, Nucl. Acids. Res. 15: 5890 ff.).

Alternatively, a recombinant vector (=expression vector) can also be transcribed and translated in vitro, e.g. by using the T7 promoter and the T7 RNA polymerase.

Expression vectors employed in prokaryotes frequently make use of inducible systems with and without fusion proteins or fusion oligopeptides, wherein these fusions can ensue in both N-terminal and C-terminal manner or in other useful domains of a protein. Such fusion vectors usually have the following purposes: i.) to increase the RNA expression rate; ii.) to increase the achievable protein synthesis rate; iii.) to increase the solubility of the protein; iv.) or to simplify purification by means of a binding sequence usable for affinity chromatography. Proteolytic cleavage points are also frequently introduced via fusion proteins, which allow cleavage of a portion of the fusion protein and purification. Such recognition sequences for proteases are recognized, e.g. factor Xa, thrombin and enterokinase.

Typical advantageous fusion and expression vectors are pGEX [Pharmacia Biotech Inc; Smith, D. B. and Johnson, K. S. (1988) *Gene* 67: 31-40], pMAL (New England Biolabs, Beverly, Mass.) and pRIT5 (Pharmacia, Piscataway, N.J.) which contains glutathione S-transferase (GST), maltose binding protein or protein A.

Other examples of *E. coli* expression vectors are pTrc [Amann et al., (1988) *Gene* 69:301-315] and pET vectors [Studier et al., Gene Expression Technology: Methods in Enzymology 185, Academic Press, San Diego, Calif. (1990) 60-89; Stratagene, Amsterdam, The Netherlands].

Other advantageous vectors for use in yeast are pYepSec1 (Baldari, et al., (1987) *Embo J.* 6:229-234), pMFa (Kurjan and Herskowitz, (1982) *Cell* 30:933-943), pJRY88 (Schultz et al., (1987) *Gene* 54:113-123), and pYES derivatives (Invitrogen Corporation, San Diego, Calif.). Vectors for use in filamentous fungi are described in: van den Hondel, C. A. M. J. J. & Punt, P. J. (1991) "Gene transfer systems and vector development for filamentous fungi", in: Applied Molecular Genetics of Fungi, J. F. Peberdy, et al., eds., pp. 1-28, Cambridge University Press: Cambridge.

Alternatively, insect cell expression vectors can also be advantageously utilized, e.g. for expression in Sf 9 cells. These are e.g. the vectors of the pAc series (Smith et al. (1983) *Mol. Cell Biol.* 3:2156-2165) and the pVL series (Lucklow and Summers (1989) *Virology* 170:31-39).

Furthermore, plant cells or algal cells can advantageously be used for gene expression. Examples of plant expression vectors may be found in Becker, D., et al. (1992) "New plant binary vectors with selectable markers located proximal to the left border", *Plant Mol. Biol.* 20: 1195-1197 or in Bevan, M. W. (1984) "Binary *Agrobacterium* vectors for plant transformation", *Nucl. Acid. Res.* 12: 8711-8721.

The host plant (=transgenic plant) advantageously contains at least one copy of the nucleic acid according to the invention and/or of the gene construct according to the invention.

The introduction of the nucleic acids according to the invention, the gene construct or the vector into organisms, plants for example, can in principle be done by all of the methods known to those skilled in the art. The introduction of the nucleic acid sequences gives rise to recombinant or transgenic plants.

To introduce the nucleic acids used in the process, the latter are advantageously amplified and ligated in the known manner. Preferably, a procedure following the protocol for Pfu DNA polymerase or a Pfu/Taq DNA polymerase mixture is followed. The primers are selected taking into consideration the sequence to be amplified. The primers should advantageously be chosen in such a way that the amplificate comprises the entire codogenic sequence from the start codon to the stop codon. After the amplification, the amplificate is expediently analyzed. For example, a gel-electrophoretic separation can be carried out, which is followed by a quantitative and a qualitative analysis. Thereafter, the amplificate can be purified following a standard protocol (for example Qiagen). An aliquot of the purified amplificate is then available for the subsequent cloning step. Suitable cloning vectors are mentioned above and generally known to the skilled worker. These include, in particular, vectors which are capable of replication in microbial systems, that is to say mainly vectors which ensure efficient cloning in yeasts or fungi and which make possible the stable transformation of plants. Those, which must be mentioned, again herein in particular are various binary and cointegrated vector systems, which are suitable for the T-DNA-mediated transformation. Such vector systems are, as a rule, characterized in that they comprise at least the vir genes required for the *Agrobacterium*-mediated transformation and the T-DNA-delimiting sequences (T-DNA border). These vector systems advantageously also comprise further cis-regulatory regions such as promoters and terminator sequences and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, while a second one bears T-DNA, but no vir gene. Owing to this fact, the last-mentioned vectors are relatively small, easy to manipulate and to replicate both in *E. coli* and in *Agrobacterium*. These binary vectors include vectors from the series pBIB-HYG, pPZP, pBecks, pGreen. In accordance with the invention, Bin19, pBI101, pBinAR, pGPTV and pCAMBIA are used by preference. An overview of the binary vectors and their use is found in Hellens et al, Trends in Plant Science (2000) 5, 446-451. In order to prepare the vectors, the vectors can first be linearized with restriction endonuclease(s) and then modified enzymatically in a suitable manner. Thereafter, the vector is purified, and an aliquot is employed for the cloning step. In the cloning step, the enzymatically cleaved and, if appropriate, purified amplificate is cloned with vector fragments, which have been prepared in a similar manner, using ligase. In this context, a particular nucleic acid construct, or vector or plasmid construct, can have one or else more than one codogenic gene segment. The codogenic gene segments in these constructs are preferably linked operably with regulatory sequences. The regulatory sequences include, in particular, plant sequences such as the above-described promoters and terminator sequences. The constructs can advantageously be stably propagated in microorganisms, in particular in *E. coli* and *Agrobacterium tumefaciens*, under selective conditions and make possible the transfer of heterologous DNA into plants or microorganisms.

The nucleic acids used in the process, the inventive nucleic acids and gene constructs, can be introduced into organisms such as microorganisms or advantageously plants, advantageously using cloning vectors, and thus be used in the transformation of plants such as those which are published and cited in: Plant Molecular Biology and Biotechnology (CRC Press, Boca Raton, Fla.), Chapter 6/7, p. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225. Thus, the nucleic acids, the inventive nucleic acids and nucleic acid constructs, and/or vectors used in the process can be used for the recombinant modification of a broad spectrum of organisms, advantageously plants, so that the latter become better and/or more efficient PUFA and/or LCPUFA producers.

In the case of microorganisms, those skilled in the art can find appropriate methods for the introduction of the inventive nucleic acid sequences, the gene construct or the vector in the textbooks by Sambrook, J. et al. (1989) Molecular cloning: A laboratory manual, Cold Spring Harbor Laboratory Press, by F. M. Ausubel et al. (1994) Current protocols in molecular biology, John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Harbor Laboratory Press or Guthrie et al. Guide to Yeast Genetics and Molecular Biology, Methods in Enzymology, 1994, Academic Press.

The transfer of foreign genes into the genome of a plant is called transformation. In doing this the methods described for the transformation and regeneration of plants from plant tissues or plant cells are utilized for transient or stable transformation. Suitable methods are protoplast transformation by poly(ethylene glycol)-induced DNA uptake, the "biolistic" method using the gene cannon—referred to as the particle bombardment method, electroporation, the incubation of dry embryos in DNA solution, microinjection and gene transfer mediated by *Agrobacterium*. Said methods are described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, in particular of crop plants such as by way of example tobacco plants, for example by bathing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Agrobacteria transformed by an expression vector according to the invention may likewise be used in known manner for the transformation of plants such as test plants like *Arabidopsis* or crop plants such as cereal crops, corn, oats, rye, barley, wheat, soybean, rice, cotton, sugar beet, canola, sunflower, flax, hemp, potatoes, tobacco, tomatoes, carrots, paprika, oilseed rape, tapioca, cassava, arrowroot, *tagetes*, alfalfa, lettuce and the various tree, nut and vine species, in particular of oil-containing crop plants such as soybean, peanut, castor oil plant, sunflower, corn, cotton, flax (linseed), oilseed rape, poppy, mustard, sesame, almond, *macadamia*, olive, *calendula, punica*, hazel nut, avocado, pumpkin, walnut, laurel, pistachio, Orychophragmus, marigold, borage, primrose, canola, evening primrose, hemp, coconut, oil palm, safflower (*Carthamus tinctorius*), coffee or cocoa bean, e.g. by bathing bruised leaves or chopped leaves in an agrobacterial solution and then culturing them in suitable media. For the production of LCPUFAs, for example arachidonic acid and/or eicosapentaenoic acid, borage, linseed, sunflower, safflower, *Brassica napus, Brassica juncea, Camelina sativa* or *Orychophragmus* are advantageously suitable.

The genetically modified plant cells may be regenerated by all of the methods known to those skilled in the art. Appropriate methods can be found in the publications referred to above by S. D. Kung and R. Wu, Potrykus or Höfgen and Willmitzer.

Accordingly, a further aspect of the invention relates to transgenic organisms transformed by at least one nucleic acid sequence, expression cassette or vector according to the invention as well as cells, cell cultures, tissue, parts—such as, for example, leaves, roots, etc. in the case of plant organisms—or reproductive material derived from such organisms. The terms "host organism", "host cell", "recombinant (host) organism" and "transgenic (host) cell" are used here interchangeably. Of course these terms relate not only to the particular host organism or the particular target cell but also to the descendants or potential descendants of these organisms or cells. Since, due to mutation or environmental effects certain modifications may arise in successive generations, these descendants need not necessarily be identical with the parental cell but nevertheless are still encompassed by the term as used here.

Suitable organisms or host organisms for the nucleic acid, gene construct or vector according to the invention are advantageously in principle all plants, which are able to synthesize fatty acids, especially unsaturated fatty acids or are suitable for the expression of recombinant genes as described above. Further examples which may be mentioned are plants such as *Arabidopsis*, Asteraceae such as *Calendula* or crop plants such as soybean, peanut, castor oil plant, sunflower, corn, cotton, flax, oilseed rape, coconut, oil palm, safflower (*Carthamus tinctorius*) or cocoa bean, bacteria such as the genus *Escherichia*, yeasts such as the genus *Saccharomyces*. Preference is given to organisms which can naturally synthesize oils in relatively large quantities such as fungi like *Mortierella alpina, Pythium insidiosum* or plants such as soybean, oilseed rape, coconut, oil palm, safflower, flax, castor oil plant, *Calendula*, peanut, cocoa bean or sunflower, or yeasts such as *Saccharomyces cerevisiae* and particular preference is given to the family of the Brassicaceae such as oilseed rape, soybean, flax, sunflower, *Calendula, Mortierella* or *Saccharomyces cerevisiae*.

Further useful host cells are identified in: Goeddel, *Gene Expression Technology: Methods in Enzymology* 185, Academic Press, San Diego, Calif. (1990).

Usable expression strains, e.g. those exhibiting a relatively low protease activity, are described in: Gottesman, S., *Gene Expression Technology: Methods in Enzymology* 185, Academic Press, San Diego, Calif. (1990) 119-128.

A further object of the invention as described relates to the use of an expression cassette containing DNA sequences encoding a Δ-12- and Δ-15-desaturase, a Δ-9-elongase, a Δ-8-desaturase and/or a Δ-5-desaturase gene or DNA sequences hybridizing therewith for the transformation of plant cells, tissues or parts of plants. The aim of use is to increase the content of fatty acids, oils or lipids having an increased content of double bonds.

In doing so, depending on the choice of promoter, the Δ-12- and Δ-15-desaturase, the Δ-9-elongase, the Δ-8-desaturase and/or the Δ-5-desaturase gene can be expressed specifically in the leaves, in the seeds, the nodules, in roots, in the stem or other parts of the plant, preferably in leaves and/or seeds. Those transgenic plants overproducing fatty acids, oils or lipids according to the invention, the reproductive material thereof, together with the plant cells, tissues or parts thereof are a further object of the present invention.

The expression cassette or the nucleic acid sequences according to the invention containing a Δ-12- and Δ-15-desaturase, a Δ-9-elongase, a Δ-8-desaturase and/or a Δ-5-desaturase gene sequence can, moreover, also be employed for the transformation of the organisms identified by way of example above such as bacteria, cyanobacteria, yeasts, filamentous fungi, ciliates and algae with the objective of increasing the content of fatty acids, oils or lipids according to the invention.

Within the framework of the present invention is the increase of the content of fatty acids, oils or lipids possessing a higher amount of ω-3-fatty acids in comparison to ω-6-fatty acids such as eicosapentaenoic acid in comparison to arachidonic acid, due to functional over expression of the Δ-12- and Δ-15-desaturase, the Δ-9-elongase, the Δ-8-desaturase and/or the Δ-5-desaturase gene in the plant according to the invention, advantageously in the trans-genic oilseed plants according to the invention, by comparison with the non genetically modified initial plants at least for the duration of at least one plant generation.

The preferred locus of biosynthesis, of fatty acids, oils or lipids for example, is generally the seed or cell layers of the seed so that a seed-specific expression of the Δ-12- and Δ-15-desaturase, the Δ-9-elongase, the Δ-8-desaturase and/or the Δ-5-desaturase gene is appropriate. It is, however, obvious that the biosynthesis of fatty acids, oils or lipids need not be limited to the seed tissue but rather can also occur in tissue-specific manner in all other parts of the plant—in epidermis cells or in the nodules for example.

A constitutive expression of the exogenous Δ-12- and Δ-15-desaturase, Δ-9-elongase, Δ-8-desaturase and/or Δ-5-desaturase gene is, moreover, advantageous. On the other hand, however, an inducible expression may also appear desirable.

The efficiency of the expression of the Δ-12- and Δ-15-desaturase, the Δ-9-elongase, the Δ-8-desaturase and/or the Δ-5-desaturase gene can be determined, for example, in vitro by shoot meristem propagation. In addition, an expression of the Δ-12- and Δ-15-desaturase, the Δ-9-elongase, the Δ-8-desaturase and/or the Δ-5-desaturase gene modified in nature and level and its effect on fatty acid, oil or lipid biosynthesis performance can be tested on test plants in greenhouse trials.

An additional object of the invention comprises transgenic plants transformed by an expression cassette containing a Δ-12- and Δ-15-desaturase, a Δ-9-elongase, a Δ-8-desaturase and/or a Δ-5-desaturase gene sequence according to the invention or DNA sequences hybridizing therewith, as well as transgenic cells, tissue, parts and reproduction material of such plants. Particular preference is given in this case to transgenic crop plants such as by way of example barley, wheat, rye, oats, corn, soybean, rice, cotton, sugar beet, the family of the Brassicaceae such as oilseed rape and canola, sunflower, flax, hemp, thistle, potatoes, tobacco, tomatoes, tapioca, cassava, arrowroot, alfalfa, lettuce and the various tree, nut and vine species.

For the purposes of the invention plants are mono- and dicotyledonous plants that produce mature seeds.

A further refinement according to the invention are transgenic plants as described above which contain the nucleic acid sequences, the gene construct and/or vector of the invention.

The invention is explained in more detail by the following examples.

EXAMPLES

Example 1

General Cloning Methods

The cloning methods, such as by way of example restriction cleavages, agarose gel electrophoresis, purification of DNA fragments, transfer of nucleic acids to nitrocellulose and nylon membranes, linkage of DNA fragments, transformation of *Escherichia coli* cells, culture of bacteria and sequence analysis of recombinant DNA, were carried out as described in Sambrook et al. (1989) (Cold Spring Harbor Laboratory Press: ISBN 0-87969-309-6).

Example 2

Sequence Analysis of Recombinant DNA

Sequencing of recombinant DNA molecules was done using a laser fluorescence DNA sequencer from the ABI company by the method of Sanger (Sanger et al. (1977) Proc. Natl. Acad. Sci. USA 74, 5463-5467). Fragments resulting from a polymerase chain reaction were sequenced and checked to prevent polymerase errors in the constructs to be expressed.

Example 3

Cloning of the PUFA Specific Desaturases from *Acanthamoeba castellanii* (=SEQ ID NO: 3, 5, 15, 19 and 21)

*Acanthamoeba castellanii* (Eukaryota; Protista; Sarcomastigophora; Sarcodina; Rhizopodea; Lobosa) is an amoeba species, which is a common species in the soil. *Acanthamoeba castellanii* can grow vegetative over a broad temperature range (10 to 32° C.). *A. castellanii* is able to de novo synthesize linoleic acid and C20 n-6 fatty acids.

*A. castellanii* (ATTC 30010) was grown at 30° C. on a medium containing 0.75% (w/v) peptone, 1.5% (w/v) glucose and 0.75% (w/v) yeast extract according to the reference of Jones et al. [Temperature-induced membrane-lipid adaptation in *Acanthamoeba castellanii*. Biochem J. 1993, 290: 273-278]. The cell cultures were grown under shaking (200 U/min) and harvested with a centrifuge at 250×g, 5 min, 4° C., after they have reached a cell density of $5 \times 10^6$-$10^7$ (measured in a Fuchs-Rosenthal Haemozytometer).

The total mRNA was isolated from said harvested cells with the aid of the RNeasy plant mini Kit (Qiagen). cDNA was synthesized from the total mRNA with the SMART RACE cDNA amplification kit (Clontech) according to the instructions of the manufacturer.

For the isolation of new desaturase genes the following degenerated primers were used for the amplification:

Deg1:
(SEQ ID NO: 53)
5'-GGITGG(C/T/A)TIGGICA(T/C)GA(T/C)(GT)(CT)I(GT)(GC)ICA-3'

Deg2:
(SEQ ID NO: 54)
5'-GG(A/G)AA(TCGA)AG(A/G)TG(A/G)TG(T/C)TC(A/G/T)AT(T/C)TG-3'

The aforementioned primers were used for the amplification in combination with the 3'-adapter-primer of the SMART RACE cDNA amplification kit.

The following protocol was used for the amplification:
a) 2 min at 95° C.,
b) 30 sec at 94° C.
  30 sec at 55-72° C.
  2 min at 72° C.
  Number of cycles: 30
c) 10 min at 72° C.

PCR amplicons were cloned and sequenced according to the instructions of the manufacturer (pTOPO, Invitrogen). The sequence information was used for the production of full-length clones. For the cloning of the full-length clones 5'- and 3'-specific primers were synthesized. Said primers were used for the amplification in the SMART RACE cDNA amplification kit (Clontech) and the amplicons were cloned into the pTOPO vector (Invitrogen)

Three sequences were identified, which show low similarities to desaturase genes.

In addition according to [Zank et al. 2002, Plant Journal 31:255 268] sequence 9Ac (Δ-9-Elongase from Acanthamoeba, SEQ ID NO: 11) could be identified, which shows low similarities to elongase genes.

TABLE 1

*Acanthamoeba castellanii* desaturase sequences

| Gene | Nucleotide bp | SEQ ID NO: |
|---|---|---|
| 12Ac (Δ-12/Δ15-Desaturase from *Acanthamoeba*) | 1224 bp | 19, 21 |
| 8Ac (Δ-8-Desaturase from *Acanthamoeba*) | 1374 bp | 3, 5 |
| 5Ac (Δ-5-Desaturase from *Acanthamoeba*) | 1353 bp | 15 |

Example 4

Cloning of the PUFA Specific Desaturases from *Perkinsus marinus* (=SEQ ID NO: 7, 17 and 23)

*Perkinsus marinus*, which belongs to the Protista, is a parasite in seashells. *P. marinus* is able to synthesize LCPUFAs such as arachidonic acid (20:4). The LCPUFAs are produced according to the present work over the Δ-8-/Δ-5-fatty acid pathway (see FIG. 1).

*P. marinus* was grown at 28° C. as disclosed by La Peyre et al. (J: Eurkaryot. Microbiol. 1993, 40: 304-310).

The total mRNA was isolated from said harvested cells with the aid of the RNeasy plant mini Kit (Qiagen). cDNA was synthesized from the total mRNA with the SMART RACE cDNA amplification kit (Clontech) according to the instructions of the manufacturer.

For the isolation of new desaturase genes the following degenerated primers were used for the amplification:

Deg1:
(SEQ ID NO: 53)
5'-GGITGG(C/T/A)TIGGICA(T/C)GA(T/C)(GT)(CT)I(GT)(GC)ICA-3'

Deg2:
(SEQ ID NO: 54)
5'-GG(A/G)AA(TCGA)AG(A/G)TG(A/G)TG(T/C)TC(A/G/T)AT(T/C)TG-3'

The aforementioned primers were used for the amplification in combination with the 3'-adapter-primer of the SMART RACE cDNA amplification kit.

The following protocol was used for the amplification:
d) 2 min at 95° C.,
e) 30 sec at 94° C.
  30 sec at 55-72° C.
  2 min at 72° C.
  Number of cycles: 30
f) 10 min at 72° C.

PCR amplicons were cloned and sequenced according to the instructions of the manufacturer (pTOPO, Invitrogen). The sequence information was used for the production of full-length clones. For the cloning of the full-length clones 5'- and 3'-specific primers were synthesized. Said primers were used for the amplification in the SMART RACE cDNA amplification kit (Clontech) and the amplicons were cloned into the pTOPO vector (Invitrogen) Three sequences were identified, which show low similarities to desaturase genes.

TABLE 2

*Perkinsus marinus* desaturase sequences

| Gene | Nucleotide bp | SEQ ID NO: |
|---|---|---|
| 12Pm (Δ-12-Desaturase from *Perkinsus*) | 1254 bp | 23 |
| 8Pm (Δ-8-Desaturase from *Perkinsus*) | 1236 bp | 7 |
| 5Pm (Δ-5-Desaturase from *Perkinsus*) | 1374 bp | 17 |

Example 5

Cloning of Expression Plasmids for the Heterologous Expression of *A. castellanii* and *P. marinus* Genes in Yeasts For the heterologous expression in yeasts the respective sequences were PCR amplified and with the restriction enzymes KpnI-SacI the resulting sequences were cloned into the yeast vector pYES2 (Invitrogen). For the amplification specific primers (see table 3 below) were used. Only the open reading frames of the PUFA genes were amplified. In addition restriction cleavage sides were attached to the nucleic acid sequences. At the 5'-end a KpnI side and a so named Kozak sequence (Cell, 1986, 44: 283-292) was added. To the 3'-end a SacI side was attached.

TABLE 3

Primers for the amplification of the nucleic acid sequences of the desaturases

| Gen | bp | primer | SEQ ID NO: |
|---|---|---|---|
| 12Ac | 1224 | Fwd: GGTACCATGGCGATCACGACGACGCAGACAC | 25 |
| | | Rvs: GAGCTCCTAGTGGGCCTTGCCGTGCTTGATCTCC | 26 |
| 8Ac | 1374 | Fwd: GGTACCATGGTCCTCACAACCCCGGCCCTC | 27 |
| | | Rvs: GGAGCTCTCAGTTCTCAGCACCCATCTTC | 28 |
| 5Ac | 1353 | Fwd: GGTACCATGGCCACCGCATCTGCATC | 29 |
| | | Rvs: GGAGCTTTAGCCGTAGTAGGCCTCCTT | 30 |
| 9Ac | 891 | Fwd: GGTACCATGGCGGCTGCGACGGCGAC | 31 |
| | | Rvs: GGAGCTTTAGTCGTGCTTCCTCTTGGG | 32 |
| 12Pm | 1254 | Fwd: GGTACCATGACCCAAACTGAGGTCCA | 33 |
| | | Rvs: GGAGCTCTAACGAGAAGTGCGAGCGT | 34 |
| 8Pm | 1236 | Fwd: GGTACCATGTCTTCTCTTACCCTCTA | 35 |
| | | Rvs: GGAGCTCTATTCCACTATGGCAACAG | 36 |
| 5Pm | 1374 | Fwd: GGTACCATGACTACTTCAACCACTAC | 37 |
| | | Rvs: GGAGCTCTACCTAGCAAGCAATCTCT | 38 |

| Composition of the PCR mix (50 µl) | |
|---|---|
| 5.00 µL | Template cDNA |
| 5.00 µL | 10x Puffer (Advantage-Polymerase) + 25 mM MgCl$_2$ |
| 5.00 µL | 2 mM dNTP |
| 1.25 µL | each primer (10 pmol/µL of the 5'-ATG as well as of the 3'-stopp primer) |
| 0.50 µL | Advantage polymerase |

The Advantage polymerase from Clontech was employed.
PCR Protocol
Addition temperature: 1 min at 55° C.
Denaturing temperature: 1 min at 94° C.
Elongation temperature: 2 min at 72° C.
Number of cycles: 35

The PCR products and the vector pYES2 were incubated with the restriction enzymes KpnI and SacI for 1 h at 37° C. Afterwards a ligation reaction was done with the Rapid Ligation Kit (Roche) according to the instructions of the manufacturer. The reaction mixture was than used for the transformation of *E. coli* DH5α cells (Invitrogen) again according to the instructions of the manufacturer. Positive clones were identified with PCR (reaction scheme as described above).

The plasmid DNA was isolated (Qiagen Dneasy) and the resulting plasmids were checked by sequencing and transformed with the lithium acetate method into the *Saccharomyces* strain W303-1A. As a control the plasmid pYES2 (vector without insert) was transformed in parallel. The transformed yeasts were selected on complete minimal dropout uracil medium (CMdum) agar plates supplemented with 2% glucose, but without uracil.

To express the genes from *A. castellanii* and *P. marinus*, precultures consisting of in each case 5 ml of CMdum dropout uracil liquid medium supplemented with 2% (w/v) raffinose, but without uracil were initially inoculated with the selected transformants and incubated for 2 days at 30° C. and 200 rpm. Then, 5 ml of CMdum (without uracil) liquid medium supplemented with 2% of raffinose and 300 µM of various fatty acids were inoculated with the precultures to an OD$_{600}$ of 0.05. Expression was induced by the addition of 2% (w/v) of galactose. The cultures were incubated for a further 96 hours at 22° C.

Example 6

Cloning of Expression Plasmids for the Expression in Plants

To transform plants, a further transformation vector based on pBIN19-35S (Bevan M. (1984) Binary *Agrobacterium* vectors for plant transformation. Nucl. Acids Res. 18:203) was generated. To this end, BamHI-XbaI cleavage sites were inserted at the 5' and 3' end of the coding sequences, using PCR. The corresponding primer sequences were derived from the 5' and 3' regions of the respective nucleic acid sequence (see table 4).

TABLE 4

Primers for the expression in plants

| Gen | bp | primer | SEQ ID NO: |
|---|---|---|---|
| 12Ac | 1224 | Fwd: GGATCCACCATGGCGATCACGACGACGCAGACAC | 39 |
| | | Rvs: GGTCTAGACTAGTGGGCCTTGCCGTGCTTGATCTCC | 40 |
| 8Ac | 1374 | Fwd: GGATCCAGGATGGTCCTCACAACCCCGGCCCTC | 41 |
| | | Rvs: GGTCTAGATCAGTTCTCAGCACCCATCTTC | 42 |
| 5Ac | 1353 | Fwd: GGATCCATGGCCACCGCATCTGCATC | 43 |
| | | Rvs: GGTCTAGATTAGCCGTAGTAGGCCTCCTT | 44 |
| 9Ac | 891 | Fwd: GGATCCATGGCGGCTGCGACGGCGAC | 45 |
| | | Rvs: GGTCTAGATTAGTCGTGCTTCCTCTTGGG | 46 |
| 12Pm | 1254 | Fwd: GGATCCATGACCCAAACTGAGGTCCA | 47 |
| | | Rvs: GGTCTAGACTAACGAGAAGTGCGAGCGT | 48 |

TABLE 4-continued

Primers for the expression in plants

| Gen | bp | primer | SEQ ID NO: |
|---|---|---|---|
| 8Pm | 1236 | Fwd: GGATCCATGTCTTCTCTTACCCTCTA | 49 |
| | | Rvs: GGTCTAGACTATTCCACTATGGCAACAG | 50 |
| 5Pm | 1374 | Fwd: GGATCCATGACTACTTCAACCACTAC | 51 |
| | | Rvs: GGTCTAGACTACCTAGCAAGCAATCTCT | 52 |

Composition of the PCR Mix (50 µl):
5.00 µl template cDNA
5.00 µl 10× buffer (Advantage polymerase)+25 mM MgCl$_2$
5.00 µl 2 mM dNTP
1.25 µl of each primer (10 pmol/µl)
0.50 µl Advantage polymerase
The Advantage polymerase from Clontech was employed.
PCR Reaction Conditions:
Annealing temperature: 1 min 55° C.
Denaturation temperature: 1 min 94° C.
Elongation temperature: 2 min 72° C.
Number of cycles: 35

The PCR products as well as the vector pBin19-35S were incubated with the restriction enzymes BamHI and XbaI for 16 hours at 37° C. Afterwards a ligation reaction was done with the Rapid Ligation Kit (Roche) according to the instructions of the manufacturer. The reaction mixture was than used for the transformation of *E. coli* DH5α cells (Invitrogen) again according to the instructions of the manufacturer. Positive clones were identified with PCR (reaction scheme as described above) and the plasmid DNA was isolated (Qiagen Dneasy). The resulting plasmids were checked by sequencing and transformed by electroporation into *Agrobacterium tumefaciens* GC3101. Afterwards the transformants were plated on 2% YEB Medium agar plates with kanamycin. Kanamycin tolerant cells were picked and used for the transformation of *Arabidopsis thaliana*.

Example 7

Expression of *A. castellanii* and *P. marinus* Genes in Yeasts

Yeasts which had been transformed with the plasmids pYES2, pYES-12Ac, pYES-8Ac, pYES2-5Ac, pYES2-9Ac, pYES2-12Pm, pYES2-8Pm and pYES2-5Pm as described in Example 5 were analyzed as follows:

The yeast cells from the main cultures were harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove nonderivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis were as follows: the oven temperature was programmed from 50° C. to 250° C. with a rate of 5° C./min and finally 10 min at 250° C. (holding).

The signals were identified by comparing the retention times with corresponding fatty acid standards (Sigma). The methodology is described for example in Napier and Michaelson, 2001, Lipids. 36 (8):761-766; Sayanova et al., 2001, Journal of Experimental Botany. 52 (360):1581-1585, Sperling et al., 2001, Arch. Biochem. Biophys. 388 (2):293-298 and Michaelson et al., 1998, FEBS Letters. 439 (3):215-218.

Example 8

Functional Characterization of the Genes of *A. castellanii*

The substrate activity and specificity of the genes were determined after expression and after feeding various fatty acids. The substrate specificity of the desaturases after expressions in yeasts can be determined by feeding various different fatty acids. Specific examples for the determination of the specificity and activity are disclosed for example in WO 93/11245, WO 94/11516, WO 93/06712, U.S. Pat. No. 5,614, 393, U.S. Pat. No. 5,614,393, WO 96/21022, WO0021557 and WO 99/27111, Qiu et al. 2001, J. Biol. Chem. 276, 31561-31566 for Δ4-desaturases, Hong et al. 2002, Lipids 37, 863-868 for Δ5-desaturases. WO2005/012316 teaches such a method for example in example 18 in more detail.

a) Characterization of the Gene 12Ac:

First the construct pYES-12Ac was tested in yeasts without feeding fatty acids. Astonishingly it was shown in comparison to the control vector pYES2 (vector without insert) that even without feeding fatty acids new fatty acids are detectable in the yeasts (FIGS. 2 A and B).

FIGS. 2 A and B show a comparison of the fatty acid profile between the control (construct pYES2 without insert, FIG. 2A) and the construct pYES2-12Ac (FIG. 2B), which contains the *Acanthamoeba castellanii* gene for the Δ-12-/Δ-15-desaturase. The fatty acids are marked. The new fatty acids synthesized are in case of construct pYES2-12Ac (2B) the fatty acids C16:2, C16:3, C18:2 and C18:3, whereas the unusual fatty acids 16:2n-4 and 16:3n-1 are formed for the C16 fatty acids. For the C18 fatty acids linoleic and linolenic acid (18:2n-6 and 18:2n-3) are formed.

According to the new synthesized fatty acids it is possible to identify the gene product of the nucleic acid sequence as a Δ-12-desaturase. The enzyme is able to desaturate C18:1 and C16:1 as substrate to the corresponding C18:2 and C16:2 fatty acids. The conversion rate of C18:1 (40.0%) is higher than the rate of the C16:1 (15.8%) conversion. That means the conversion rate of C18:1 is more than double than the conversion rate of the C16:1.

The conversion rate of the desaturase was calculated according to the following formula:

$$\frac{\text{Substrate}}{(\text{Substrate} + \text{Product}) \times 100}$$

The result of the formula is given as percentage value.

Furthermore the enzyme shows in addition a clear Δ-15-desaturase-activity. That means also that products of the Δ-12-desaturase reaction, which are C16:2 and/or C18:2 are further desaturated to C16:3 and/or C18:3.

b) Characterization of the Gene 8Ac:

According to different sequence alignments (Blast) performed with the sequence SEQ ID NO: 3 (8Ac sequence) with different data bases (NCBI-BLAST: at ncbi.nlm.nih.gov/BLAST/) the encoded protein sequence is most likely a putative Δ-5-desaturase.

| Sequences with significant similarities | (bits) | Value |
|---|---|---|
| gi\|16033740\|gb\|AAL13311.1\|delta-5 fatty acid desaturase [P . . . | 176 | 1e−42 |
| gi\|50882495\|gb\|AAT85663.1\|polyunsaturated fatty acid delta . . . | 170 | 6e−41 |
| gi\|4150956\|dbj\|BAA37090.1\|delta 5 fatty acid desaturase [D . . . | 156 | 9e−37 |
| gi\|23894018\|emb\|CAD53323.1\|delta 5 fatty acid desaturase [. . . | 156 | 1e−36 |
| gi\|33466346\|gb\|AAQ19605.1\|delta-4 fatty acid desaturase [E . . . | 150 | 7e−35 |
| gi\|5263169\|dbj\|BAA81814.1\|fatty acid desaturase [Dictyoste . . . | 149 | 1e−34 |
| gi\|25956288\|gb\|AAN75707.1\|delta 4-desaturase [Thraustochyt . . . | 142 | 1e−32 |
| gi\|25956290\|gb\|AAN75708.1\|delta 4-desaturase [Thraustochyt . . . | 139 | 1e−31 |
| gi\|25956294\|gb\|AAN75710.1\|delta 4-desaturase [Thraustochyt . . . | 139 | 1e−31 |
| gi\|25956292\|gb\|AAN75709.1\|delta 4-desaturase [Thraustochyt . . . | 138 | 2e−31 |
| gi\|20069125\|gb\|AAM09688.1\|delta-4 fatty acid desaturase [T . . . | 138 | 3e−31 |
| gi\|39545945\|gb\|AAR28035.1\|delta-5 desaturase [Mortierella . . . | 136 | 9e−31 |
| gi\|3859488\|gb\|AAC72755.1\|delta-5 fatty acid desaturase [Mo . . . | 135 | 2e−30 |
| gi\|41017070\|sp\|O74212\|FAD5_MORAP Delta-5 fatty acid desatur . . . | 130 | 7e−29 |
| gi\|48854274\|ref\|ZP_00308437.1\|COG3239: Fatty acid desatura . . . | 114 | 4e−24 |
| gi\|48854276\|ref\|ZP_00308439.1\|COG3239: Fatty acid desatura . . . | 114 | 7e−24 |

According to this putative activity different fatty acids were fed (18:2, 18:3, 20:3n-6, 20:4n-3). None of said fatty acids were desaturated by the enzyme. This result clearly shows that the protein encoded by the 8Ac gene has neither a Δ-5-desaturase activity nor a Δ-6-desaturase activity.

Unexpectedly after feeding of the fatty acids 20:2n-6 and 20:3n-3 it could be shown, that the 8Ac sequence encodes a Δ-8-desaturase (see FIGS. 3 A, 3 B, 4 A and 4 B).

FIGS. 3 A and B shows the fatty acid profile of yeasts transformed with the construct pYES2 as control (FIG. 3 A) and pYES2-8Ac (FIG. 3 B) and fed with the fatty acid C20: $2^{\Delta 11,14}$. The respective fatty acids are market.

FIGS. 4 A and B shows the fatty acid profile of yeast transformed with the construct pYES2 (FIG. 4 A) as control and pYES2-8Ac (FIG. 4 B) and fed with the fatty acid C20: $3^{\Delta 11,14,17}$. The respective fatty acids are market.

The protein encoded by 8Ac sequence is therefore a Δ-8-desaturase. The conversion rates for the fatty acids C20:2 and C20:3 are 15.2% and 17.5% respectively. This is absolutely astonishing as the 8Ac sequence, which has some similarities to "front-end" desaturases, has a different conserved region of the characteristic Cyt b5 motif His-Pro-Gly-Gly (HPGG, SEQ ID NO: 55), which is necessary for building the Heme domain. In general mutations in said domain lead to depletion of the enzymatic activity (Sayanova et al. 1999, Plant Physiol 121 (2):641-646). The amino acid sequence of this new Δ-8-desaturase shows unexpected differences to known "front-end" desaturases. Instead of the HPGG motif this desaturase shows the motif HPAG (see SEQ ID NO: 3), which is due to an alanine in position 44 of the sequence. Sayanova et al. 1999, Plant Physiol 121 (2):641-646 has shown that such a change of the motif from HPPG to HPAG leads to inactive enzymes. Therefore the activity of the new Δ-8-desaturase is even more astonishing.

For the further improvement of the activity of the Δ-8-desaturase, the sequence of the enzyme was mutagenized. The following primer.

```
8AcMf
CAAGTACCACCCGGGCGGCAGCAGGGCCA    (SEQ ID NO: 56)
and

8AcMr
TGGCCCTGCTGCCGCCCGGGTGGTACTTG    (SEQ ID NO: 57)
``` were used together with the site directed mutagenesis Kit (Stratagene) for the mutagenesis according to the instructions of the manufacturer of the Δ-8-desaturase. The mutagenesis was afterwards checked by sequencing. Due to the mutagenesis the nucleotide sequences 124-CACCCGGCCGGC was changed to 124-CACCCGGGCGGC, which leads to a change from Alanine to Glycine in position 44 of the nucleic acid sequence shown in SEQ ID NO: 3. The resulting sequence is shown in SEQ ID NO: 5. As already described for the sequence of 8Ac the mutated sequence 8AcM was also cloned into the vector pYES2 and transformed into yeast. Yeast transformed either with the vector pYES-8Ac or pYES2-8AcM were grown and fed in parallel with different fatty acids (see table 5). The results of the feeding are shown in table 5. The mutated enzyme 8AcM shows in comparison to the wild type enzyme 8Ac an increased activity towards the fatty acid C20:2. This is a two fold increase of the activity. The mutation has no influence of the activity with the fatty acid C20:3 as substrate. This clearly shows that with the mutation the activity of the Δ-8-desaturase can be influenced in a very specific manner.

TABLE 5

Fatty acid conversion rate of yeasts transformed with pYES-8Ac or pYES2-8AcM

| Plasmid | Fatty acid C20:2 | Fatty acid C20:3 |
|---|---|---|
| pYES-8Ac | 15.2% | 17.5% |
| pYES2-8AcM | 30.0% | 17.2% |

The mutated Δ-8-desaturase 8AcM and its derivatives are especially useful alone or in combination with the Δ-12- and Δ-15-desaturase, the Δ-9-elongase and the Δ-5-desaturase for the synthesis of arachidonic acid.

c) Characterization of the Gene 5Pm:

The constructs pYES2 and pYES-5Pm were transformed into yeasts grown in parallel as described. Afterwards 250 μM of different fatty acids were fed. During this feeding experiments it can be shown that fatty acids such as C16:0, C16:1, C18:0, C18:1, C18:2n-6, C20:2n-6 or C22:4n-6 are not desaturated by the protein encoded by the 5Pm sequence. Whereas the substrate C20:3n-6 was desaturated by the enzyme (see FIGS. 5 A and 5 B). FIGS. 5 A and 5 B clearly shows that the enzyme produces arachidonic acid during the transformation of the fatty acid substrate C20:3n-6. No new fatty acid is produced by the control (FIG. 5 A). The desaturation of the fatty acid substrate C20:3n-6 to arachidonic acid is due to a Δ-5-desaturase activity, which is encoded by the 5Pm sequence (SEQ ID NO: 17). The conversion rate calculated according to the equation mentioned above is 15.4%.

FIGS. 5 A and 5 B shows the comparison of the fatty acid profile of yeasts transformed with the construct pYES2 as control and fed with the fatty acid C20:3n-6 (FIG. 5 A) and with the construct pYES2-5Pm fed with the fatty acid C20: 3n-6 (FIG. 5 B). The fatty acids are marked. The new synthesized fatty acid is C20:4n-6 (arachidonic acid).

d) Characterization of the Genes 5Ac, 9Ac, 12Pm and 8Pm:

According to sequence comparisons it was able to identify the sequences 5Ac, 12Pm and 8Pm as desaturases having a Δ-5-desaturase, Δ-12-desaturase and Δ-8-desaturase activity. For the sequence 9Ac we were able to show a Δ-9-elongase activity.

In combination with the 12Ac and 8Ac gene the complete set of enzymes from *A. castellanii*, which is necessary for the synthesis for arachidonic (C20:4n-6) or eicosapentaenoic acid could be identified. In addition further genes for the synthesis of said aforementioned fatty acids are isolated from *P. marinus*. With the aid of said genes the PUFA and/or LCPUFA content can be further improved. For the synthesis of arachidonic acid or eicosapentaenoic acid said genes can be introduced in plants or microorganism (see example 8).

Example 8

Generation of Transgenic Plants a) Generation of Transgenic Oilseed Rape Plants (Modified Method of Moloney et al., 1992, Plant Cell Reports, 8:238-242)

Binary vectors in *Agrobacterium tumefaciens* C58C1: pGV2260 or *Escherichia coli* (Deblaere et al, 1984, Nucl. Acids. Res. 13, 4777-4788) can be used for generating transgenic oilseed rape plants. To transform oilseed rape plants (Var. *Drakkar*, NPZ Nordeutsche Pflanzenzucht, Hohenlieth, Germany), a 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) is used. Petiols or hypocotyls of freshly germinated sterile oilseed rape plants (in each case approx. 1 cm$^2$) are incubated with a 1:50 agrobacterial dilution for 5-10 minutes in a Petri dish. This is followed by 3 days of coincubation in the dark at 25° C. on 3MS medium supplemented with 0.8% Bacto agar. The cultures are then grown for 3 days at 16 hours light/8 hours dark and the cultivation is continued in a weekly rhythm on MS medium supplemented with 500 mg/l Claforan (cefotaxim sodium), 50 mg/l kanamycin, 20 μM benzylaminopurine (BAP), now supplemented with 1.6 g/l of glucose. Growing shoots are transferred to MS medium supplemented with 2% sucrose, 250 mg/l Claforan and 0.8% Bacto agar. If no roots develop after three weeks, 2-indolebutyric acid was added to the medium as growth hormone for rooting.

Regenerated shoots are obtained on 2MS medium supplemented with kanamycin and Claforan; after rooting, they are transferred to compost and, after growing on for two weeks in a controlled-environment cabinet or in the greenhouse, allowed to flower, and mature seeds are harvested and analyzed by lipid analysis for elongase and/or desaturase expression, such as Δ-12- and Δ-15-desaturase, Δ-8-desaturase, Δ-9-elongase or Δ-5-desaturase activity. In this manner, lines with elevated contents of PUFAs and/or LCPUFAs can be identified.

b) Generation of Transgenic Linseed Plants

Transgenic linseed plants can be generated for example by the method of Bell et al., 1999, In Vitro Cell. Dev. Biol.-Plant. 35 (6):456-465 by means of particle bombardment. In general, linseed was transformed by an agrobacteria-mediated transformation, for example by the method of Mlynarova et al. (1994), Plant Cell Report 13: 282-285.

c) Generation of Transgenic *Arabidopsis* Plants

Binary plasmids were transferred to *A. tumefaciens* strain GV3101 by electroporation and kanamycin-resistant colonies were selected in all cases. Wildtype Col0 or trans-genic line CA1-9, containing the coding region of *I. galbana* elongating activity, IgASE1 [Qi, B., Beaudoin, F., Fraser, T., Stobart, A. K., Napier, J. A. and Lazarus, C. M. (2002) Identification of a cDNA encoding a novel C18-D9 polyunsaturated fatty acid-specific elongating activity from the docosahexaenoic acid (DHA)-producing microalga, *Isochrysis galbana*. FEBS Lett. 510, 159-65] was used as the host for transformation with *A. castellanii* Δ$^8$ desaturase gene. *A. tumefaciens*-mediated transformation was performed as described in Bechthold et al. [(1993) In planta *Agrobacterium*-mediated gene transfer by infiltration of *Arabidopsis thaliana* plants. C.R. Acad. Sci. Ser. III Sci. Vie., 316, 1194-1199.] and seeds from dipped plants were spread on Murashige and Skoog medium containing 50 μg ml$^{-1}$ kanamycin.

Example 9

Lipid Extraction from Leafs

The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the elevated production of desired product (i.e. of the lipids or a fatty acid). These analytical techniques are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

In addition to the abovementioned processes, plant lipids are extracted from plant material as described by Cahoon et al. (1999) Proc. Natl. Acad. Sci. USA 96 (22):12935-12940 and Browse et al. (1986) Analytic Biochemistry 152:141-145. The qualitative and quantitative analysis of lipids or fatty acids is described by Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research, Oxford: Pergamon Press, 1 (1952)-16 (1977) under the title: Progress in the Chemistry of Fats and Other Lipids CODEN.

One example is the analysis of fatty acids (abbreviations: FAME, fatty acid methyl ester; GC-MS, gas liquid chromatography/mass spectrometry; TAG, triacylglycerol; TLC, thin-layer chromatography).

The unambiguous detection for the presence of fatty acid products can be obtained by analyzing recombinant organisms using analytical standard methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometric methods], Lipide 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 µm, 0.32 mm) at a temperature gradient of between 170° C. and 240° C. for 20 minutes and 5 minutes at 240° C. The identity of the resulting fatty acid methyl esters must be defined using standards, which are available from commercial sources (i.e. Sigma).

Plant material is initially homogenized mechanically by comminuting in a pestle and mortar to make it more amenable to extraction.

This is followed by heating at 100° C. for 10 minutes and, after cooling on ice, by resedimentation. The cell sediment is hydrolyzed for one hour at 90° C. with 1 M methanolic sulfuric acid and 2% dimethoxypropane, and the lipids are transmethylated. The resulting fatty acid methyl esters (FAMEs) are extracted in petroleum ether. The extracted FAMEs are analyzed by gas liquid chromatography using a capillary column (Chrompack, WCOT Fused Silica, CP-Wax-52 CB, 25 m, 0.32 mm) and a temperature gradient of from 170° C. to 240° C. in 20 minutes and 5 minutes at 240° C. The identity of the fatty acid methyl esters is confirmed by comparison with corresponding FAME standards (Sigma). The identity and position of the double bond can be analyzed further by suitable chemical derivatization of the FAME mixtures, for example to give 4,4-dimethoxyoxazoline derivatives (Christie, 1998) by means of GC-MS.

Leaf material from transgenic *Arabidopsis thaliana* Col0 and supertransformants of transgenic line CA1-9 both transformed with the construct pBIN1935S-8Ac were analyzed ba gas chromatography of methyl ester derivates as described above. Identities were confirmed by GC-MS and co-migration with authentic standards. The conversion rates are shown in the following table 6:

TABLE 6

Conversion rate with AcD8 (delta-8-desaturase from *Acanthamoeba castellanii*) of different substrates

| fatty acids | % of total fatty acids | % conversion of substrate |
|---|---|---|
| $20:2^{\Delta 11, 14}$ | 1.1 | — |
| $20:3^{\Delta 8, 11, 14}$ | 1.9 | 63 |
| $20:2^{\Delta 11, 14, 17}$ | 1.3 | — |
| $20:2^{\Delta 8, 11, 14, 17}$ | 0.8 | 40 |

FIG. 6 shows the result with the line CA1-9. In the double transgenic *Arabidopsis* a clear activity of Ac8 can be shown by the conversion of the present $20:2^{\Delta 11,14}$ or $20:3^{\Delta 11,14,17}$ into $20:3^{\Delta 8,11,14}$ or $20:4^{\Delta 8,11,14,17}$, the precursors of arachidonic acid or eicosapentaenoic acid.

Additionally Acyl-CoA profiles were done from the *Arabidopsis* leaves of *Arabidopsis* wild type (FIG. 7 A), *Arabidopsis* Δ9elo (FIG. 7 B) and *Arabidopsis* Δ9eloΔ8des (FIG. 7 C) using the method of Larson et al. [Plant J. 2002 November; 32 (4):519-27]. Results from the measurements are shown in FIG. 7 and demonstrate again the functionality of 8Ac in plants.

EQUIVALENTS

Many equivalents of the specific embodiments according to the invention described herein can be identified or found by the skilled worker resorting simply to routine experiments. These equivalents are intended to be within the scope of the patent claims.

We claim:

1. A process for the production of arachidonic acid or eicosapentaenoic acid or arachidonic acid and eicosapentaenoic acid in transgenic plants that produce mature seeds with a content of at least 1% by weight of said compounds referred to the total lipid content of said organism which comprises:
   a) introducing at least one nucleic acid sequence in said transgenic plant, which encodes a polypeptide having a Δ-12-desaturase- and Δ-15-desaturase-activity, and
   b) introducing at least one second nucleic acid sequence in said transgenic plant, which encodes a polypeptide having a Δ-9-elongase-activity, and
   c) introducing at least one third nucleic acid sequence in said transgenic plant, which encodes a polypeptide having a Δ-8-desaturase-activity, and
   d) introducing at least one fourth nucleic acid sequence, which encodes a polypeptide having a Δ-5-desaturase-activity, and
   e) cultivating and harvesting of said transgenic plant,
   wherein the nucleic acid sequence which encodes a polypeptide having Δ-8-desaturase activity comprises a nucleic acid sequence selected from the group consisting of
      a) the nucleic acid sequence of SEQ ID NO: 3 or 5;
      b) a nucleic acid sequence encoding the polypeptide sequence of SEQ ID NO: 4 or 6; and
      c) a nucleic acid sequence encoding a polypeptide having Δ-8-desaturase activity and having at least 90% homology to the sequence of SEQ ID NO: 4 or 6.

2. The process of claim 1, wherein the nucleic acid sequence which encodes a polypeptide having Δ-12-desaturase and Δ-15-desaturase activity, Δ-9-elongase, or Δ-5-desaturase activity comprises a nucleic acid sequence selected from the group consisting of
   a) a nucleic acid sequence depicted in SEQ ID NO: 1, SEQ ID NO: 7, SEQ ID NO: 9, SEQ ID NO: 11, SEQ ID NO:13, SEQ ID NO: 15, SEQ ID NO: 17, SEQ ID NO: 19, SEQ ID NO: 21 and SEQ ID NO: 23, encoding a polypeptide sequence as depicted in SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24, and
   b) a nucleic acid sequence encoding a polypeptide having at least 50% homology to the sequence as depicted in SEQ ID NO: 2, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24 and which polypeptide has Δ-12-desaturase and Δ-15-desaturase activity, Δ-9-elongase, or Δ-5-desaturase activity.

3. The process of claim 1, wherein the transgenic plant is an oilseed plant.

4. The process of claim 1, wherein the transgenic plant that produces mature seeds is selected from the group consisting of the plant families of Anacardiaceae, Asteraceae, Apiaceae, Boraginaceae, Brassicaceae, Cannabaceae, Elaeagnaceae, Euphorbiaceae, Fabaceae, Geraniaceae, Gramineae, Juglandaceae, Leguminosae, Linaceae, Lythrarieae, Malvaceae, Onagraceae, Palmae, Poaceae, Rubiaceae, Scrophulariaceae, Solanaceae, Sterculiaceae, and Theaceae.

5. The process of claim 1, wherein the transgenic plant that produces mature seeds is selected from the group consisting of the plant genera of *Pistacia, Mangifera, Anacardium, Calendula, Carthamus, Centaurea, Cichorium, Cynara, Helianthus, Lactuca, Locusta, Tagetes, Valeriana, Borago, Daucus, Brassica, Camelina, Melanosinapis, Sinapis, Arabadopsis, Orychophragmus, Cannabis, Elaeagnus, Manihot, Janipha, Jatropha, Ricinus, Pisum, Albizia, Cathormion, Feuillea, Inga, Pithecolobium, Acacia, Mimosa, Medicajo, Glycine, Dolichos, Phaseolus, Pelargonium, Cocos, Oleum, Juglans, Wallia, Arachis, Linum, Punica, Gossypium, Camissonia, Oenothera, Elaeis, Hordeum, Secale, Avena, Sorghum, Andropogon, Holcus, Panicum, Oryza, Zea, Triticum, Coffea, Verbascum, Capsicum, Nicotiana, Solanum, Lycopersicon, Theobroma*, and *Camellia*.

6. The process of claim 1, wherein the transgenic plant is selected from the group consisting of rapeseed, poppy, mustard, hemp, castor bean, sesame, olive, calendula, punica, hazel nut, maize, almond, macadamia, cotton, avocado, pumpkin, walnut, laurel, pistachio, primrose, canola, evening primrose, oil palm, peanut, linseed, soybean, safflower, marigold, coffee, tobacco, cacao, sunflower, and borage.

7. The process of claim 1, wherein the arachidonic acid or eicosapentaenoic acid or arachidonic acid and eicosapentaenoic acid is isolated in the form of their oils, lipids, or free fatty acids.

8. The process of claim 1, wherein arachidonic acid and eicosapentaenoic acid is produced in at least a 1:2 ratio.

9. The process of claim 1, wherein the arachidonic acid and eicosapentaenoic acid are produced in a content of at least 5% by weight referred to the total lipid content.

10. The process of claim 1, wherein the Δ-12-desaturase- and Δ-15-desaturase used in the process desaturates C16 or C18-fatty acids having one double bond in the fatty acid chain or C16 and C18-fatty acids having one double bond in the fatty acid chain.

11. An isolated nucleic acid sequence comprising a nucleotide sequence which encodes a Δ-8-desaturase selected from the group consisting of
   a) a nucleic acid sequence depicted in SEQ ID NO: 3 or 5;
   b) a nucleic acid sequence encoding a polypeptide sequence as depicted in SEQ ID NO: 4 or 6; and
   c) a nucleic acid sequence encoding a polypeptide having at least 90% homology to the sequence as depicted in SEQ ID NO: 4 or 6 and which polypeptide has Δ-8-desaturase activity.

12. A gene construct comprising the isolated nucleic acid of claim 11, where the nucleic acid is functionally linked to one or more regulatory signals.

13. The gene construct of claim 12, whose gene expression is increased by the regulatory signals.

14. A vector comprising the gene construct of claim 13.

15. A vector comprising the nucleic acid of claim 11 or a gene construct comprising said nucleic acid wherein the nucleic acid is functionally linked to one or more regulatory sequence.

16. A transgenic plant comprising
   a) the nucleic acid of claim 11,
   b) a gene construct comprising said nucleic acid wherein the nucleic acid is functionally linked to one or more regulatory sequence, or
   c) a vector comprising said nucleic acid or said gene construct.

17. The transgenic plant of claim 16, wherein the plant is an oilseed plant.

18. A transgenic plant comprising the gene construct of claim 13 or a vector comprising the gene construct.

19. The process of claim 1, wherein the nucleic acid which encodes a polypeptide having Δ-8-desaturase activity comprises a nucleic acid sequence encoding a polypeptide having at least 95% homology to the sequence of SEQ ID NO: 4 or 6.

20. The process of claim 1, wherein the nucleic acid which encodes a polypeptide having Δ-8-desaturase activity comprises the nucleic acid sequence of SEQ ID NO: 3 or 5 or a nucleic acid sequence encoding the polypeptide sequence of SEQ ID NO: 4 or 6.

21. The isolated nucleic acid sequence of claim 11, wherein the nucleotide sequence comprises a nucleic acid sequence encoding a polypeptide having at least 95% homology to the sequence of SEQ ID NO: 4 or 6.

22. The isolated nucleic acid sequence of claim 11, wherein the nucleotide sequence comprises the nucleic acid sequence of SEQ ID NO: 3 or 5 or a nucleic acid sequence encoding the polypeptide sequence of SEQ ID NO: 4 or 6.

* * * * *

SEQUENCE LISTING

<160> NUMBER OF SEQ ID NOS: 57

<210> SEQ ID NO 1
<211> LENGTH: 1266
<212> TYPE: DNA
<213> ORGANISM: Euglena gracilis
<220> FEATURE:
<221> NAME/KEY: CDS
<222> LOCATION: (1)..(1266)
<223> OTHER INFORMATION: Delta-8-Desaturase

<400> SEQUENCE: 1

```
atg aag tca aag cgc caa gcg ctt ccc ctt aca att gat gga aca aca      48
Met Lys Ser Lys Arg Gln Ala Leu Pro Leu Thr Ile Asp Gly Thr Thr
1               5                   10                  15 tat gat gtg tct gcc tgg gtc aat ttc cac cct ggt ggt gcg gaa att      96
Tyr Asp Val Ser Ala Trp Val Asn Phe His Pro Gly Gly Ala Glu Ile
            20                  25                  30 ata gag aat tac caa gga agg gat gcc act gat gcc ttc atg gtt atg     144
```

|  |  |  |  |  |  |  |  |  |  |  |  |  |  |  |  |
|---|---|---|---|---|---|---|---|---|---|---|---|---|---|---|---|
| Ile | Glu | Asn | Tyr | Gln | Gly | Arg | Asp | Ala | Thr | Asp | Ala | Phe | Met | Val | Met |
|  |  | 35 |  |  |  | 40 |  |  |  | 45 |  |  |  |  |  |

| cac | tct | caa | gaa | gcc | ttc | gac | aag | ctc | aag | cgc | atg | ccc | aaa | atc | aat | 192 |
|---|---|---|---|---|---|---|---|---|---|---|---|---|---|---|---|---|
| His | Ser | Gln | Glu | Ala | Phe | Asp | Lys | Leu | Lys | Arg | Met | Pro | Lys | Ile | Asn |  |
|  | 50 |  |  |  | 55 |  |  |  |  | 60 |  |  |  |  |  |  |

| ccc | agt | tct | gag | ttg | cca | ccc | cag | gct | gca | gtg | aat | gaa | gct | caa | gag | 240 |
|---|---|---|---|---|---|---|---|---|---|---|---|---|---|---|---|---|
| Pro | Ser | Ser | Glu | Leu | Pro | Pro | Gln | Ala | Ala | Val | Asn | Glu | Ala | Gln | Glu |  |
| 65 |  |  |  |  | 70 |  |  |  |  | 75 |  |  |  |  | 80 |  |

| gat | ttc | cgg | aag | ctc | cga | gaa | gag | ttg | atc | gca | act | ggc | atg | ttt | gat | 288 |
|---|---|---|---|---|---|---|---|---|---|---|---|---|---|---|---|---|
| Asp | Phe | Arg | Lys | Leu | Arg | Glu | Glu | Leu | Ile | Ala | Thr | Gly | Met | Phe | Asp |  |
|  |  |  |  | 85 |  |  |  |  | 90 |  |  |  |  | 95 |  |  |

| gcc | tcc | ccc | ctc | tgg | tac | tca | tac | aaa | atc | agc | acc | aca | ctg | ggc | ctt | 336 |
|---|---|---|---|---|---|---|---|---|---|---|---|---|---|---|---|---|
| Ala | Ser | Pro | Leu | Trp | Tyr | Ser | Tyr | Lys | Ile | Ser | Thr | Thr | Leu | Gly | Leu |  |
|  |  |  | 100 |  |  |  |  | 105 |  |  |  |  | 110 |  |  |  |

| gga | gtg | ctg | ggt | tat | ttc | ctg | atg | gtt | cag | tat | cag | atg | tat | ttc | att | 384 |
|---|---|---|---|---|---|---|---|---|---|---|---|---|---|---|---|---|
| Gly | Val | Leu | Gly | Tyr | Phe | Leu | Met | Val | Gln | Tyr | Gln | Met | Tyr | Phe | Ile |  |
|  |  |  | 115 |  |  |  |  | 120 |  |  |  |  | 125 |  |  |  |

| ggg | gca | gtg | ttg | ctt | ggg | atg | cac | tat | caa | cag | atg | ggc | tgg | ctt | tct | 432 |
|---|---|---|---|---|---|---|---|---|---|---|---|---|---|---|---|---|
| Gly | Ala | Val | Leu | Leu | Gly | Met | His | Tyr | Gln | Gln | Met | Gly | Trp | Leu | Ser |  |
| 130 |  |  |  |  | 135 |  |  |  |  | 140 |  |  |  |  |  |  |

| cat | gac | att | tgc | cac | cac | cag | act | ttc | aag | aac | cgg | aac | tgg | aac | aac | 480 |
|---|---|---|---|---|---|---|---|---|---|---|---|---|---|---|---|---|
| His | Asp | Ile | Cys | His | His | Gln | Thr | Phe | Lys | Asn | Arg | Asn | Trp | Asn | Asn |  |
| 145 |  |  |  |  | 150 |  |  |  |  | 155 |  |  |  |  | 160 |  |

| ctc | gtg | gga | ctg | gta | ttt | ggc | aat | ggt | ctg | caa | ggt | ttt | tcc | gtg | aca | 528 |
|---|---|---|---|---|---|---|---|---|---|---|---|---|---|---|---|---|
| Leu | Val | Gly | Leu | Val | Phe | Gly | Asn | Gly | Leu | Gln | Gly | Phe | Ser | Val | Thr |  |
|  |  |  |  | 165 |  |  |  |  | 170 |  |  |  |  | 175 |  |  |

| tgc | tgg | aag | gac | aga | cac | aat | gca | cat | cat | tcg | gca | acc | aat | gtt | caa | 576 |
|---|---|---|---|---|---|---|---|---|---|---|---|---|---|---|---|---|
| Cys | Trp | Lys | Asp | Arg | His | Asn | Ala | His | His | Ser | Ala | Thr | Asn | Val | Gln |  |
|  |  |  | 180 |  |  |  |  | 185 |  |  |  |  | 190 |  |  |  |

| ggg | cac | gac | cct | gat | att | gac | aac | ctc | ccc | ctc | tta | gcc | tgg | tct | gag | 624 |
|---|---|---|---|---|---|---|---|---|---|---|---|---|---|---|---|---|
| Gly | His | Asp | Pro | Asp | Ile | Asp | Asn | Leu | Pro | Leu | Leu | Ala | Trp | Ser | Glu |  |
|  |  | 195 |  |  |  |  | 200 |  |  |  |  | 205 |  |  |  |  |

| gat | gac | gtc | aca | cgg | gcg | tca | ccg | att | tcc | cgc | aag | ctc | att | cag | ttc | 672 |
|---|---|---|---|---|---|---|---|---|---|---|---|---|---|---|---|---|
| Asp | Asp | Val | Thr | Arg | Ala | Ser | Pro | Ile | Ser | Arg | Lys | Leu | Ile | Gln | Phe |  |
| 210 |  |  |  |  | 215 |  |  |  |  | 220 |  |  |  |  |  |  |

| cag | cag | tat | tat | ttc | ttg | gtc | atc | tgt | atc | ttg | ttg | cgg | ttc | att | tgg | 720 |
|---|---|---|---|---|---|---|---|---|---|---|---|---|---|---|---|---|
| Gln | Gln | Tyr | Tyr | Phe | Leu | Val | Ile | Cys | Ile | Leu | Leu | Arg | Phe | Ile | Trp |  |
| 225 |  |  |  |  | 230 |  |  |  |  | 235 |  |  |  |  | 240 |  |

| tgt | ttc | cag | agc | gtg | ttg | acc | gtg | cgc | agt | ctg | aag | gac | aga | gat | aac | 768 |
|---|---|---|---|---|---|---|---|---|---|---|---|---|---|---|---|---|
| Cys | Phe | Gln | Ser | Val | Leu | Thr | Val | Arg | Ser | Leu | Lys | Asp | Arg | Asp | Asn |  |
|  |  |  |  | 245 |  |  |  |  | 250 |  |  |  |  | 255 |  |  |

| caa | ttc | tat | cgc | tct | cag | tat | aag | aag | gag | gcc | att | ggc | ctc | gcc | ctg | 816 |
|---|---|---|---|---|---|---|---|---|---|---|---|---|---|---|---|---|
| Gln | Phe | Tyr | Arg | Ser | Gln | Tyr | Lys | Lys | Glu | Ala | Ile | Gly | Leu | Ala | Leu |  |
|  |  |  | 260 |  |  |  |  | 265 |  |  |  |  | 270 |  |  |  |

| cat | tgg | aca | ttg | aag | gcc | ctg | ttc | cac | tta | ttc | ttt | atg | ccc | agc | atc | 864 |
|---|---|---|---|---|---|---|---|---|---|---|---|---|---|---|---|---|
| His | Trp | Thr | Leu | Lys | Ala | Leu | Phe | His | Leu | Phe | Phe | Met | Pro | Ser | Ile |  |
|  |  | 275 |  |  |  |  | 280 |  |  |  |  | 285 |  |  |  |  |

| ctc | aca | tcg | ctg | ttg | gta | ttt | ttc | gtt | tcg | gag | ctg | gtt | ggc | ggc | ttc | 912 |
|---|---|---|---|---|---|---|---|---|---|---|---|---|---|---|---|---|
| Leu | Thr | Ser | Leu | Leu | Val | Phe | Phe | Val | Ser | Glu | Leu | Val | Gly | Gly | Phe |  |
| 290 |  |  |  |  | 295 |  |  |  |  | 300 |  |  |  |  |  |  |

| ggc | att | gcg | atc | gtg | gtg | ttc | atg | aac | cac | tac | cca | ctg | gag | aag | atc | 960 |
|---|---|---|---|---|---|---|---|---|---|---|---|---|---|---|---|---|
| Gly | Ile | Ala | Ile | Val | Val | Phe | Met | Asn | His | Tyr | Pro | Leu | Glu | Lys | Ile |  |
| 305 |  |  |  |  | 310 |  |  |  |  | 315 |  |  |  |  | 320 |  |

| ggg | gac | tcg | gtc | tgg | gat | ggc | cat | gga | ttc | tcg | gtt | ggc | cag | atc | cat | 1008 |
|---|---|---|---|---|---|---|---|---|---|---|---|---|---|---|---|---|
| Gly | Asp | Ser | Val | Trp | Asp | Gly | His | Gly | Phe | Ser | Val | Gly | Gln | Ile | His |  |
|  |  |  | 325 |  |  |  |  | 330 |  |  |  |  | 335 |  |  |  |

| gag | acc | atg | aac | att | cgg | cga | ggg | att | atc | aca | gat | tgg | ttt | ttc | gga | 1056 |
|---|---|---|---|---|---|---|---|---|---|---|---|---|---|---|---|---|
| Glu | Thr | Met | Asn | Ile | Arg | Arg | Gly | Ile | Ile | Thr | Asp | Trp | Phe | Phe | Gly |  |
|  |  |  | 340 |  |  |  |  | 345 |  |  |  |  | 350 |  |  |  |

| ggc | ttg | aac | tac | cag | atc | gag | cac | cat | ttg | tgg | ccg | acc | ctc | cct | cgc | 1104 |
|---|---|---|---|---|---|---|---|---|---|---|---|---|---|---|---|---|

```
Gly Leu Asn Tyr Gln Ile Glu His His Leu Trp Pro Thr Leu Pro Arg
            355                 360                 365 cac aac ctg aca gcg gtt agc tac cag gtg gaa cag ctg tgc cag aag      1152
His Asn Leu Thr Ala Val Ser Tyr Gln Val Glu Gln Leu Cys Gln Lys
            370                 375                 380 cac aac ctg ccg tat cgg aac ccg ctg ccc cat gaa ggg ttg gtc atc      1200
His Asn Leu Pro Tyr Arg Asn Pro Leu Pro His Glu Gly Leu Val Ile
385                 390                 395                 400 ctg ctg cgc tat ctg gcg gtg ttc gcc cgg atg gcg gag aag caa ccc      1248
Leu Leu Arg Tyr Leu Ala Val Phe Ala Arg Met Ala Glu Lys Gln Pro
                405                 410                 415 gcg ggg aag gct cta taa                                              1266
Ala Gly Lys Ala Leu
                420

<210> SEQ ID NO 2
<211> LENGTH: 421
<212> TYPE: PRT
<213> ORGANISM: Euglena gracilis

<400> SEQUENCE: 2

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

Pro Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Cys Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Ala Leu Phe His Leu Phe Phe Met Pro Ser Ile
        275                 280                 285
```

```
Leu Thr Ser Leu Leu Val Phe Val Ser Glu Leu Val Gly Gly Phe
    290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
    370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 3
<211> LENGTH: 1374
<212> TYPE: DNA
<213> ORGANISM: Acanthamoeba castellanii
<220> FEATURE:
<221> NAME/KEY: CDS
<222> LOCATION: (1)..(1374)
<223> OTHER INFORMATION: Delta-8-Desaturase

<400> SEQUENCE: 3 atg gtc ctc aca acc ccg gcc ctc aac ctg aag aag gaa cga acg tcg      48
Met Val Leu Thr Thr Pro Ala Leu Asn Leu Lys Lys Glu Arg Thr Ser
1               5                   10                  15 ttc acc cag gag gag ctt tcc aag ctc tgg gtc ctt cac ggc cag gtg      96
Phe Thr Gln Glu Glu Leu Ser Lys Leu Trp Val Leu His Gly Gln Val
            20                  25                  30 tac gat ttc acc gac ttt gtc aag tac cac ccg gcc ggc agc agg gcc     144
Tyr Asp Phe Thr Asp Phe Val Lys Tyr His Pro Ala Gly Ser Arg Ala
        35                  40                  45 atc ctg ctc ggc cgt ggc cgt gat tgt acc gtg ctc ttc gag tcc tac     192
Ile Leu Leu Gly Arg Gly Arg Asp Cys Thr Val Leu Phe Glu Ser Tyr
    50                  55                  60 cac aca gtc ctg cct tcc gat gct ctt ctc gag aag tac cgc gtc tct     240
His Thr Val Leu Pro Ser Asp Ala Leu Leu Glu Lys Tyr Arg Val Ser
65                  70                  75                  80 gct ccc aac gcc aag ctc gag gag agc cgg tca gcc aag ctg ttc tcg     288
Ala Pro Asn Ala Lys Leu Glu Glu Ser Arg Ser Ala Lys Leu Phe Ser
                85                  90                  95 ttc gag gag ggt agc ttc tac cga acc ctc aag cag cga acg cgc gag     336
Phe Glu Glu Gly Ser Phe Tyr Arg Thr Leu Lys Gln Arg Thr Arg Glu
            100                 105                 110 tac ttc aag acc aac aac ctg agc acc aag gcc acc acg atg gag gtc     384
Tyr Phe Lys Thr Asn Asn Leu Ser Thr Lys Ala Thr Thr Met Glu Val
        115                 120                 125 atc tac ttc gtg gcc acc atc ctc agc atc tac ttc tgc acg tgg gcc     432
Ile Tyr Phe Val Ala Thr Ile Leu Ser Ile Tyr Phe Cys Thr Trp Ala
    130                 135                 140 gcc ttc gtg cag ggt tcc ctc atc gcc gct gtc ctt cac gga gtg ggc     480
Ala Phe Val Gln Gly Ser Leu Ile Ala Ala Val Leu His Gly Val Gly
145                 150                 155                 160
```

```
cgt gcg atc tgt atc ata caa ccg act cat gcg act tcg cac tac gcc     528
Arg Ala Ile Cys Ile Ile Gln Pro Thr His Ala Thr Ser His Tyr Ala
            165                 170                 175 atg ttc cgc tca gtg tgg ctc aac cag tgg gcc tac agg atc tcc atg     576
Met Phe Arg Ser Val Trp Leu Asn Gln Trp Ala Tyr Arg Ile Ser Met
        180                 185                 190 gcc gtc agc gga tcg tcg ccg gcc cag tgg acc acc aag cac gtc atc     624
Ala Val Ser Gly Ser Ser Pro Ala Gln Trp Thr Thr Lys His Val Ile
    195                 200                 205 aac cat cac gtc gag acc aac ctg tgc ccc acc gat gac gac acc atg     672
Asn His His Val Glu Thr Asn Leu Cys Pro Thr Asp Asp Asp Thr Met
210                 215                 220 tac ccc atc aag cgc atc ctg cac gag ttc cct cgt ctg ttc ttc cac     720
Tyr Pro Ile Lys Arg Ile Leu His Glu Phe Pro Arg Leu Phe Phe His
225                 230                 235                 240 aag tac cag cac atc tac atc tgg ctg gtg tac ccc tac acc acc atc     768
Lys Tyr Gln His Ile Tyr Ile Trp Leu Val Tyr Pro Tyr Thr Thr Ile
            245                 250                 255 ttg tgg cac ttc tcc aac ctg gcc aag ctc gcc ctc ggc gcc gct cgc     816
Leu Trp His Phe Ser Asn Leu Ala Lys Leu Ala Leu Gly Ala Ala Arg
        260                 265                 270 ggt cag atg tac gag ggt atc gcc aag gtg agc caa gag acc tcg ggt     864
Gly Gln Met Tyr Glu Gly Ile Ala Lys Val Ser Gln Glu Thr Ser Gly
    275                 280                 285 gac tgg gtg gag acg gcc atg acg ctg ttc ttc acg ttc tcc cgt         912
Asp Trp Val Glu Thr Ala Met Thr Leu Phe Phe Thr Phe Ser Arg
290                 295                 300 ctg ctg ctg ccc ttc ctg tgc ctg ccc ttc acc acg gcc gcc gcg gtg     960
Leu Leu Leu Pro Phe Leu Cys Leu Pro Phe Thr Thr Ala Ala Ala Val
305                 310                 315                 320 ttc ctg ctc tcc gag tgg acc tgc tcg acc tgg ttc gcg ctg cag ttc    1008
Phe Leu Leu Ser Glu Trp Thr Cys Ser Thr Trp Phe Ala Leu Gln Phe
            325                 330                 335 gcc gtg agc cac gag gtc gac gag tgc gtc gag cac gag aag tcg gtc    1056
Ala Val Ser His Glu Val Asp Glu Cys Val Glu His Glu Lys Ser Val
        340                 345                 350 ctc gac acc ctc aag gcc aac gag gcc aag ggc atc gtc aac cag ggc    1104
Leu Asp Thr Leu Lys Ala Asn Glu Ala Lys Gly Ile Val Asn Gln Gly
    355                 360                 365 ggc ctc gtc gac tgg ggc gcg cac cag gtt cgg gcc tcg cac aac tac    1152
Gly Leu Val Asp Trp Gly Ala His Gln Val Arg Ala Ser His Asn Tyr
370                 375                 380 tct gcc gac tcc ctg ctg tcg ctc cac ttc agc ggt ggc ctc aac ctt    1200
Ser Ala Asp Ser Leu Leu Ser Leu His Phe Ser Gly Gly Leu Asn Leu
385                 390                 395                 400 cag atc gag cac cac ctc ttc ccc tcc gtc cac tac act cac tac cct    1248
Gln Ile Glu His His Leu Phe Pro Ser Val His Tyr Thr His Tyr Pro
            405                 410                 415 gcc ccg tcc aag att gtg cag cag acg tgc aag gag ttc aac ttg ccc    1296
Ala Pro Ser Lys Ile Val Gln Gln Thr Cys Lys Glu Phe Asn Leu Pro
        420                 425                 430 tgc act ctg tcg ccg tcg atg atg ggt gcc gtg acc aag cac tac cac    1344
Cys Thr Leu Ser Pro Ser Met Met Gly Ala Val Thr Lys His Tyr His
    435                 440                 445 cag ctc aag aag atg ggt gct gag aac tga                            1374
Gln Leu Lys Lys Met Gly Ala Glu Asn
450                 455

<210> SEQ ID NO 4
<211> LENGTH: 457
<212> TYPE: PRT
```

<213> ORGANISM: Acanthamoeba castellanii

<400> SEQUENCE: 4

```
Met Val Leu Thr Thr Pro Ala Leu Asn Leu Lys Lys Glu Arg Thr Ser
1               5                   10                  15

Phe Thr Gln Glu Glu Leu Ser Lys Leu Trp Val Leu His Gly Gln Val
            20                  25                  30

Tyr Asp Phe Thr Asp Phe Val Lys Tyr His Pro Ala Gly Ser Arg Ala
        35                  40                  45

Ile Leu Leu Gly Arg Gly Arg Asp Cys Thr Val Leu Phe Glu Ser Tyr
    50                  55                  60

His Thr Val Leu Pro Ser Asp Ala Leu Leu Glu Lys Tyr Arg Val Ser
65                  70                  75                  80

Ala Pro Asn Ala Lys Leu Glu Glu Ser Arg Ser Ala Lys Leu Phe Ser
                85                  90                  95

Phe Glu Glu Gly Ser Phe Tyr Arg Thr Leu Lys Gln Arg Thr Arg Glu
            100                 105                 110

Tyr Phe Lys Thr Asn Asn Leu Ser Thr Lys Ala Thr Thr Met Glu Val
        115                 120                 125

Ile Tyr Phe Val Ala Thr Ile Leu Ser Ile Tyr Phe Cys Thr Trp Ala
    130                 135                 140

Ala Phe Val Gln Gly Ser Leu Ile Ala Ala Val Leu His Gly Val Gly
145                 150                 155                 160

Arg Ala Ile Cys Ile Ile Gln Pro Thr His Ala Thr Ser His Tyr Ala
                165                 170                 175

Met Phe Arg Ser Val Trp Leu Asn Gln Trp Ala Tyr Arg Ile Ser Met
            180                 185                 190

Ala Val Ser Gly Ser Ser Pro Ala Gln Trp Thr Thr Lys His Val Ile
        195                 200                 205

Asn His His Val Glu Thr Asn Leu Cys Pro Thr Asp Asp Asp Thr Met
    210                 215                 220

Tyr Pro Ile Lys Arg Ile Leu His Glu Phe Pro Arg Leu Phe Phe His
225                 230                 235                 240

Lys Tyr Gln His Ile Tyr Ile Trp Leu Val Tyr Pro Tyr Thr Thr Ile
                245                 250                 255

Leu Trp His Phe Ser Asn Leu Ala Lys Leu Ala Leu Gly Ala Ala Arg
            260                 265                 270

Gly Gln Met Tyr Glu Gly Ile Ala Lys Val Ser Gln Glu Thr Ser Gly
        275                 280                 285

Asp Trp Val Glu Thr Ala Met Thr Leu Phe Phe Thr Phe Ser Arg
    290                 295                 300

Leu Leu Leu Pro Phe Leu Cys Leu Pro Phe Thr Thr Ala Ala Ala Val
305                 310                 315                 320

Phe Leu Leu Ser Glu Trp Thr Cys Ser Thr Trp Phe Ala Leu Gln Phe
                325                 330                 335

Ala Val Ser His Glu Val Asp Glu Cys Val Glu His Glu Lys Ser Val
            340                 345                 350

Leu Asp Thr Leu Lys Ala Asn Glu Ala Lys Gly Ile Val Asn Gln Gly
        355                 360                 365

Gly Leu Val Asp Trp Gly Ala His Gln Val Arg Ala Ser His Asn Tyr
    370                 375                 380

Ser Ala Asp Ser Leu Leu Ser Leu His Phe Ser Gly Gly Leu Asn Leu
385                 390                 395                 400

Gln Ile Glu His His Leu Phe Pro Ser Val His Tyr Thr His Tyr Pro
```

```
                        405                 410                 415
Ala Pro Ser Lys Ile Val Gln Gln Thr Cys Lys Glu Phe Asn Leu Pro
            420                 425                 430

Cys Thr Leu Ser Pro Ser Met Met Gly Ala Val Thr Lys His Tyr His
        435                 440                 445

Gln Leu Lys Lys Met Gly Ala Glu Asn
    450                 455

<210> SEQ ID NO 5
<211> LENGTH: 1374
<212> TYPE: DNA
<213> ORGANISM: Acanthamoeba castellanii
<220> FEATURE:
<221> NAME/KEY: CDS
<222> LOCATION: (1)..(1374)
<223> OTHER INFORMATION: Delta-8-Desaturase

<400> SEQUENCE: 5 atg gtc ctc aca acc ccg gcc ctc aac ctg aag aag gaa cga acg tcg      48
Met Val Leu Thr Thr Pro Ala Leu Asn Leu Lys Lys Glu Arg Thr Ser
1               5                   10                  15 ttc acc cag gag gag ctt tcc aag ctc tgg gtc ctt cac ggc cag gtg      96
Phe Thr Gln Glu Glu Leu Ser Lys Leu Trp Val Leu His Gly Gln Val
                20                  25                  30 tac gat ttc acc gac ttt gtc aag tac cac ccg ggc ggc agc agg gcc     144
Tyr Asp Phe Thr Asp Phe Val Lys Tyr His Pro Gly Gly Ser Arg Ala
            35                  40                  45 atc ctg ctc ggc cgt ggc cgt gat tgt acc gtg ctc ttc gag tcc tac     192
Ile Leu Leu Gly Arg Gly Arg Asp Cys Thr Val Leu Phe Glu Ser Tyr
        50                  55                  60 cac aca gtc ctg cct tcc gat gct ctt ctc gag aag tac cgc gtc tct     240
His Thr Val Leu Pro Ser Asp Ala Leu Leu Glu Lys Tyr Arg Val Ser
65                  70                  75                  80 gct ccc aac gcc aag ctc gag gag agc cgg tca gcc aag ctg ttc tcg     288
Ala Pro Asn Ala Lys Leu Glu Glu Ser Arg Ser Ala Lys Leu Phe Ser
                85                  90                  95 ttc gag gag ggt agc ttc tac cga acc ctc aag cag cga acg cgc gag     336
Phe Glu Glu Gly Ser Phe Tyr Arg Thr Leu Lys Gln Arg Thr Arg Glu
                100                 105                 110 tac ttc aag acc aac aac ctg agc acc aag gcc acc acg atg gag gtc     384
Tyr Phe Lys Thr Asn Asn Leu Ser Thr Lys Ala Thr Thr Met Glu Val
            115                 120                 125 atc tac ttc gtg gcc acc atc ctc agc atc tac ttc tgc acg tgg gcc     432
Ile Tyr Phe Val Ala Thr Ile Leu Ser Ile Tyr Phe Cys Thr Trp Ala
        130                 135                 140 gcc ttc gtg cag ggt tcc ctc atc gcc gct gtc ctt cac gga gtg ggc     480
Ala Phe Val Gln Gly Ser Leu Ile Ala Ala Val Leu His Gly Val Gly
145                 150                 155                 160 cgt gcg atc tgt atc ata caa ccg act cat gcg act tcg cac tac gcc     528
Arg Ala Ile Cys Ile Ile Gln Pro Thr His Ala Thr Ser His Tyr Ala
                165                 170                 175 atg ttc cgc tca gtg tgg ctc aac cag tgg gcc tac agg atc tcc atg     576
Met Phe Arg Ser Val Trp Leu Asn Gln Trp Ala Tyr Arg Ile Ser Met
                180                 185                 190 gcc gtc agc gga tcg tcg ccg gcc cag tgg acc acc aag cac gtc atc     624
Ala Val Ser Gly Ser Ser Pro Ala Gln Trp Thr Thr Lys His Val Ile
            195                 200                 205 aac cat cac gtc gag acc aac ctg tgc ccc acc gat gac gac acc atg     672
Asn His His Val Glu Thr Asn Leu Cys Pro Thr Asp Asp Asp Thr Met
        210                 215                 220 tac ccc atc aag cgc atc ctg cac gag ttc cct cgt ctg ttc ttc cac     720
```

```
Tyr Pro Ile Lys Arg Ile Leu His Glu Phe Pro Arg Leu Phe Phe His
225                 230                 235                 240 aag tac cag cac atc tac atc tgg ctg gtg tac ccc tac acc acc atc    768
Lys Tyr Gln His Ile Tyr Ile Trp Leu Val Tyr Pro Tyr Thr Thr Ile
                245                 250                 255 ttg tgg cac ttc tcc aac ctg gcc aag ctc gcc ctc ggc gcc gct cgc    816
Leu Trp His Phe Ser Asn Leu Ala Lys Leu Ala Leu Gly Ala Ala Arg
            260                 265                 270 ggt cag atg tac gag ggt atc gcc aag gtg agc caa gag acc tcg ggt    864
Gly Gln Met Tyr Glu Gly Ile Ala Lys Val Ser Gln Glu Thr Ser Gly
        275                 280                 285 gac tgg gtg gag acg gcc atg acg ctg ttc ttc acg ttc tcc cgt        912
Asp Trp Val Glu Thr Ala Met Thr Leu Phe Phe Thr Phe Ser Arg
    290                 295                 300 ctg ctg ctg ccc ttc ctg tgc ctg ccc ttc acc acg gcc gcc gcg gtg    960
Leu Leu Leu Pro Phe Leu Cys Leu Pro Phe Thr Thr Ala Ala Ala Val
305                 310                 315                 320 ttc ctg ctc tcc gag tgg acc tgc tcg acc tgg ttc gcg ctg cag ttc   1008
Phe Leu Leu Ser Glu Trp Thr Cys Ser Thr Trp Phe Ala Leu Gln Phe
                325                 330                 335 gcc gtg agc cac gag gtc gac gag tgc gtc gag cac gag aag tcg gtc   1056
Ala Val Ser His Glu Val Asp Glu Cys Val Glu His Glu Lys Ser Val
            340                 345                 350 ctc gac acc ctc aag gcc aac gag gcc aag ggc atc gtc aac cag ggc   1104
Leu Asp Thr Leu Lys Ala Asn Glu Ala Lys Gly Ile Val Asn Gln Gly
        355                 360                 365 ggc ctc gtc gac tgg ggc gcg cac cag gtt cgg gcc tcg cac aac tac   1152
Gly Leu Val Asp Trp Gly Ala His Gln Val Arg Ala Ser His Asn Tyr
    370                 375                 380 tct gcc gac tcc ctg ctg tcg ctc cac ttc agc ggt ggc ctc aac ctt   1200
Ser Ala Asp Ser Leu Leu Ser Leu His Phe Ser Gly Gly Leu Asn Leu
385                 390                 395                 400 cag atc gag cac cac ctc ttc ccc tcc gtc cac tac act cac tac cct   1248
Gln Ile Glu His His Leu Phe Pro Ser Val His Tyr Thr His Tyr Pro
                405                 410                 415 gcc ccg tcc aag att gtg cag cag acg tgc aag gag ttc aac ttg ccc   1296
Ala Pro Ser Lys Ile Val Gln Gln Thr Cys Lys Glu Phe Asn Leu Pro
            420                 425                 430 tgc act ctg tcg ccg tcg atg atg ggt gcc gtg acc aag cac tac cac   1344
Cys Thr Leu Ser Pro Ser Met Met Gly Ala Val Thr Lys His Tyr His
        435                 440                 445 cag ctc aag aag atg ggt gct gag aac tga                           1374
Gln Leu Lys Lys Met Gly Ala Glu Asn
    450                 455

<210> SEQ ID NO 6
<211> LENGTH: 457
<212> TYPE: PRT
<213> ORGANISM: Acanthamoeba castellanii

<400> SEQUENCE: 6

Met Val Leu Thr Thr Pro Ala Leu Asn Leu Lys Lys Glu Arg Thr Ser
1               5                   10                  15

Phe Thr Gln Glu Glu Leu Ser Lys Leu Trp Val Leu His Gly Gln Val
            20                  25                  30

Tyr Asp Phe Thr Asp Phe Val Lys Tyr His Pro Gly Gly Ser Arg Ala
        35                  40                  45

Ile Leu Leu Gly Arg Gly Arg Asp Cys Thr Val Leu Phe Glu Ser Tyr
    50                  55                  60

His Thr Val Leu Pro Ser Asp Ala Leu Leu Glu Lys Tyr Arg Val Ser
```

```
            65                  70                  75                  80
Ala Pro Asn Ala Lys Leu Glu Glu Ser Arg Ser Ala Lys Leu Phe Ser
                        85                  90                  95

Phe Glu Glu Gly Ser Phe Tyr Arg Thr Leu Lys Gln Arg Thr Arg Glu
                100                 105                 110

Tyr Phe Lys Thr Asn Asn Leu Ser Thr Lys Ala Thr Met Glu Val
        115                 120                 125

Ile Tyr Phe Val Ala Thr Ile Leu Ser Ile Tyr Phe Cys Thr Trp Ala
130                 135                 140

Ala Phe Val Gln Gly Ser Leu Ile Ala Val Leu His Gly Val Gly
145                 150                 155                 160

Arg Ala Ile Cys Ile Ile Gln Pro Thr His Ala Thr Ser His Tyr Ala
                165                 170                 175

Met Phe Arg Ser Val Trp Leu Asn Gln Trp Ala Tyr Arg Ile Ser Met
                180                 185                 190

Ala Val Ser Gly Ser Ser Pro Ala Gln Trp Thr Thr Lys His Val Ile
                195                 200                 205

Asn His His Val Glu Thr Asn Leu Cys Pro Thr Asp Asp Asp Thr Met
        210                 215                 220

Tyr Pro Ile Lys Arg Ile Leu His Glu Phe Pro Arg Leu Phe Phe His
225                 230                 235                 240

Lys Tyr Gln His Ile Tyr Ile Trp Leu Val Tyr Pro Tyr Thr Thr Ile
                245                 250                 255

Leu Trp His Phe Ser Asn Leu Ala Lys Leu Ala Leu Gly Ala Ala Arg
                260                 265                 270

Gly Gln Met Tyr Glu Gly Ile Ala Lys Val Ser Gln Glu Thr Ser Gly
                275                 280                 285

Asp Trp Val Glu Thr Ala Met Thr Leu Phe Phe Thr Phe Ser Arg
        290                 295                 300

Leu Leu Leu Pro Phe Leu Cys Leu Pro Phe Thr Thr Ala Ala Ala Val
305                 310                 315                 320

Phe Leu Leu Ser Glu Trp Thr Cys Ser Thr Trp Phe Ala Leu Gln Phe
                325                 330                 335

Ala Val Ser His Glu Val Asp Glu Cys Val Glu His Glu Lys Ser Val
                340                 345                 350

Leu Asp Thr Leu Lys Ala Asn Glu Ala Lys Gly Ile Val Asn Gln Gly
                355                 360                 365

Gly Leu Val Asp Trp Gly Ala His Gln Val Arg Ala Ser His Asn Tyr
        370                 375                 380

Ser Ala Asp Ser Leu Leu Ser Leu His Phe Ser Gly Gly Leu Asn Leu
385                 390                 395                 400

Gln Ile Glu His His Leu Phe Pro Ser Val His Tyr Thr His Tyr Pro
                405                 410                 415

Ala Pro Ser Lys Ile Val Gln Thr Cys Lys Glu Phe Asn Leu Pro
                420                 425                 430

Cys Thr Leu Ser Pro Ser Met Met Gly Ala Val Thr Lys His Tyr His
                435                 440                 445

Gln Leu Lys Lys Met Gly Ala Glu Asn
        450                 455

<210> SEQ ID NO 7
<211> LENGTH: 1236
<212> TYPE: DNA
<213> ORGANISM: Perkinsus marinus
<220> FEATURE:
```

<221> NAME/KEY: CDS
<222> LOCATION: (1)..(1236)
<223> OTHER INFORMATION: Delta-8-Desaturase

<400> SEQUENCE: 7

```
atg tct tct ctt acc ctc tac aga ggc ccc ttt tcc cga atg gtg ctc      48
Met Ser Ser Leu Thr Leu Tyr Arg Gly Pro Phe Ser Arg Met Val Leu
1               5                   10                  15 cct cgt cag gaa atc tgc atc gat ggt cgc ata tac gat gtc act gag      96
Pro Arg Gln Glu Ile Cys Ile Asp Gly Arg Ile Tyr Asp Val Thr Glu
            20                  25                  30 ttc atc aat cgt cat cca ggt ggt aag att atc ctc ttc caa gtt ggt     144
Phe Ile Asn Arg His Pro Gly Gly Lys Ile Ile Leu Phe Gln Val Gly
        35                  40                  45 gct gat gcc act gat gct ttt cgt gag ttt cat gct ggc agt gag aag     192
Ala Asp Ala Thr Asp Ala Phe Arg Glu Phe His Ala Gly Ser Glu Lys
    50                  55                  60 gca gag aag atc ctc aaa acc cta cca tcc cgt gat gat gac ggt act     240
Ala Glu Lys Ile Leu Lys Thr Leu Pro Ser Arg Asp Asp Asp Gly Thr
65                  70                  75                  80 ttc ctt cct tca acc caa cgc tcc atc atg gat gat ttc aaa cgc cta     288
Phe Leu Pro Ser Thr Gln Arg Ser Ile Met Asp Asp Phe Lys Arg Leu
                85                  90                  95 aga gat gac ctc gtc agc aga ggt gtc ttc aag cca agc gtc atg cat     336
Arg Asp Asp Leu Val Ser Arg Gly Val Phe Lys Pro Ser Val Met His
            100                 105                 110 gtt gta tac cgc tgc ttg gaa gtc gtt gct ctc tat ctc att ggc ttc     384
Val Val Tyr Arg Cys Leu Glu Val Val Ala Leu Tyr Leu Ile Gly Phe
        115                 120                 125 tat ttg gct ctg tgc acc agt aat gtg tac gtt ggg tgt gct gta ctt     432
Tyr Leu Ala Leu Cys Thr Ser Asn Val Tyr Val Gly Cys Ala Val Leu
    130                 135                 140 ggt gta gct caa ggt cgt gct ggt tgg ttg atg cat gaa gga ggt cat     480
Gly Val Ala Gln Gly Arg Ala Gly Trp Leu Met His Glu Gly Gly His
145                 150                 155                 160 cac tct ctg act ggt aac tgg aaa gtt gac cag ttc ctc caa gaa cta     528
His Ser Leu Thr Gly Asn Trp Lys Val Asp Gln Phe Leu Gln Glu Leu
                165                 170                 175 ttt ttc ggc att ggt tgt ggt atg tca gct gcg tgg tgg cgc aat gca     576
Phe Phe Gly Ile Gly Cys Gly Met Ser Ala Ala Trp Trp Arg Asn Ala
            180                 185                 190 cac aac aag cat cac gct gct cct cag cat tta ggg aaa gat gtt gat     624
His Asn Lys His His Ala Ala Pro Gln His Leu Gly Lys Asp Val Asp
        195                 200                 205 ctc gag aca ttg cct ctg gtc gcc ttc aat aag gcc gta ctt cga ggc     672
Leu Glu Thr Leu Pro Leu Val Ala Phe Asn Lys Ala Val Leu Arg Gly
    210                 215                 220 cgt cta ccg tct gtc tgg atc aga tca caa gct gtg tgc ttt gca ccg     720
Arg Leu Pro Ser Val Trp Ile Arg Ser Gln Ala Val Cys Phe Ala Pro
225                 230                 235                 240 ata tca aca cta ctg gta tcg ttc ttt tgg caa ttc tac cta cac ccg     768
Ile Ser Thr Leu Leu Val Ser Phe Phe Trp Gln Phe Tyr Leu His Pro
                245                 250                 255 agg cat att att agg aca ggt cga cga atg gag tct ttc tgg cta ctc     816
Arg His Ile Ile Arg Thr Gly Arg Arg Met Glu Ser Phe Trp Leu Leu
            260                 265                 270 gta cgc tac tta gtt att gtg tac ctc ggg ttc agc tat gga ttg gta     864
Val Arg Tyr Leu Val Ile Val Tyr Leu Gly Phe Ser Tyr Gly Leu Val
        275                 280                 285 tcg gtc ttg tta tgt tac atc gca agt gtg cat gtt ggt ggt atg tac     912
Ser Val Leu Leu Cys Tyr Ile Ala Ser Val His Val Gly Gly Met Tyr
```

```
atc ttt gta cac ttc gct cta tca cat aca cat tta cct gtc att aac        960
Ile Phe Val His Phe Ala Leu Ser His Thr His Leu Pro Val Ile Asn
305                 310                 315                 320 cag cat ggt aga gct aac tgg ttg gaa tac gca tct aag cac aca gtt       1008
Gln His Gly Arg Ala Asn Trp Leu Glu Tyr Ala Ser Lys His Thr Val
                325                 330                 335 aat gtg tca act aac aat tat ttc gtc aca tgg ctc atg agt tat ttg       1056
Asn Val Ser Thr Asn Asn Tyr Phe Val Thr Trp Leu Met Ser Tyr Leu
            340                 345                 350 aat tat caa ata gag cat cat ctc ttc ccg tca tgt ccc cag ttt aga       1104
Asn Tyr Gln Ile Glu His His Leu Phe Pro Ser Cys Pro Gln Phe Arg
        355                 360                 365 ttc cct ggt tac gtc agt atg agg gtt cga gaa ttt ttt cat aag cat       1152
Phe Pro Gly Tyr Val Ser Met Arg Val Arg Glu Phe Phe His Lys His
370                 375                 380 gga ttg aag tat aac gag gtc ggc tat cta cat gca ctc aat ctc aca       1200
Gly Leu Lys Tyr Asn Glu Val Gly Tyr Leu His Ala Leu Asn Leu Thr
385                 390                 395                 400 ttt tca aat ctg gct gct gtt gcc ata gtg gaa tag                        1236
Phe Ser Asn Leu Ala Ala Val Ala Ile Val Glu
                405                 410
```

<210> SEQ ID NO 8
<211> LENGTH: 411
<212> TYPE: PRT
<213> ORGANISM: Perkinsus marinus

<400> SEQUENCE: 8

```
Met Ser Ser Leu Thr Leu Tyr Arg Gly Pro Phe Ser Arg Met Val Leu
1               5                   10                  15

Pro Arg Gln Glu Ile Cys Ile Asp Gly Arg Ile Tyr Asp Val Thr Glu
            20                  25                  30

Phe Ile Asn Arg His Pro Gly Gly Lys Ile Ile Leu Phe Gln Val Gly
        35                  40                  45

Ala Asp Ala Thr Asp Ala Phe Arg Glu Phe His Ala Gly Ser Glu Lys
    50                  55                  60

Ala Glu Lys Ile Leu Lys Thr Leu Pro Ser Arg Asp Asp Gly Thr
65                  70                  75                  80

Phe Leu Pro Ser Thr Gln Arg Ser Ile Met Asp Asp Phe Lys Arg Leu
                85                  90                  95

Arg Asp Asp Leu Val Ser Arg Gly Val Phe Lys Pro Ser Val Met His
            100                 105                 110

Val Val Tyr Arg Cys Leu Glu Val Ala Leu Tyr Leu Ile Gly Phe
        115                 120                 125

Tyr Leu Ala Leu Cys Thr Ser Asn Val Tyr Val Gly Cys Ala Val Leu
    130                 135                 140

Gly Val Ala Gln Gly Arg Ala Gly Trp Leu Met His Glu Gly Gly His
145                 150                 155                 160

His Ser Leu Thr Gly Asn Trp Lys Val Asp Gln Phe Leu Gln Glu Leu
                165                 170                 175

Phe Phe Gly Ile Gly Cys Gly Met Ser Ala Ala Trp Trp Arg Asn Ala
            180                 185                 190

His Asn Lys His His Ala Ala Pro Gln His Leu Gly Lys Asp Val Asp
        195                 200                 205

Leu Glu Thr Leu Pro Leu Val Ala Phe Asn Lys Ala Val Leu Arg Gly
    210                 215                 220
```

```
Arg Leu Pro Ser Val Trp Ile Arg Ser Gln Ala Val Cys Phe Ala Pro
225                 230                 235                 240

Ile Ser Thr Leu Leu Val Ser Phe Phe Trp Gln Phe Tyr Leu His Pro
            245                 250                 255

Arg His Ile Ile Arg Thr Gly Arg Arg Met Glu Ser Phe Trp Leu Leu
            260                 265                 270

Val Arg Tyr Leu Val Ile Val Tyr Leu Gly Phe Ser Tyr Gly Leu Val
        275                 280                 285

Ser Val Leu Leu Cys Tyr Ile Ala Ser Val His Val Gly Gly Met Tyr
    290                 295                 300

Ile Phe Val His Phe Ala Leu Ser His Thr His Leu Pro Val Ile Asn
305                 310                 315                 320

Gln His Gly Arg Ala Asn Trp Leu Glu Tyr Ala Ser Lys His Thr Val
                325                 330                 335

Asn Val Ser Thr Asn Asn Tyr Phe Val Thr Trp Leu Met Ser Tyr Leu
            340                 345                 350

Asn Tyr Gln Ile Glu His His Leu Phe Pro Ser Cys Pro Gln Phe Arg
        355                 360                 365

Phe Pro Gly Tyr Val Ser Met Arg Val Arg Glu Phe Phe His Lys His
    370                 375                 380

Gly Leu Lys Tyr Asn Glu Val Gly Tyr Leu His Ala Leu Asn Leu Thr
385                 390                 395                 400

Phe Ser Asn Leu Ala Ala Val Ala Ile Val Glu
                405                 410
```

```
<210> SEQ ID NO 9
<211> LENGTH: 777
<212> TYPE: DNA
<213> ORGANISM: Isochrysis galbana
<220> FEATURE:
<221> NAME/KEY: CDS
<222> LOCATION: (1)..(777)
<223> OTHER INFORMATION: Delta-9-Elongase

<400> SEQUENCE: 9 atg gcc ctc gca aac gac gcg gga gag cgc atc tgg gcg gct gtg acc      48
Met Ala Leu Ala Asn Asp Ala Gly Glu Arg Ile Trp Ala Ala Val Thr
1               5                   10                  15 gac ccg gaa atc ctc att ggc acc ttc tcg tac ttg cta ctc aaa ccg      96
Asp Pro Glu Ile Leu Ile Gly Thr Phe Ser Tyr Leu Leu Leu Lys Pro
            20                  25                  30 ctc ctc cgc aat tcc ggg ctg gtg gat gag aag aag ggc gca tac agg      144
Leu Leu Arg Asn Ser Gly Leu Val Asp Glu Lys Lys Gly Ala Tyr Arg
        35                  40                  45 acg tcc atg atc tgg tac aac gtt ctg ctg gcg ctc ttc tct gcg ctg      192
Thr Ser Met Ile Trp Tyr Asn Val Leu Leu Ala Leu Phe Ser Ala Leu
    50                  55                  60 agc ttc tac gtg acg gcg acc gcc ctc ggc tgg gac tat ggt acg ggc      240
Ser Phe Tyr Val Thr Ala Thr Ala Leu Gly Trp Asp Tyr Gly Thr Gly
65                  70                  75                  80 gcg tgg ctg cgc agg caa acc ggc gac aca ccg cag ccg ctc ttc cag      288
Ala Trp Leu Arg Arg Gln Thr Gly Asp Thr Pro Gln Pro Leu Phe Gln
                85                  90                  95 tgc ccg tcc ccg gtt tgg gac tcg aag ctc ttc aca tgg acc gcc aag      336
Cys Pro Ser Pro Val Trp Asp Ser Lys Leu Phe Thr Trp Thr Ala Lys
            100                 105                 110 gca ttc tat tac tcc aag tac gtg gag tac ctc gac acg gcc tgg ctg      384
Ala Phe Tyr Tyr Ser Lys Tyr Val Glu Tyr Leu Asp Thr Ala Trp Leu
        115                 120                 125
```

```
agg gtc tcc ttt ctc cag gcc ttc cac cac ttt ggc gcg ccg tgg gat    432
Arg Val Ser Phe Leu Gln Ala Phe His His Phe Gly Ala Pro Trp Asp
    130                 135                 140 gtg tac ctc ggc att cgg ctg cac aac gag ggc gta tgg atc ttc atg    480
Val Tyr Leu Gly Ile Arg Leu His Asn Glu Gly Val Trp Ile Phe Met
145                 150                 155                 160 ttt ttc aac tcg ttc att cac acc atc atg tac acc tac tac ggc ctc    528
Phe Phe Asn Ser Phe Ile His Thr Ile Met Tyr Thr Tyr Tyr Gly Leu
                165                 170                 175 acc gcc gcc ggg tat aag ttc aag gcc aag ccg ctc atc acc gcg atg    576
Thr Ala Ala Gly Tyr Lys Phe Lys Ala Lys Pro Leu Ile Thr Ala Met
            180                 185                 190 cag atc tgc cag ttc gtg ggc ggc ttc ctg ttg gtc tgg gac tac atc    624
Gln Ile Cys Gln Phe Val Gly Gly Phe Leu Leu Val Trp Asp Tyr Ile
        195                 200                 205 aac gtc ccc tgc ttc aac tcg gac aaa ggg aag ttg ttc agc tgg gct    672
Asn Val Pro Cys Phe Asn Ser Asp Lys Gly Lys Leu Phe Ser Trp Ala
    210                 215                 220 ttc aac tat gca tac gtc ggc tcg gtc ttc ctc ttc tgc cac ttt        720
Phe Asn Tyr Ala Tyr Val Gly Ser Val Phe Leu Phe Cys His Phe
225                 230                 235                 240 ttc tac cag gac aac ttg gca acg aag aaa tcg gcc aag gcg ggc aag    768
Phe Tyr Gln Asp Asn Leu Ala Thr Lys Lys Ser Ala Lys Ala Gly Lys
                245                 250                 255 cag ctc tag                                                         777
Gln Leu

<210> SEQ ID NO 10
<211> LENGTH: 258
<212> TYPE: PRT
<213> ORGANISM: Isochrysis galbana

<400> SEQUENCE: 10

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Lys Pro
                20                  25                  30

Leu Leu Arg Asn Ser Gly Leu Val Asp Glu Lys Lys Gly Ala Tyr Arg
            35                  40                  45

Thr Ser Met Ile Trp Tyr Asn Val Leu Leu Ala Leu Phe Ser Ala Leu
        50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Thr Ala Lys
                100                 105                 110

Ala Phe Tyr Tyr Ser Lys Tyr Val Glu Tyr Leu Asp Thr Ala Trp Leu
            115                 120                 125

Arg Val Ser Phe Leu Gln Ala Phe His His Phe Gly Ala Pro Trp Asp
        130                 135                 140

Val Tyr Leu Gly Ile Arg Leu His Asn Glu Gly Val Trp Ile Phe Met
145                 150                 155                 160

Phe Phe Asn Ser Phe Ile His Thr Ile Met Tyr Thr Tyr Tyr Gly Leu
                165                 170                 175

Thr Ala Ala Gly Tyr Lys Phe Lys Ala Lys Pro Leu Ile Thr Ala Met
            180                 185                 190

Gln Ile Cys Gln Phe Val Gly Gly Phe Leu Leu Val Trp Asp Tyr Ile
```

```
                   195                 200                 205
Asn Val Pro Cys Phe Asn Ser Asp Lys Gly Lys Leu Phe Ser Trp Ala
            210                 215                 220

Phe Asn Tyr Ala Tyr Val Gly Ser Val Phe Leu Leu Phe Cys His Phe
225                 230                 235                 240

Phe Tyr Gln Asp Asn Leu Ala Thr Lys Lys Ser Ala Lys Ala Gly Lys
                245                 250                 255

Gln Leu

<210> SEQ ID NO 11
<211> LENGTH: 891
<212> TYPE: DNA
<213> ORGANISM: Acanthamoeba castellanii
<220> FEATURE:
<221> NAME/KEY: CDS
<222> LOCATION: (1)..(891)
<223> OTHER INFORMATION: Delta-9-Elongase

<400> SEQUENCE: 11
```

| | | | | | | | | | | | | | | | | |
|---|---|---|---|---|---|---|---|---|---|---|---|---|---|---|---|---|
| atg | gcg | gct | gcg | acg | gcg | acg | acg | gca | acg | acg | gcg | gtg | atg | gag | caa | 48 |
| Met | Ala | Ala | Ala | Thr | Ala | Thr | Thr | Ala | Thr | Thr | Ala | Val | Met | Glu | Gln | |
| 1 | | | | 5 | | | | | 10 | | | | | 15 | | |
| gtg | ccc | att | acg | gag | gcc | atc | ttc | cgg | ccg | gac | ctc | tgg | gtc | gga | cgg | 96 |
| Val | Pro | Ile | Thr | Glu | Ala | Ile | Phe | Arg | Pro | Asp | Leu | Trp | Val | Gly | Arg | |
| | | | 20 | | | | | 25 | | | | | 30 | | | |
| gac | cag | tgg | gag | gcg | aat | gcc | gtg | agc | ttc | gta | tgg | agg | tac | tgg | tgg | 144 |
| Asp | Gln | Trp | Glu | Ala | Asn | Ala | Val | Ser | Phe | Val | Trp | Arg | Tyr | Trp | Trp | |
| | | 35 | | | | | 40 | | | | | 45 | | | | |
| ttc | ttc | ctg | gtg | atg | ggc | gtg | gca | tac | ctg | ccc | atc | atc | ttc | ggc | ctc | 192 |
| Phe | Phe | Leu | Val | Met | Gly | Val | Ala | Tyr | Leu | Pro | Ile | Ile | Phe | Gly | Leu | |
| | 50 | | | | | 55 | | | | | 60 | | | | | |
| aag | tac | tgg | atg | aag | gat | cgt | ccg | gcc | ttc | aac | ctc | cgg | cgg | ccg | ctc | 240 |
| Lys | Tyr | Trp | Met | Lys | Asp | Arg | Pro | Ala | Phe | Asn | Leu | Arg | Arg | Pro | Leu | |
| 65 | | | | | 70 | | | | | 75 | | | | | 80 | |
| atc | ttg | tgg | aat | atc | ttc | atg | gcg | acg | ttc | tcg | acc | gcc | ggc | ttc | ctg | 288 |
| Ile | Leu | Trp | Asn | Ile | Phe | Met | Ala | Thr | Phe | Ser | Thr | Ala | Gly | Phe | Leu | |
| | | | | 85 | | | | | 90 | | | | | 95 | | |
| tcg | atc | gtc | tac | ccc | ctc | atc | gag | aac | tgg | gtc | tac | ccc | ggc | ggc | ggc | 336 |
| Ser | Ile | Val | Tyr | Pro | Leu | Ile | Glu | Asn | Trp | Val | Tyr | Pro | Gly | Gly | Gly | |
| | | | 100 | | | | | 105 | | | | | 110 | | | |
| ctc | acc | ccg | cat | gag | ttc | atc | tgc | tcg | gcc | agc | tac | tcc | tac | aag | ttt | 384 |
| Leu | Thr | Pro | His | Glu | Phe | Ile | Cys | Ser | Ala | Ser | Tyr | Ser | Tyr | Lys | Phe | |
| | | 115 | | | | | 120 | | | | | 125 | | | | |
| ggt | gat | tgc | gcc | atc | tgg | gtg | ttc | ctc | ttc | aac | atg | tcg | aag | atc | ctc | 432 |
| Gly | Asp | Cys | Ala | Ile | Trp | Val | Phe | Leu | Phe | Asn | Met | Ser | Lys | Ile | Leu | |
| | 130 | | | | | 135 | | | | | 140 | | | | | |
| gag | ttc | gtc | gac | acc | atc | ttc | atc | gtc | ccc | agg | aag | acc | cac | ctc | ggc | 480 |
| Glu | Phe | Val | Asp | Thr | Ile | Phe | Ile | Val | Pro | Arg | Lys | Thr | His | Leu | Gly | |
| 145 | | | | | 150 | | | | | 155 | | | | | 160 | |
| ttc | ctc | cac | tac | tac | cac | cac | atc | atc | acc | tac | tcc | ttc | tgc | ctc | tac | 528 |
| Phe | Leu | His | Tyr | Tyr | His | His | Ile | Ile | Thr | Tyr | Ser | Phe | Cys | Leu | Tyr | |
| | | | | 165 | | | | | 170 | | | | | 175 | | |
| gcc | ggc | cag | tac | atg | cac | cac | tac | aac | tgt | ggc | ggc | tat | ttc | ttc | tgc | 576 |
| Ala | Gly | Gln | Tyr | Met | His | His | Tyr | Asn | Cys | Gly | Gly | Tyr | Phe | Phe | Cys | |
| | | | 180 | | | | | 185 | | | | | 190 | | | |
| ctc | atg | aac | ttc | ttc | gtc | cac | ggc | atc | atg | tac | ttc | tac | tac | gct | ctc | 624 |
| Leu | Met | Asn | Phe | Phe | Val | His | Gly | Ile | Met | Tyr | Phe | Tyr | Tyr | Ala | Leu | |
| | | 195 | | | | | 200 | | | | | 205 | | | | |
| cgc | tcc | atg | ggc | ttc | cgt | ccc | tcc | ttc | gat | att | ggc | atc | acc | ttc | ctc | 672 |
| Arg | Ser | Met | Gly | Phe | Arg | Pro | Ser | Phe | Asp | Ile | Gly | Ile | Thr | Phe | Leu | |
| | 210 | | | | | 215 | | | | | 220 | | | | | |

```
cag att ttg caa atg gtg ctc ggc gtg gcc atc atc acc atc tcc gcc    720
Gln Ile Leu Gln Met Val Leu Gly Val Ala Ile Ile Thr Ile Ser Ala
225                 230                 235                 240 ggc tgc gag aag gtg gac ccc atc gga acg acc ttc ggc tac ttt att    768
Gly Cys Glu Lys Val Asp Pro Ile Gly Thr Thr Phe Gly Tyr Phe Ile
                245                 250                 255 tat ttc tcg ttc ttc gtc ctc ttc tgc aag ttc ttc tac tac cgc tac    816
Tyr Phe Ser Phe Phe Val Leu Phe Cys Lys Phe Phe Tyr Tyr Arg Tyr
            260                 265                 270 atc gcc acg ccc gcc aag aag ccc gag gcc gcc gcc aag tcg cca gcc    864
Ile Ala Thr Pro Ala Lys Lys Pro Glu Ala Ala Ala Lys Ser Pro Ala
        275                 280                 285 acc aag ccc aag agg aag cac gac taa                                891
Thr Lys Pro Lys Arg Lys His Asp
    290                 295
```

<210> SEQ ID NO 12
<211> LENGTH: 296
<212> TYPE: PRT
<213> ORGANISM: Acanthamoeba castellanii

<400> SEQUENCE: 12

```
Met Ala Ala Thr Ala Thr Thr Ala Thr Thr Ala Val Met Glu Gln
1               5                   10                  15

Val Pro Ile Thr Glu Ala Ile Phe Arg Pro Asp Leu Trp Val Gly Arg
                20                  25                  30

Asp Gln Trp Glu Ala Asn Ala Val Ser Phe Val Trp Arg Tyr Trp Trp
            35                  40                  45

Phe Phe Leu Val Met Gly Val Ala Tyr Leu Pro Ile Ile Phe Gly Leu
        50                  55                  60

Lys Tyr Trp Met Lys Asp Arg Pro Ala Phe Asn Leu Arg Arg Pro Leu
65                  70                  75                  80

Ile Leu Trp Asn Ile Phe Met Ala Thr Phe Ser Thr Ala Gly Phe Leu
                85                  90                  95

Ser Ile Val Tyr Pro Leu Ile Glu Asn Trp Val Tyr Pro Gly Gly Gly
            100                 105                 110

Leu Thr Pro His Glu Phe Ile Cys Ser Ala Ser Tyr Ser Tyr Lys Phe
        115                 120                 125

Gly Asp Cys Ala Ile Trp Val Phe Leu Phe Asn Met Ser Lys Ile Leu
130                 135                 140

Glu Phe Val Asp Thr Ile Phe Ile Val Pro Arg Lys Thr His Leu Gly
145                 150                 155                 160

Phe Leu His Tyr Tyr His His Ile Ile Thr Tyr Ser Phe Cys Leu Tyr
                165                 170                 175

Ala Gly Gln Tyr Met His His Tyr Asn Cys Gly Gly Tyr Phe Phe Cys
            180                 185                 190

Leu Met Asn Phe Val His Gly Ile Met Tyr Phe Tyr Ala Leu
        195                 200                 205

Arg Ser Met Gly Phe Arg Pro Ser Phe Asp Ile Gly Ile Thr Phe Leu
    210                 215                 220

Gln Ile Leu Gln Met Val Leu Gly Val Ala Ile Ile Thr Ile Ser Ala
225                 230                 235                 240

Gly Cys Glu Lys Val Asp Pro Ile Gly Thr Thr Phe Gly Tyr Phe Ile
                245                 250                 255

Tyr Phe Ser Phe Phe Val Leu Phe Cys Lys Phe Phe Tyr Tyr Arg Tyr
            260                 265                 270
```

-continued

```
    Ile Ala Thr Pro Ala Lys Lys Pro Glu Ala Ala Lys Ser Pro Ala
            275                 280                 285

Thr Lys Pro Lys Arg Lys His Asp
    290                 295

<210> SEQ ID NO 13
<211> LENGTH: 1320
<212> TYPE: DNA
<213> ORGANISM: Thraustochytrium sp.
<220> FEATURE:
<221> NAME/KEY: CDS
<222> LOCATION: (1)..(1320)
<223> OTHER INFORMATION: Delta-5-Desaturase

<400> SEQUENCE: 13 atg ggc aag ggc agc gag ggc cgc agc gcg gcg cgc gag atg acg gcc       48
Met Gly Lys Gly Ser Glu Gly Arg Ser Ala Ala Arg Glu Met Thr Ala
1               5                   10                  15 gag gcg aac ggc gac aag cgg aaa acg att ctg atc gag ggc gtc ctg       96
Glu Ala Asn Gly Asp Lys Arg Lys Thr Ile Leu Ile Glu Gly Val Leu
            20                  25                  30 tac gac gcg acg aac ttt aag cac ccg ggc ggt tcg atc atc aac ttc      144
Tyr Asp Ala Thr Asn Phe Lys His Pro Gly Gly Ser Ile Ile Asn Phe
        35                  40                  45 ttg acc gag ggc gag gcc ggc gtg gac gcg acg cag gcg tac cgc gag      192
Leu Thr Glu Gly Glu Ala Gly Val Asp Ala Thr Gln Ala Tyr Arg Glu
    50                  55                  60 ttt cat cag cgg tcc ggc aag gcc gac aag tac ctc aag tcg ctg ccg      240
Phe His Gln Arg Ser Gly Lys Ala Asp Lys Tyr Leu Lys Ser Leu Pro
65                  70                  75                  80 aag ctg gat gcg tcc aag gtg gag tcg cgg ttc tcg gcc aaa gag cag      288
Lys Leu Asp Ala Ser Lys Val Glu Ser Arg Phe Ser Ala Lys Glu Gln
                85                  90                  95 gcg cgg cgc gac gcc atg acg cgc gac tac gcg gcc ttt cgc gag gag      336
Ala Arg Arg Asp Ala Met Thr Arg Asp Tyr Ala Ala Phe Arg Glu Glu
            100                 105                 110 ctc gtc gcc gag ggg tac ttt gac ccg tcg atc ccg cac atg att tac      384
Leu Val Ala Glu Gly Tyr Phe Asp Pro Ser Ile Pro His Met Ile Tyr
        115                 120                 125 cgc gtc gtg gag atc gtg gcg ctc ttc gcg ctc tcg ttc tgg ctc atg      432
Arg Val Val Glu Ile Val Ala Leu Phe Ala Leu Ser Phe Trp Leu Met
    130                 135                 140 tcc aag gcc tcg ccc acc tcg ctc gtg ctg ggc gtg gtg atg aac ggc      480
Ser Lys Ala Ser Pro Thr Ser Leu Val Leu Gly Val Val Met Asn Gly
145                 150                 155                 160 att gcg cag ggc cgc tgc ggc tgg gtc atg cac gag atg ggc cac ggg      528
Ile Ala Gln Gly Arg Cys Gly Trp Val Met His Glu Met Gly His Gly
                165                 170                 175 tcg ttc acg ggc gtc atc tgg ctc gac gac cgg atg tgc gag ttc ttc      576
Ser Phe Thr Gly Val Ile Trp Leu Asp Asp Arg Met Cys Glu Phe Phe
            180                 185                 190 tac ggc gtc ggc tgc ggc atg agc ggg cac tac tgg aag aac cag cac      624
Tyr Gly Val Gly Cys Gly Met Ser Gly His Tyr Trp Lys Asn Gln His
        195                 200                 205 agc aag cac cac gcc gcg ccc aac cgc ctc gag cac gat gtc gat ctc      672
Ser Lys His His Ala Ala Pro Asn Arg Leu Glu His Asp Val Asp Leu
    210                 215                 220 aac acg ctg ccc ctg gtc gcc ttt aac gag cgc gtc gtg cgc aag gtc      720
Asn Thr Leu Pro Leu Val Ala Phe Asn Glu Arg Val Val Arg Lys Val
225                 230                 235                 240 aag ccg gga tcg ctg ctg gcg ctc tgg ctg cgc gtg cag gcg tac ctc      768
Lys Pro Gly Ser Leu Leu Ala Leu Trp Leu Arg Val Gln Ala Tyr Leu
```

```
                      245                 250                 255
ttt gcg ccc gtc tcg tgc ctg ctc atc ggc ctt ggc tgg acg ctc tac        816
Phe Ala Pro Val Ser Cys Leu Leu Ile Gly Leu Gly Trp Thr Leu Tyr
            260                 265                 270 ctg cac ccg cgc tac atg ctg cgc acc aag cgg cac atg gag ttc gtc        864
Leu His Pro Arg Tyr Met Leu Arg Thr Lys Arg His Met Glu Phe Val
                275                 280                 285 tgg atc ttc gcg cgc tac att ggc tgg ttc tcg ctc atg ggc gct ctc        912
Trp Ile Phe Ala Arg Tyr Ile Gly Trp Phe Ser Leu Met Gly Ala Leu
        290                 295                 300 ggc tac tcg ccg ggc acc tcg gtc ggg atg tac ctg tgc tcg ttc ggc        960
Gly Tyr Ser Pro Gly Thr Ser Val Gly Met Tyr Leu Cys Ser Phe Gly
305                 310                 315                 320 ctc ggc tgc att tac att ttc ctg cag ttc gcc gtc agc cac acg cac       1008
Leu Gly Cys Ile Tyr Ile Phe Leu Gln Phe Ala Val Ser His Thr His
                325                 330                 335 ctg ccg gtg acc aac ccg gag gac cag ctg cac tgg ctc gag tac gcg       1056
Leu Pro Val Thr Asn Pro Glu Asp Gln Leu His Trp Leu Glu Tyr Ala
            340                 345                 350 gcc gac cac acg gtg aac att agc acc aag tcc tgg ctc gtc acg tgg       1104
Ala Asp His Thr Val Asn Ile Ser Thr Lys Ser Trp Leu Val Thr Trp
                355                 360                 365 tgg atg tcg aac ctg aac ttt cag atc gag cac cac ctc ttc ccc acg       1152
Trp Met Ser Asn Leu Asn Phe Gln Ile Glu His His Leu Phe Pro Thr
        370                 375                 380 gcg ccg cag ttc cgc ttc aag gaa atc agt cct cgc gtc gag gcc ctc       1200
Ala Pro Gln Phe Arg Phe Lys Glu Ile Ser Pro Arg Val Glu Ala Leu
385                 390                 395                 400 ttc aag cgc cac aac ctc ccg tac tac gac ctg ccc tac acg agc gcg       1248
Phe Lys Arg His Asn Leu Pro Tyr Tyr Asp Leu Pro Tyr Thr Ser Ala
                405                 410                 415 gtc tcg acc acc ttt gcc aat ctt tat tcc gtc ggc cac tcg gtc ggc       1296
Val Ser Thr Thr Phe Ala Asn Leu Tyr Ser Val Gly His Ser Val Gly
            420                 425                 430 gcc gac acc aag aag cag gac tga                                       1320
Ala Asp Thr Lys Lys Gln Asp
        435
```

<210> SEQ ID NO 14
<211> LENGTH: 439
<212> TYPE: PRT
<213> ORGANISM: Thraustochytrium sp.

<400> SEQUENCE: 14

```
Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
            85                  90                  95

Ala Arg Arg Asp Ala Met Thr Arg Asp Tyr Ala Ala Phe Arg Glu Glu
        100                 105                 110

Leu Val Ala Glu Gly Tyr Phe Asp Pro Ser Ile Pro His Met Ile Tyr
```

```
              115                 120                 125
Arg Val Val Glu Ile Val Ala Leu Phe Ala Leu Ser Phe Trp Leu Met
130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Met Gly Ala Leu
    290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Leu Val Thr Trp
        355                 360                 365

Trp Met Ser Asn Leu Asn Phe Gln Ile Glu His His Leu Phe Pro Thr
    370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
            420                 425                 430

Ala Asp Thr Lys Lys Gln Asp
        435

<210> SEQ ID NO 15
<211> LENGTH: 1353
<212> TYPE: DNA
<213> ORGANISM: Acanthamoeba castellanii
<220> FEATURE:
<221> NAME/KEY: CDS
<222> LOCATION: (1)..(1353)
<223> OTHER INFORMATION: Delta-5-Desaturase

<400> SEQUENCE: 15 atg gcc acc gca tct gca tcc aac gtt ctc cgc ctg ccc gga gag gga     48
Met Ala Thr Ala Ser Ala Ser Asn Val Leu Arg Leu Pro Gly Glu Gly
1               5                   10                  15 ctc gcg act ggc ctc gag cag ctc gag tgg gcc gaa gtg cag aag cac     96
Leu Ala Thr Gly Leu Glu Gln Leu Glu Trp Ala Glu Val Gln Lys His
```

-continued

```
                      20                  25                  30
aac acg cgc gag agc tcg tgg ctg gtg att aac gac cag gtg tac gac      144
Asn Thr Arg Glu Ser Ser Trp Leu Val Ile Asn Asp Gln Val Tyr Asp
             35                  40                  45 atc acc aac ttc ggc cgg cgc cat ccc ggt ggc aag gta atc tac cac      192
Ile Thr Asn Phe Gly Arg Arg His Pro Gly Gly Lys Val Ile Tyr His
 50                  55                  60 tac gcg ggt caa gat gcc acg gac tcg ttt cgg gct ctt cac ccc gat      240
Tyr Ala Gly Gln Asp Ala Thr Asp Ser Phe Arg Ala Leu His Pro Asp
 65                  70                  75                  80 tcc gcc ctg gtg atg aag tat ctc aag ccc ctc ctc atc ggt caa gtg      288
Ser Ala Leu Val Met Lys Tyr Leu Lys Pro Leu Leu Ile Gly Gln Val
                 85                  90                  95 gca ccc ggc tca tcc acc gca gca tcg att gtt gat ggc gcc cgc ccg      336
Ala Pro Gly Ser Ser Thr Ala Ala Ser Ile Val Asp Gly Ala Arg Pro
            100                 105                 110 gcg ccc tcg gca ttc gta gag gaa ttc aga cag gtg cgc aaa gaa ttc      384
Ala Pro Ser Ala Phe Val Glu Glu Phe Arg Gln Val Arg Lys Glu Phe
        115                 120                 125 gag gag cag ggc ctg ttc gag gcc agc tgg tcc ttc ttc ttc ggg atg      432
Glu Glu Gln Gly Leu Phe Glu Ala Ser Trp Ser Phe Phe Phe Gly Met
130                 135                 140 ctg gcc cac atc ttc ctg ctc gag gct gcc gcc tac tac agc atc aag      480
Leu Ala His Ile Phe Leu Leu Glu Ala Ala Ala Tyr Tyr Ser Ile Lys
145                 150                 155                 160 ctg ctg ggc aac agt tgg ccc gtc tac ctc ctc gcc gtc ggc ctc ctc      528
Leu Leu Gly Asn Ser Trp Pro Val Tyr Leu Leu Ala Val Gly Leu Leu
                165                 170                 175 gcc act gcc cag gca cag gcc ggc tgg ctc cag cac gat tgt ggg cac      576
Ala Thr Ala Gln Ala Gln Ala Gly Trp Leu Gln His Asp Cys Gly His
            180                 185                 190 ttg tcc gtg ttc aag aag tcg aag tgg aac cat tgg atg cac tac atc      624
Leu Ser Val Phe Lys Lys Ser Lys Trp Asn His Trp Met His Tyr Ile
        195                 200                 205 gtc atc tgc cac atc aag ggc gcc tcg cga gcc tgg tgg aac tgg cgt      672
Val Ile Cys His Ile Lys Gly Ala Ser Arg Ala Trp Trp Asn Trp Arg
210                 215                 220 cac ttt gag cac cac gca aag ccc aac gtg gtg cgc aag gac ccc gac      720
His Phe Glu His His Ala Lys Pro Asn Val Val Arg Lys Asp Pro Asp
225                 230                 235                 240 atc acc ttc ccc aac ctc ttc ctt ctc ggc gac cac ctg acg cgc aag      768
Ile Thr Phe Pro Asn Leu Phe Leu Leu Gly Asp His Leu Thr Arg Lys
                245                 250                 255 tgg gcc aag gcc aag aag gga gtg atg ccc tac aac aag cag cac ctc      816
Trp Ala Lys Ala Lys Lys Gly Val Met Pro Tyr Asn Lys Gln His Leu
            260                 265                 270 tac tgg tgg gct ttc ccc ccg ctc ctg ctg ccc gtc tac ttc cac tac      864
Tyr Trp Trp Ala Phe Pro Pro Leu Leu Leu Pro Val Tyr Phe His Tyr
        275                 280                 285 gac aac att cga tac gtc ttc cag cac aag cac tgg tgg gac ctc ttc      912
Asp Asn Ile Arg Tyr Val Phe Gln His Lys His Trp Trp Asp Leu Phe
290                 295                 300 tgg atc gcc acg ttc ttc gcg aag cac ttc acg ctc tac ggc ccg ctg      960
Trp Ile Ala Thr Phe Phe Ala Lys His Phe Thr Leu Tyr Gly Pro Leu
305                 310                 315                 320 atg ggc ggc tgg ggc gcg ttc tgg ttc tac atg ctg gtg cgc acg gtc     1008
Met Gly Gly Trp Gly Ala Phe Trp Phe Tyr Met Leu Val Arg Thr Val
                325                 330                 335 gag agc cac tgg ttc aca tgg gtg acc cag atg aac cac atc ccc atg     1056
Glu Ser His Trp Phe Thr Trp Val Thr Gln Met Asn His Ile Pro Met
```

```
                  340                 345                 350
cac gtc gac aac gac cgc gag ctg gac tgg ccc acc ctg cag ggt ctc     1104
His Val Asp Asn Asp Arg Glu Leu Asp Trp Pro Thr Leu Gln Gly Leu
            355                 360                 365 gcc acg tgc aac gtc gag ggc agc ctc ttc aac gac tgg ttc acg ggc     1152
Ala Thr Cys Asn Val Glu Gly Ser Leu Phe Asn Asp Trp Phe Thr Gly
370                 375                 380 cac ctc aac tac cag atc gag cac cac ctc ttc ccc acc atg ccc cgc     1200
His Leu Asn Tyr Gln Ile Glu His His Leu Phe Pro Thr Met Pro Arg
385                 390                 395                 400 cac aac tac gcg gtg gcc aac aag aag gtc cag gcc ctc tac aag aag     1248
His Asn Tyr Ala Val Ala Asn Lys Lys Val Gln Ala Leu Tyr Lys Lys
            405                 410                 415 cac ggc gtg ccg atg cag acc aag ggc ctc atc gaa gcc ttc gcc gac     1296
His Gly Val Pro Met Gln Thr Lys Gly Leu Ile Glu Ala Phe Ala Asp
            420                 425                 430 atc gtc aag tcg ctc gag cac tat ggt gag gtg tgg aag gag gcc tac     1344
Ile Val Lys Ser Leu Glu His Tyr Gly Glu Val Trp Lys Glu Ala Tyr
            435                 440                 445 tac ggc taa                                                         1353
Tyr Gly
    450

<210> SEQ ID NO 16
<211> LENGTH: 450
<212> TYPE: PRT
<213> ORGANISM: Acanthamoeba castellanii

<400> SEQUENCE: 16

Met Ala Thr Ala Ser Ala Ser Asn Val Leu Arg Leu Pro Gly Glu Gly
1               5                   10                  15

Leu Ala Thr Gly Leu Glu Gln Leu Glu Trp Ala Glu Val Gln Lys His
            20                  25                  30

Asn Thr Arg Glu Ser Ser Trp Leu Val Ile Asn Asp Gln Val Tyr Asp
        35                  40                  45

Ile Thr Asn Phe Gly Arg Arg His Pro Gly Gly Lys Val Ile Tyr His
    50                  55                  60

Tyr Ala Gly Gln Asp Ala Thr Asp Ser Phe Arg Ala Leu His Pro Asp
65                  70                  75                  80

Ser Ala Leu Val Met Lys Tyr Leu Lys Pro Leu Leu Ile Gly Gln Val
                85                  90                  95

Ala Pro Gly Ser Ser Thr Ala Ser Ile Val Asp Gly Ala Arg Pro
            100                 105                 110

Ala Pro Ser Ala Phe Val Glu Glu Phe Arg Gln Val Arg Lys Glu Phe
        115                 120                 125

Glu Glu Gln Gly Leu Phe Glu Ala Ser Trp Ser Phe Phe Gly Met
    130                 135                 140

Leu Ala His Ile Phe Leu Leu Glu Ala Ala Tyr Tyr Ser Ile Lys
145                 150                 155                 160

Leu Leu Gly Asn Ser Trp Pro Val Tyr Leu Leu Ala Val Gly Leu Leu
                165                 170                 175

Ala Thr Ala Gln Ala Gln Ala Gly Trp Leu Gln His Asp Cys Gly His
            180                 185                 190

Leu Ser Val Phe Lys Lys Ser Lys Trp Asn His Trp Met His Tyr Ile
        195                 200                 205

Val Ile Cys His Ile Lys Gly Ala Ser Arg Ala Trp Trp Asn Trp Arg
    210                 215                 220
```

```
His Phe Glu His His Ala Lys Pro Asn Val Val Arg Lys Asp Pro Asp
225                 230                 235                 240

Ile Thr Phe Pro Asn Leu Phe Leu Leu Gly Asp His Leu Thr Arg Lys
            245                 250                 255

Trp Ala Lys Ala Lys Lys Gly Val Met Pro Tyr Asn Lys Gln His Leu
        260                 265                 270

Tyr Trp Trp Ala Phe Pro Pro Leu Leu Leu Pro Val Tyr Phe His Tyr
    275                 280                 285

Asp Asn Ile Arg Tyr Val Phe Gln His Lys His Trp Trp Asp Leu Phe
290                 295                 300

Trp Ile Ala Thr Phe Phe Ala Lys His Phe Thr Leu Tyr Gly Pro Leu
305                 310                 315                 320

Met Gly Gly Trp Gly Ala Phe Trp Phe Tyr Met Leu Val Arg Thr Val
            325                 330                 335

Glu Ser His Trp Phe Thr Trp Val Thr Gln Met Asn His Ile Pro Met
        340                 345                 350

His Val Asp Asn Asp Arg Glu Leu Asp Trp Pro Thr Leu Gln Gly Leu
    355                 360                 365

Ala Thr Cys Asn Val Glu Gly Ser Leu Phe Asn Asp Trp Phe Thr Gly
370                 375                 380

His Leu Asn Tyr Gln Ile Glu His His Leu Phe Pro Thr Met Pro Arg
385                 390                 395                 400

His Asn Tyr Ala Val Ala Asn Lys Lys Val Gln Ala Leu Tyr Lys Lys
            405                 410                 415

His Gly Val Pro Met Gln Thr Lys Gly Leu Ile Glu Ala Phe Ala Asp
        420                 425                 430

Ile Val Lys Ser Leu Glu His Tyr Gly Glu Val Trp Lys Glu Ala Tyr
    435                 440                 445

Tyr Gly
    450

<210> SEQ ID NO 17
<211> LENGTH: 1374
<212> TYPE: DNA
<213> ORGANISM: Perkinsus marinus
<220> FEATURE:
<221> NAME/KEY: CDS
<222> LOCATION: (1)..(1374)
<223> OTHER INFORMATION: Delta-5-Desaturase

<400> SEQUENCE: 17 atg act act tca acc act act gtg caa cta caa gaa gac ctg tca agt        48
Met Thr Thr Ser Thr Thr Thr Val Gln Leu Gln Glu Asp Leu Ser Ser
1               5                  10                  15 ggt gac cag aac gcc cac ccc agt cca agc cga gct act cct agt gtt        96
Gly Asp Gln Asn Ala His Pro Ser Pro Ser Arg Ala Thr Pro Ser Val
            20                  25                  30 ggt gat act aag gag gat gcg agg gtt gtt atc aaa cta ttt ggt aca       144
Gly Asp Thr Lys Glu Asp Ala Arg Val Val Ile Lys Leu Phe Gly Thr
        35                  40                  45 tgg gtt gat gtt aca gct tgg ttg aat gac cat cct ggt ggt tct aaa       192
Trp Val Asp Val Thr Ala Trp Leu Asn Asp His Pro Gly Gly Ser Lys
    50                  55                  60 gtg ctc aga gca ttc aac aag aag gac gcg act gat gct gtt atg gcc       240
Val Leu Arg Ala Phe Asn Lys Lys Asp Ala Thr Asp Ala Val Met Ala
65                  70                  75                  80 atg cac act gat gaa gct atc aag cgc atc atc aga ttt tca aat gtg       288
Met His Thr Asp Glu Ala Ile Lys Arg Ile Ile Arg Phe Ser Asn Val
            85                  90                  95
```

```
gtc tcc tcg gcc ccc atc aac gcc tct att ggt gat gtc cag gtt att      336
Val Ser Ser Ala Pro Ile Asn Ala Ser Ile Gly Asp Val Gln Val Ile
            100                 105                 110 gag aaa tct cta tcg aga gaa cag ttg atg tat tac aag ctc cgc act      384
Glu Lys Ser Leu Ser Arg Glu Gln Leu Met Tyr Tyr Lys Leu Arg Thr
        115                 120                 125 ctt gct aga aac cag ggc tgg ttt caa agc aat cta tta tac gaa gga      432
Leu Ala Arg Asn Gln Gly Trp Phe Gln Ser Asn Leu Leu Tyr Glu Gly
    130                 135                 140 gtg aaa gca atg ata gcc ttc ggt ttg ctc atc atc ggg ttt gct act      480
Val Lys Ala Met Ile Ala Phe Gly Leu Leu Ile Ile Gly Phe Ala Thr
145                 150                 155                 160 ctc tac ttc gac tat ggt att tgg tca acc gca ctg ata ggt ttc gct      528
Leu Tyr Phe Asp Tyr Gly Ile Trp Ser Thr Ala Leu Ile Gly Phe Ala
                165                 170                 175 tgg ttt cag ctg ggg tgg ttg gga cat gac tgg tct cat cat aca gct      576
Trp Phe Gln Leu Gly Trp Leu Gly His Asp Trp Ser His His Thr Ala
            180                 185                 190 cta cca aag tct act act aac tgt gcg aac tac aat gac tat ctt ggc      624
Leu Pro Lys Ser Thr Thr Asn Cys Ala Asn Tyr Asn Asp Tyr Leu Gly
        195                 200                 205 tgg ctt act ggt ttg gct aga ggg aat aca ctt ctg tgg tgg aaa cta      672
Trp Leu Thr Gly Leu Ala Arg Gly Asn Thr Leu Leu Trp Trp Lys Leu
    210                 215                 220 agg cat aat act cat cac gtg ctg acc aat cag tac gag aat gat cct      720
Arg His Asn Thr His His Val Leu Thr Asn Gln Tyr Glu Asn Asp Pro
225                 230                 235                 240 gat ata cta act caa cca ccg ttg cat ttt ttc gag gac ttc gat gtt      768
Asp Ile Leu Thr Gln Pro Pro Leu His Phe Phe Glu Asp Phe Asp Val
                245                 250                 255 ggt aat gtg aac aga tat caa gct gtc tac tat cta cca atg cta act      816
Gly Asn Val Asn Arg Tyr Gln Ala Val Tyr Tyr Leu Pro Met Leu Thr
            260                 265                 270 cta ctg cat cta ttt tgg ttg tac gag tcg gta ttg gtt tgc ttg aga      864
Leu Leu His Leu Phe Trp Leu Tyr Glu Ser Val Leu Val Cys Leu Arg
        275                 280                 285 caa agt aag tct att aat aga tac aac cgt atg cat gcc cgg agg gat      912
Gln Ser Lys Ser Ile Asn Arg Tyr Asn Arg Met His Ala Arg Arg Asp
    290                 295                 300 acc gta gct ttg gta ctt cac ata ctc att gtt ggc atc ata tcg tac      960
Thr Val Ala Leu Val Leu His Ile Leu Ile Val Gly Ile Ile Ser Tyr
305                 310                 315                 320 acc agt ggt aag tat ttg ctc atc ctt ctg gcc tac atg ctt agt ggc     1008
Thr Ser Gly Lys Tyr Leu Leu Ile Leu Leu Ala Tyr Met Leu Ser Gly
                325                 330                 335 ttt cta act gct gtt gtt gta ttt gcc agc cac tac aac gag cct agg     1056
Phe Leu Thr Ala Val Val Val Phe Ala Ser His Tyr Asn Glu Pro Arg
            340                 345                 350 gta gct tct ggt gaa tcc tta tca ctc gtt cgt cag aca ttg tta acc     1104
Val Ala Ser Gly Glu Ser Leu Ser Leu Val Arg Gln Thr Leu Leu Thr
        355                 360                 365 act atc aat ata ggc tca ttc agt gat act cat tgg gag aag aag ttg     1152
Thr Ile Asn Ile Gly Ser Phe Ser Asp Thr His Trp Glu Lys Lys Leu
    370                 375                 380 tgg ttc tat cta act ggt ggt ctt aat atg caa atc gag cat cat ctc     1200
Trp Phe Tyr Leu Thr Gly Gly Leu Asn Met Gln Ile Glu His His Leu
385                 390                 395                 400 ttc cca aca atg ccc cgc cat aat ctt ccg aag aca act ttt ctg gtc     1248
Phe Pro Thr Met Pro Arg His Asn Leu Pro Lys Thr Thr Phe Leu Val
                405                 410                 415
```

```
aag tca cta gcc cag gag cta gga ctg cca tac aag gaa acc aac att    1296
Lys Ser Leu Ala Gln Glu Leu Gly Leu Pro Tyr Lys Glu Thr Asn Ile
        420                 425                 430 gtc agt tta acc aag gcg gcc gtt act act ttg cat cat aat gct ctg    1344
Val Ser Leu Thr Lys Ala Ala Val Thr Thr Leu His His Asn Ala Leu
        435                 440                 445 cgt aac atc gag aga ttg ctt gct agg tag                            1374
Arg Asn Ile Glu Arg Leu Leu Ala Arg
        450                 455

<210> SEQ ID NO 18
<211> LENGTH: 457
<212> TYPE: PRT
<213> ORGANISM: Perkinsus marinus

<400> SEQUENCE: 18
```

Met Thr Thr Ser Thr Thr Thr Val Gln Leu Gln Glu Asp Leu Ser Ser
1               5                   10                  15

Gly Asp Gln Asn Ala His Pro Ser Pro Ser Arg Ala Thr Pro Ser Val
            20                  25                  30

Gly Asp Thr Lys Glu Asp Ala Arg Val Val Ile Lys Leu Phe Gly Thr
        35                  40                  45

Trp Val Asp Val Thr Ala Trp Leu Asn Asp His Pro Gly Gly Ser Lys
    50                  55                  60

Val Leu Arg Ala Phe Asn Lys Lys Asp Ala Thr Asp Ala Val Met Ala
65                  70                  75                  80

Met His Thr Asp Glu Ala Ile Lys Arg Ile Ile Arg Phe Ser Asn Val
                85                  90                  95

Val Ser Ser Ala Pro Ile Asn Ala Ser Ile Gly Asp Val Gln Val Ile
            100                 105                 110

Glu Lys Ser Leu Ser Arg Glu Gln Leu Met Tyr Tyr Lys Leu Arg Thr
        115                 120                 125

Leu Ala Arg Asn Gln Gly Trp Phe Gln Ser Asn Leu Leu Tyr Glu Gly
    130                 135                 140

Val Lys Ala Met Ile Ala Phe Gly Leu Leu Ile Ile Gly Phe Ala Thr
145                 150                 155                 160

Leu Tyr Phe Asp Tyr Gly Ile Trp Ser Thr Ala Leu Ile Gly Phe Ala
                165                 170                 175

Trp Phe Gln Leu Gly Trp Leu Gly His Asp Trp Ser His His Thr Ala
            180                 185                 190

Leu Pro Lys Ser Thr Thr Asn Cys Ala Asn Tyr Asn Asp Tyr Leu Gly
        195                 200                 205

Trp Leu Thr Gly Leu Ala Arg Gly Asn Thr Leu Leu Trp Trp Lys Leu
    210                 215                 220

Arg His Asn Thr His His Val Leu Thr Asn Gln Tyr Glu Asn Asp Pro
225                 230                 235                 240

Asp Ile Leu Thr Gln Pro Pro Leu His Phe Phe Glu Asp Phe Asp Val
                245                 250                 255

Gly Asn Val Asn Arg Tyr Gln Ala Val Tyr Tyr Leu Pro Met Leu Thr
            260                 265                 270

Leu Leu His Leu Phe Trp Leu Tyr Glu Ser Val Leu Val Cys Leu Arg
        275                 280                 285

Gln Ser Lys Ser Ile Asn Arg Tyr Asn Arg Met His Ala Arg Arg Asp
    290                 295                 300

Thr Val Ala Leu Val Leu His Ile Leu Ile Val Gly Ile Ile Ser Tyr
305                 310                 315                 320

```
Thr Ser Gly Lys Tyr Leu Leu Ile Leu Leu Ala Tyr Met Leu Ser Gly
            325                 330                 335

Phe Leu Thr Ala Val Val Phe Ala Ser His Tyr Asn Glu Pro Arg
            340                 345                 350

Val Ala Ser Gly Glu Ser Leu Ser Leu Val Arg Gln Thr Leu Leu Thr
            355                 360                 365

Thr Ile Asn Ile Gly Ser Phe Ser Asp Thr His Trp Glu Lys Lys Leu
        370                 375                 380

Trp Phe Tyr Leu Thr Gly Gly Leu Asn Met Gln Ile Glu His His Leu
385                 390                 395                 400

Phe Pro Thr Met Pro Arg His Asn Leu Pro Lys Thr Thr Phe Leu Val
                405                 410                 415

Lys Ser Leu Ala Gln Glu Leu Gly Leu Pro Tyr Lys Glu Thr Asn Ile
            420                 425                 430

Val Ser Leu Thr Lys Ala Ala Val Thr Thr Leu His His Asn Ala Leu
            435                 440                 445

Arg Asn Ile Glu Arg Leu Leu Ala Arg
    450                 455
```

<210> SEQ ID NO 19
<211> LENGTH: 1224
<212> TYPE: DNA
<213> ORGANISM: Acanthamoeba castellanii
<220> FEATURE:
<221> NAME/KEY: CDS
<222> LOCATION: (1)..(1224)
<223> OTHER INFORMATION: Delta-12/Delta-15-Desaturase

<400> SEQUENCE: 19

```
atg act att act act acc cag acc ttg aac cag aag gct gct aag aag        48
Met Thr Ile Thr Thr Thr Gln Thr Leu Asn Gln Lys Ala Ala Lys Lys
1               5                   10                  15 gga gga aag gag agg gct cca att att cca aag gag aac gct cca ttc        96
Gly Gly Lys Glu Arg Ala Pro Ile Ile Pro Lys Glu Asn Ala Pro Phe
            20                  25                  30 act ttg gga cag atc aag gga gct atc cca cct cat ctc ttc aag cac       144
Thr Leu Gly Gln Ile Lys Gly Ala Ile Pro Pro His Leu Phe Lys His
        35                  40                  45 tcc atg ttg aag tct ttc tcc tac ttg gga gtg gat ttg ttg gag tct       192
Ser Met Leu Lys Ser Phe Ser Tyr Leu Gly Val Asp Leu Leu Glu Ser
    50                  55                  60 acc atc tgg ttg ttc ctc atc ttg tac ttg gat gga ctc act aag gag       240
Thr Ile Trp Leu Phe Leu Ile Leu Tyr Leu Asp Gly Leu Thr Lys Glu
65                  70                  75                  80 aac acc ttg ttg aac tgg act tgc tgg gtt gca tac tgg ttg tac caa       288
Asn Thr Leu Leu Asn Trp Thr Cys Trp Val Ala Tyr Trp Leu Tyr Gln
                85                  90                  95 gga ttg act tgg act gga att tgg gtg ttg gct cat gag tgt gga cat       336
Gly Leu Thr Trp Thr Gly Ile Trp Val Leu Ala His Glu Cys Gly His
            100                 105                 110 gga gga ttc gtt gct caa gag tgg ttg aac gat acc gtg ggt ttc att       384
Gly Gly Phe Val Ala Gln Glu Trp Leu Asn Asp Thr Val Gly Phe Ile
        115                 120                 125 ttc cat acc gtg ctc tac gtt cca tac ttc tcc tgg aag ttc tct cat       432
Phe His Thr Val Leu Tyr Val Pro Tyr Phe Ser Trp Lys Phe Ser His
    130                 135                 140 gct aag cac cat cac tac acc aac cac atg act aag gat gag cca ttc       480
Ala Lys His His His Tyr Thr Asn His Met Thr Lys Asp Glu Pro Phe
145                 150                 155                 160
```

```
gtg cca cat aca atc act cca gag caa agg gct aaa gtg gat caa gga      528
Val Pro His Thr Ile Thr Pro Glu Gln Arg Ala Lys Val Asp Gln Gly
            165                 170                 175 gag ttg cca cat cca aac aag cca tcc ctc ttc gct ttc tac gag aga      576
Glu Leu Pro His Pro Asn Lys Pro Ser Leu Phe Ala Phe Tyr Glu Arg
                180                 185                 190 tgg gtg atc cca ttc gtg atg ttg ttc ttg gga tgg cca ctc tac ttg      624
Trp Val Ile Pro Phe Val Met Leu Phe Leu Gly Trp Pro Leu Tyr Leu
        195                 200                 205 tct atc aac gct tct gga cca cca aag aag gag ttg gtt tcc cac tac      672
Ser Ile Asn Ala Ser Gly Pro Pro Lys Lys Glu Leu Val Ser His Tyr
    210                 215                 220 gat cca aag gct tcc atc ttc aac aag aaa gat tgg tgg aag atc ttg      720
Asp Pro Lys Ala Ser Ile Phe Asn Lys Lys Asp Trp Trp Lys Ile Leu
225                 230                 235                 240 ctc tct gat ttg gga ttg gtt gct tgg act ttg gct ttg tgg aag ttg      768
Leu Ser Asp Leu Gly Leu Val Ala Trp Thr Leu Ala Leu Trp Lys Leu
                245                 250                 255 gga gag act ttc gga ttc gga ttg gtg gct gct ctt tac att cca cca      816
Gly Glu Thr Phe Gly Phe Gly Leu Val Ala Ala Leu Tyr Ile Pro Pro
            260                 265                 270 gtg ctc gtt acc aac tct tac ttg gtg gct atc acc ttc ttg caa cac      864
Val Leu Val Thr Asn Ser Tyr Leu Val Ala Ile Thr Phe Leu Gln His
                275                 280                 285 acc gat gat atc ctc cca cat tac gat gct act gag tgg act tgg ttg      912
Thr Asp Asp Ile Leu Pro His Tyr Asp Ala Thr Glu Trp Thr Trp Leu
        290                 295                 300 aga gga gct ttg tgc act gtg gat aga tct ttg gga tgg ttc gga gat      960
Arg Gly Ala Leu Cys Thr Val Asp Arg Ser Leu Gly Trp Phe Gly Asp
305                 310                 315                 320 tac aag acc cat cac atc gtt gat act cat gtg acc cac cac atc ttc     1008
Tyr Lys Thr His His Ile Val Asp Thr His Val Thr His His Ile Phe
                325                 330                 335 tct tac ctc cca ttc tat aac gct gag gag gct act aag gct att aag     1056
Ser Tyr Leu Pro Phe Tyr Asn Ala Glu Glu Ala Thr Lys Ala Ile Lys
            340                 345                 350 cca gtg ttg aag gag tat cac tgc gag gat aag aga gga ttc ttc cac     1104
Pro Val Leu Lys Glu Tyr His Cys Glu Asp Lys Arg Gly Phe Phe His
                355                 360                 365 ttc tgg tac ttg ttc ttc aag acc gct gct gag aac tct gtt gtg gat     1152
Phe Trp Tyr Leu Phe Phe Lys Thr Ala Ala Glu Asn Ser Val Val Asp
        370                 375                 380 aac gag acc aac aag tcc cca gga atc ttc tac ttc ttc agg gag gag     1200
Asn Glu Thr Asn Lys Ser Pro Gly Ile Phe Tyr Phe Phe Arg Glu Glu
385                 390                 395                 400 att aag cac gga aag gct cat tga                                     1224
Ile Lys His Gly Lys Ala His
                405

<210> SEQ ID NO 20
<211> LENGTH: 407
<212> TYPE: PRT
<213> ORGANISM: Acanthamoeba castellanii

<400> SEQUENCE: 20

Met Thr Ile Thr Thr Thr Gln Thr Leu Asn Gln Lys Ala Ala Lys Lys
1               5                   10                  15

Gly Gly Lys Glu Arg Ala Pro Ile Ile Pro Lys Glu Asn Ala Pro Phe
            20                  25                  30

Thr Leu Gly Gln Ile Lys Gly Ala Ile Pro Pro His Leu Phe Lys His
        35                  40                  45
```

Ser Met Leu Lys Ser Phe Ser Tyr Leu Gly Val Asp Leu Leu Glu Ser
    50                  55                  60

Thr Ile Trp Leu Phe Leu Ile Leu Tyr Leu Asp Gly Leu Thr Lys Glu
65                  70                  75                  80

Asn Thr Leu Leu Asn Trp Thr Cys Trp Val Ala Tyr Trp Leu Tyr Gln
                85                  90                  95

Gly Leu Thr Trp Thr Gly Ile Trp Val Leu Ala His Glu Cys Gly His
            100                 105                 110

Gly Gly Phe Val Ala Gln Glu Trp Leu Asn Asp Thr Val Gly Phe Ile
        115                 120                 125

Phe His Thr Val Leu Tyr Val Pro Tyr Phe Ser Trp Lys Phe Ser His
    130                 135                 140

Ala Lys His His His Tyr Thr Asn His Met Thr Lys Asp Glu Pro Phe
145                 150                 155                 160

Val Pro His Thr Ile Thr Pro Glu Gln Arg Ala Lys Val Asp Gln Gly
                165                 170                 175

Glu Leu Pro His Pro Asn Lys Pro Ser Leu Phe Ala Phe Tyr Glu Arg
            180                 185                 190

Trp Val Ile Pro Phe Val Met Leu Phe Leu Gly Trp Pro Leu Tyr Leu
        195                 200                 205

Ser Ile Asn Ala Ser Gly Pro Pro Lys Lys Glu Leu Val Ser His Tyr
    210                 215                 220

Asp Pro Lys Ala Ser Ile Phe Asn Lys Lys Asp Trp Trp Lys Ile Leu
225                 230                 235                 240

Leu Ser Asp Leu Gly Leu Val Ala Trp Thr Leu Ala Leu Trp Lys Leu
                245                 250                 255

Gly Glu Thr Phe Gly Phe Gly Leu Val Ala Ala Leu Tyr Ile Pro Pro
            260                 265                 270

Val Leu Val Thr Asn Ser Tyr Leu Val Ala Ile Thr Phe Leu Gln His
        275                 280                 285

Thr Asp Asp Ile Leu Pro His Tyr Asp Ala Thr Glu Trp Thr Trp Leu
    290                 295                 300

Arg Gly Ala Leu Cys Thr Val Asp Arg Ser Leu Gly Trp Phe Gly Asp
305                 310                 315                 320

Tyr Lys Thr His His Ile Val Asp Thr His Val Thr His His Ile Phe
                325                 330                 335

Ser Tyr Leu Pro Phe Tyr Asn Ala Glu Glu Ala Thr Lys Ala Ile Lys
            340                 345                 350

Pro Val Leu Lys Glu Tyr His Cys Glu Asp Lys Arg Gly Phe Phe His
        355                 360                 365

Phe Trp Tyr Leu Phe Phe Lys Thr Ala Ala Glu Asn Ser Val Val Asp
    370                 375                 380

Asn Glu Thr Asn Lys Ser Pro Gly Ile Phe Tyr Phe Phe Arg Glu Glu
385                 390                 395                 400

Ile Lys His Gly Lys Ala His
                405

<210> SEQ ID NO 21
<211> LENGTH: 1224
<212> TYPE: DNA
<213> ORGANISM: Acanthamoeba castellanii
<220> FEATURE:
<221> NAME/KEY: CDS
<222> LOCATION: (1)..(1224)
<223> OTHER INFORMATION: Delta-12/Delta-15-Desaturase

<400> SEQUENCE: 21

```
atg acg atc acg acg acg cag aca ctg aat cag aag gca gcc aag aag        48
Met Thr Ile Thr Thr Thr Gln Thr Leu Asn Gln Lys Ala Ala Lys Lys
1               5                   10                  15 ggc gga aag gag cgc gct ccg atc att ccc aag gag aac gcc ccc ttc        96
Gly Gly Lys Glu Arg Ala Pro Ile Ile Pro Lys Glu Asn Ala Pro Phe
            20                  25                  30 act ctg ggc cag atc aag ggc gcc att cct ccg cat ctc ttc aag cac       144
Thr Leu Gly Gln Ile Lys Gly Ala Ile Pro Pro His Leu Phe Lys His
        35                  40                  45 agc atg ctc aaa tcc ttc agc tat ctg ggc gtg gat ctg ctg gag agc       192
Ser Met Leu Lys Ser Phe Ser Tyr Leu Gly Val Asp Leu Leu Glu Ser
    50                  55                  60 acc atc tgg ctc ttc ctc atc ctc tac ctc gac ggc ctc acc aag gag       240
Thr Ile Trp Leu Phe Leu Ile Leu Tyr Leu Asp Gly Leu Thr Lys Glu
65                  70                  75                  80 aac acg ctc ctc aac tgg act tgc tgg gtt gcg tac tgg ctc tac cag       288
Asn Thr Leu Leu Asn Trp Thr Cys Trp Val Ala Tyr Trp Leu Tyr Gln
                85                  90                  95 ggt ctg acc tgg act ggc att tgg gtg ctg gcc cac gag tgt ggc cat       336
Gly Leu Thr Trp Thr Gly Ile Trp Val Leu Ala His Glu Cys Gly His
            100                 105                 110 ggc ggc ttc gtg gcg cag gag tgg ctc aac gac acg gtc ggc ttc atc       384
Gly Gly Phe Val Ala Gln Glu Trp Leu Asn Asp Thr Val Gly Phe Ile
        115                 120                 125 ttc cac acc gtc ctc tac gtg ccc tac ttc tcg tgg aag ttc tcc cac       432
Phe His Thr Val Leu Tyr Val Pro Tyr Phe Ser Trp Lys Phe Ser His
    130                 135                 140 gcc aag cac cac cac tac acc aac cac atg aca aag gac gag ccc ttc       480
Ala Lys His His His Tyr Thr Asn His Met Thr Lys Asp Glu Pro Phe
145                 150                 155                 160 gtg ccc cac acc atc acc cct gag cag agg gcc aag gtc gac cag ggc       528
Val Pro His Thr Ile Thr Pro Glu Gln Arg Ala Lys Val Asp Gln Gly
                165                 170                 175 gag ctg ccc cac ccc aac aag ccc tcc ctc ttc gcc ttc tac gaa agg       576
Glu Leu Pro His Pro Asn Lys Pro Ser Leu Phe Ala Phe Tyr Glu Arg
            180                 185                 190 tgg gtc atc ccc ttc gtc atg ctc ttc ctc ggc tgg ccg ctc tac ctg       624
Trp Val Ile Pro Phe Val Met Leu Phe Leu Gly Trp Pro Leu Tyr Leu
        195                 200                 205 tcc atc aac gcc tct ggc cct ccc aag aag gag ctt gtg tcc cac tac       672
Ser Ile Asn Ala Ser Gly Pro Pro Lys Lys Glu Leu Val Ser His Tyr
    210                 215                 220 gac ccc aaa gcc agc atc ttc aac aag aag gac tgg tgg aag atc ctt       720
Asp Pro Lys Ala Ser Ile Phe Asn Lys Lys Asp Trp Trp Lys Ile Leu
225                 230                 235                 240 ctc tct gac ctc ggc ctt gtg gcg tgg acc ctg gcc ctc tgg aag ctg       768
Leu Ser Asp Leu Gly Leu Val Ala Trp Thr Leu Ala Leu Trp Lys Leu
                245                 250                 255 ggc gag acc ttc ggc ttc ggt ctc gtg gcc gcc ctc tac att ccg ccc       816
Gly Glu Thr Phe Gly Phe Gly Leu Val Ala Ala Leu Tyr Ile Pro Pro
            260                 265                 270 gtg ctg gtg acc aac tcc tac ctg gtg gcc atc acc ttc ctc cag cac       864
Val Leu Val Thr Asn Ser Tyr Leu Val Ala Ile Thr Phe Leu Gln His
        275                 280                 285 acc gac gac att ctg ccc cac tac gac gcc acc gag tgg acc tgg ctc       912
Thr Asp Asp Ile Leu Pro His Tyr Asp Ala Thr Glu Trp Thr Trp Leu
    290                 295                 300 agg ggt gct ctc tgc act gtt gat cgt tcg ctg ggc tgg ttc ggc gac       960
Arg Gly Ala Leu Cys Thr Val Asp Arg Ser Leu Gly Trp Phe Gly Asp
```

```
                    305                 310                 315                 320
tac aag acg cac cac atc gtc gac acc cac gtg acg cac cac atc ttc              1008
Tyr Lys Thr His His Ile Val Asp Thr His Val Thr His His Ile Phe
                    325                 330                 335 tcg tac ctg ccg ttc tac aac gcc gag gag gcc acc aag gcc atc aag              1056
Ser Tyr Leu Pro Phe Tyr Asn Ala Glu Glu Ala Thr Lys Ala Ile Lys
                340                 345                 350 ccc gtg ctc aag gag tac cac tgc gag gac aag cgt ggc ttc ttc cac              1104
Pro Val Leu Lys Glu Tyr His Cys Glu Asp Lys Arg Gly Phe Phe His
            355                 360                 365 ttc tgg tat ctg ttc ttc aag acc gcc gcc gag aac agc gtt gtc gac              1152
Phe Trp Tyr Leu Phe Phe Lys Thr Ala Ala Glu Asn Ser Val Val Asp
        370                 375                 380 aac gag acc aac aag agc ccc ggc atc ttc tac ttc ttc cgg gag gag              1200
Asn Glu Thr Asn Lys Ser Pro Gly Ile Phe Tyr Phe Phe Arg Glu Glu
385                 390                 395                 400 atc aag cac ggc aag gcc cac tag                                              1224
Ile Lys His Gly Lys Ala His
                405

<210> SEQ ID NO 22
<211> LENGTH: 407
<212> TYPE: PRT
<213> ORGANISM: Acanthamoeba castellanii

<400> SEQUENCE: 22

Met Thr Ile Thr Thr Thr Gln Thr Leu Asn Gln Lys Ala Ala Lys Lys
1               5                   10                  15

Gly Gly Lys Glu Arg Ala Pro Ile Ile Pro Lys Glu Asn Ala Pro Phe
            20                  25                  30

Thr Leu Gly Gln Ile Lys Gly Ala Ile Pro Pro His Leu Phe Lys His
        35                  40                  45

Ser Met Leu Lys Ser Phe Ser Tyr Leu Gly Val Asp Leu Leu Glu Ser
    50                  55                  60

Thr Ile Trp Leu Phe Leu Ile Leu Tyr Leu Asp Gly Leu Thr Lys Glu
65                  70                  75                  80

Asn Thr Leu Leu Asn Trp Thr Cys Trp Val Ala Tyr Trp Leu Tyr Gln
                85                  90                  95

Gly Leu Thr Trp Thr Gly Ile Trp Val Leu Ala His Glu Cys Gly His
            100                 105                 110

Gly Gly Phe Val Ala Gln Glu Trp Leu Asn Asp Thr Val Gly Phe Ile
        115                 120                 125

Phe His Thr Val Leu Tyr Val Pro Tyr Phe Ser Trp Lys Phe Ser His
    130                 135                 140

Ala Lys His His His Tyr Thr Asn His Met Thr Lys Asp Glu Pro Phe
145                 150                 155                 160

Val Pro His Thr Ile Thr Pro Glu Gln Arg Ala Lys Val Asp Gln Gly
                165                 170                 175

Glu Leu Pro His Pro Asn Lys Pro Ser Leu Phe Ala Phe Tyr Glu Arg
            180                 185                 190

Trp Val Ile Pro Phe Val Met Leu Phe Leu Gly Trp Pro Leu Tyr Leu
        195                 200                 205

Ser Ile Asn Ala Ser Gly Pro Lys Lys Glu Leu Val Ser His Tyr
    210                 215                 220

Asp Pro Lys Ala Ser Ile Phe Asn Lys Asp Trp Trp Lys Ile Leu
225                 230                 235                 240

Leu Ser Asp Leu Gly Leu Val Ala Trp Thr Leu Ala Leu Trp Lys Leu
```

```
                       245                 250                 255
Gly Glu Thr Phe Gly Phe Gly Leu Val Ala Ala Leu Tyr Ile Pro Pro
                260                 265                 270

Val Leu Val Thr Asn Ser Tyr Leu Val Ala Ile Thr Phe Leu Gln His
            275                 280                 285

Thr Asp Asp Ile Leu Pro His Tyr Asp Ala Thr Glu Trp Thr Trp Leu
290                 295                 300

Arg Gly Ala Leu Cys Thr Val Asp Arg Ser Leu Gly Trp Phe Gly Asp
305                 310                 315                 320

Tyr Lys Thr His His Ile Val Asp Thr His Val Thr His His Ile Phe
                325                 330                 335

Ser Tyr Leu Pro Phe Tyr Asn Ala Glu Glu Ala Thr Lys Ala Ile Lys
            340                 345                 350

Pro Val Leu Lys Glu Tyr His Cys Glu Asp Lys Arg Gly Phe Phe His
        355                 360                 365

Phe Trp Tyr Leu Phe Phe Lys Thr Ala Ala Glu Asn Ser Val Val Asp
    370                 375                 380

Asn Glu Thr Asn Lys Ser Pro Gly Ile Phe Tyr Phe Arg Glu Glu
385                 390                 395                 400

Ile Lys His Gly Lys Ala His
                405

<210> SEQ ID NO 23
<211> LENGTH: 1254
<212> TYPE: DNA
<213> ORGANISM: Perkinsus marinus
<220> FEATURE:
<221> NAME/KEY: CDS
<222> LOCATION: (1)..(1254)
<223> OTHER INFORMATION: Delta-12-Desaturase

<400> SEQUENCE: 23 atg acc caa act gag gtc caa gcc gga ccg tgt aga gat ggt agg aac      48
Met Thr Gln Thr Glu Val Gln Ala Gly Pro Cys Arg Asp Gly Arg Asn
1               5                   10                  15 ctc aag agt gag gct gat gtt aaa ggc ttc act gcg gag gag ttt act      96
Leu Lys Ser Glu Ala Asp Val Lys Gly Phe Thr Ala Glu Glu Phe Thr
            20                  25                  30 aag gtt ggg ccg tct gtg tgt gct ata caa tca gct atc ccc atg cac     144
Lys Val Gly Pro Ser Val Cys Ala Ile Gln Ser Ala Ile Pro Met His
        35                  40                  45 tgt cgt gat agg agc ctg tca agg tct gtc cta tgc gtc atc agg gat     192
Cys Arg Asp Arg Ser Leu Ser Arg Ser Val Leu Cys Val Ile Arg Asp
    50                  55                  60 ctc ctc tac ata aca gca tgt gct gct gtg cag tac tct ctg ttg gcg     240
Leu Leu Tyr Ile Thr Ala Cys Ala Ala Val Gln Tyr Ser Leu Leu Ala
65                  70                  75                  80 tta gta ccc ccg gac tca acc ctc ctg agg gca gtc ctc tgg ggt gtt     288
Leu Val Pro Pro Asp Ser Thr Leu Leu Arg Ala Val Leu Trp Gly Val
                85                  90                  95 tac att ttc tgg caa ggc gtc ttt ttt act ggt att tgg gtg atg ggc     336
Tyr Ile Phe Trp Gln Gly Val Phe Phe Thr Gly Ile Trp Val Met Gly
            100                 105                 110 cac gag tgc ggc cat ggg gct ttt tcc cct tat tct atg ctg aac gat     384
His Glu Cys Gly His Gly Ala Phe Ser Pro Tyr Ser Met Leu Asn Asp
        115                 120                 125 agt att ggt ttt gtc ctc cac tcg gcc ctc ttg gta ccc tac ttc agc     432
Ser Ile Gly Phe Val Leu His Ser Ala Leu Leu Val Pro Tyr Phe Ser
    130                 135                 140
```

```
tgg cag tac tcc cat gcg agg cac cat aag ttc acc aac cac gct act    480
Trp Gln Tyr Ser His Ala Arg His His Lys Phe Thr Asn His Ala Thr
145                 150                 155                 160 aag ggt gag agc cat gtc ccc agc ctg gaa agt gag atg ggc gta ttc    528
Lys Gly Glu Ser His Val Pro Ser Leu Glu Ser Glu Met Gly Val Phe
                165                 170                 175 agt cgt ata cag aag gcc ctg gag ggt tat ggt ctc gat gat gtc ttc    576
Ser Arg Ile Gln Lys Ala Leu Glu Gly Tyr Gly Leu Asp Asp Val Phe
            180                 185                 190 cca gtc ttc cct ata gtg atg ctc ctg gtt ggg tat cct gtg tat ctc    624
Pro Val Phe Pro Ile Val Met Leu Leu Val Gly Tyr Pro Val Tyr Leu
        195                 200                 205 ttc tgg aat gca tca ggt ggg cgt gtg ggc tac gat cgc cgt ccg tac    672
Phe Trp Asn Ala Ser Gly Gly Arg Val Gly Tyr Asp Arg Arg Pro Tyr
    210                 215                 220 agc gac act aag cca tct cat ttc aat ccc aac ggt ggc ctt ttc cct    720
Ser Asp Thr Lys Pro Ser His Phe Asn Pro Asn Gly Gly Leu Phe Pro
225                 230                 235                 240 cct tat atg aga gag aaa gtc ctc ctt agt gga gtt ggc tgt agc ata    768
Pro Tyr Met Arg Glu Lys Val Leu Leu Ser Gly Val Gly Cys Ser Ile
                245                 250                 255 acc ctc ctt att ttg gcc tat tgt gct ggg agg gta ggc ctt agc agt    816
Thr Leu Leu Ile Leu Ala Tyr Cys Ala Gly Arg Val Gly Leu Ser Ser
            260                 265                 270 gta ttg ttg tgg tat ggt tgt ccc tac ctt atg acc aac gcc tgg cta    864
Val Leu Leu Trp Tyr Gly Cys Pro Tyr Leu Met Thr Asn Ala Trp Leu
        275                 280                 285 acg ctg tat acc tcc cta cag cac acg cat gaa gga gtc ccc cat tat    912
Thr Leu Tyr Thr Ser Leu Gln His Thr His Glu Gly Val Pro His Tyr
    290                 295                 300 ggc gat gag gct ttc acc ttc atc aga ggt gcc tta gct tct atc gat    960
Gly Asp Glu Ala Phe Thr Phe Ile Arg Gly Ala Leu Ala Ser Ile Asp
305                 310                 315                 320 cgt cca ccg tat ggc att ttc tct acg cat ttt cac cac gaa att ggc   1008
Arg Pro Pro Tyr Gly Ile Phe Ser Thr His Phe His His Glu Ile Gly
                325                 330                 335 acc act cat gtt ctg cac cac att gat tct agg atc ccc tgt tac cat   1056
Thr Thr His Val Leu His His Ile Asp Ser Arg Ile Pro Cys Tyr His
            340                 345                 350 gct aga gaa gcc act gat gct atc aag cct att ctg ggg gat tac tat   1104
Ala Arg Glu Ala Thr Asp Ala Ile Lys Pro Ile Leu Gly Asp Tyr Tyr
        355                 360                 365 agg gag gat ggt act cct ata gta aag gca ttt ttg aag gtc cac aga   1152
Arg Glu Asp Gly Thr Pro Ile Val Lys Ala Phe Leu Lys Val His Arg
    370                 375                 380 gag tgc aag ttc atc gga ggc ctc aac ggc gtc cag ttt tac cgt cct   1200
Glu Cys Lys Phe Ile Gly Gly Leu Asn Gly Val Gln Phe Tyr Arg Pro
385                 390                 395                 400 ggg cag cgg ccg cag cag cag ccc tgc ggc agc aac gct cgc act tct   1248
Gly Gln Arg Pro Gln Gln Gln Pro Cys Gly Ser Asn Ala Arg Thr Ser
                405                 410                 415 cgt tag                                                            1254
Arg

<210> SEQ ID NO 24
<211> LENGTH: 417
<212> TYPE: PRT
<213> ORGANISM: Perkinsus marinus

<400> SEQUENCE: 24

Met Thr Gln Thr Glu Val Gln Ala Gly Pro Cys Arg Asp Gly Arg Asn
```

```
              1               5                  10                 15
Leu Lys Ser Glu Ala Asp Val Lys Gly Phe Thr Ala Glu Glu Phe Thr
                    20                  25                  30
Lys Val Gly Pro Ser Val Cys Ala Ile Gln Ser Ala Ile Pro Met His
                    35                  40              45
Cys Arg Asp Arg Ser Leu Ser Arg Ser Val Leu Cys Val Ile Arg Asp
            50                  55                  60
Leu Leu Tyr Ile Thr Ala Cys Ala Ala Val Gln Tyr Ser Leu Leu Ala
65                      70                  75                  80
Leu Val Pro Pro Asp Ser Thr Leu Leu Arg Ala Val Leu Trp Gly Val
                    85                  90                  95
Tyr Ile Phe Trp Gln Gly Val Phe Thr Gly Ile Trp Val Met Gly
                    100                 105                 110
His Glu Cys Gly His Gly Ala Phe Ser Pro Tyr Ser Met Leu Asn Asp
                115                 120                 125
Ser Ile Gly Phe Val Leu His Ser Ala Leu Leu Val Pro Tyr Phe Ser
            130                 135                 140
Trp Gln Tyr Ser His Ala Arg His His Lys Phe Thr Asn His Ala Thr
145                 150                 155                 160
Lys Gly Glu Ser His Val Pro Ser Leu Glu Ser Glu Met Gly Val Phe
                    165                 170                 175
Ser Arg Ile Gln Lys Ala Leu Glu Gly Tyr Gly Leu Asp Asp Val Phe
                180                 185                 190
Pro Val Phe Pro Ile Val Met Leu Leu Val Gly Tyr Pro Val Tyr Leu
            195                 200                 205
Phe Trp Asn Ala Ser Gly Gly Arg Val Gly Tyr Asp Arg Arg Pro Tyr
            210                 215                 220
Ser Asp Thr Lys Pro Ser His Phe Asn Pro Asn Gly Gly Leu Phe Pro
225                 230                 235                 240
Pro Tyr Met Arg Glu Lys Val Leu Leu Ser Gly Val Gly Cys Ser Ile
                    245                 250                 255
Thr Leu Leu Ile Leu Ala Tyr Cys Ala Gly Arg Val Gly Leu Ser Ser
                260                 265                 270
Val Leu Leu Trp Tyr Gly Cys Pro Tyr Leu Met Thr Asn Ala Trp Leu
            275                 280                 285
Thr Leu Tyr Thr Ser Leu Gln His Thr His Glu Gly Val Pro His Tyr
                290                 295                 300
Gly Asp Glu Ala Phe Thr Phe Ile Arg Gly Ala Leu Ala Ser Ile Asp
305                 310                 315                 320
Arg Pro Pro Tyr Gly Ile Phe Ser Thr His Phe His His Glu Ile Gly
                    325                 330                 335
Thr Thr His Val Leu His His Ile Asp Ser Arg Ile Pro Cys Tyr His
                340                 345                 350
Ala Arg Glu Ala Thr Asp Ala Ile Lys Pro Ile Leu Gly Asp Tyr Tyr
                355                 360                 365
Arg Glu Asp Gly Thr Pro Ile Val Lys Ala Phe Leu Lys Val His Arg
            370                 375                 380
Glu Cys Lys Phe Ile Gly Gly Leu Asn Gly Val Gln Phe Tyr Arg Pro
385                 390                 395                 400
Gly Gln Arg Pro Gln Gln Pro Cys Gly Ser Asn Ala Arg Thr Ser
                    405                 410                 415

Arg
```

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 25
ggtaccatgg cgatcacgac gacgcagaca c                          31

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 26
gagctcctag tgggccttgc cgtgcttgat ctcc                       34

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 27
ggtaccatgg tcctcacaac cccggccctc                            30

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 28
ggagctctca gttctcagca cccatcttc                             29

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 29
ggtaccatgg ccaccgcatc tgcatc                                26

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 30
ggagctttag ccgtagtagg cctcctt                               27

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 31

```
ggtaccatgg cggctgcgac ggcgac                                          26
```

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 32

```
ggagctttag tcgtgcttcc tcttggg                                         27
```

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 33

```
ggtaccatga cccaaactga ggtcca                                          26
```

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 34

```
ggagctctaa cgagaagtgc gagcgt                                          26
```

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 35

```
ggtaccatgt cttctcttac cctcta                                          26
```

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 36

```
ggagctctat tccactatgg caacag                                          26
```

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 37

```
ggtaccatga ctacttcaac cactac                                          26
```

<210> SEQ ID NO 38
<211> LENGTH: 26
<212> TYPE: DNA
<213> ORGANISM: Artificial Sequence

```
<220> FEATURE:
<223> OTHER INFORMATION: Description of Artificial Sequence: primer

<400> SEQUENCE: 38
ggagctctac ctagcaagca atctct                                          26

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 39
ggatccacca tggcgatcac gacgacgcag acac                                 34

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 40
ggtctagact agtgggcctt gccgtgcttg atctcc                               36

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 41
ggatccagga tggtcctcac aaccccggcc ctc                                  33

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 42
ggtctagatc agttctcagc acccatcttc                                      30

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 43
ggatccatgg ccaccgcatc tgcatc                                          26

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 44
ggtctagatt agccgtagta ggcctccttt                                      29
```

```
<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 45
ggatccatgg cggctgcgac ggcgac                                    26

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 46
ggtctagatt agtcgtgctt cctcttggg                                 29

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 47
ggatccatga cccaaactga ggtcca                                    26

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 48
ggtctagact aacgagaagt gcgagcgt                                  28

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 49
ggatccatgt cttctcttac cctcta                                    26

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 50
ggtctagact attccactat ggcaacag                                  28

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 51
```

```
ggatccatga ctacttcaac cactac                                          26

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 52
ggtctagact acctagcaag caatctct                                        28

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (21)..(21)
<223> OTHER INFORMATION: n is inosine
<220> FEATURE:
<221> NAME/KEY: misc_feature
<222> LOCATION: (24)..(24)
<223> OTHER INFORMATION: n is inosine

<400> SEQUENCE: 53
ggntgghtng gncaygayky nksnca                                          26

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (6)..(6)
<223> OTHER INFORMATION: n is a, c, g, or t

<400> SEQUENCE: 54
ggraanagrt grtgytcdat ytg                                             23

<210> SEQ ID NO 55
<211> LENGTH: 4
<212> TYPE: PRT
<213> ORGANISM: Unknown
<220> FEATURE:
<223> OTHER INFORMATION: Cyt b5 motif

<400> SEQUENCE: 55

His Pro Gly Gly
 1

<210> SEQ ID NO 56
<211> LENGTH: 29
<212> TYPE: DNA
```

```
<213> ORGANISM: Artificial Sequence
<220> FEATURE:
<223> OTHER INFORMATION: Description of Artificial Sequence: primer

<400> SEQUENCE: 56
caagtaccac ccgggcggca gcagggcca                                              29

<210> SEQ ID NO 57
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 57
tggccctgct gccgcccggg tggtacttg                                              29
```